(12) United States Patent
Tanabe et al.

(10) Patent No.: US 8,323,896 B2
(45) Date of Patent: Dec. 4, 2012

(54) EPIDERMAL GROWTH FACTOR (EGF) EXPRESSION AND/OR POLYMORPHISMS THEREOF FOR PREDICTING THE RISK OF DEVELOPING CANCER

(75) Inventors: Kenneth K Tanabe, Brookline, MA (US); Bryan C Fuchs, Quincy, MA (US); Hiroshi Kawasaki, Osaka (JP)

(73) Assignee: The General Hospital Corporation, Boston, MA (US)

( * ) Notice: Subject to any disclaimer, the term of this patent is extended or adjusted under 35 U.S.C. 154(b) by 283 days.

(21) Appl. No.: 12/594,010

(22) PCT Filed: Mar. 28, 2008

(86) PCT No.: PCT/US2008/058667
§ 371 (c)(1),
(2), (4) Date: Oct. 19, 2009

(87) PCT Pub. No.: WO2008/121825
PCT Pub. Date: Oct. 9, 2008

(65) Prior Publication Data
US 2010/0184048 A1  Jul. 22, 2010

Related U.S. Application Data

(60) Provisional application No. 60/921,013, filed on Mar. 30, 2007.

(51) Int. Cl.
*C12Q 1/68* (2006.01)
*C07H 21/02* (2006.01)
*C07H 21/04* (2006.01)

(52) U.S. Cl. ...... 435/6.11; 435/6.1; 435/6.14; 435/6.17; 536/23.1; 536/23.5; 536/24.1; 536/24.31; 536/24.33

(58) Field of Classification Search ........................ None
See application file for complete search history.

(56) References Cited

OTHER PUBLICATIONS

GeneCard for the HTRA1 gene available via url: <genecards.org/cgi-bin/carddisp.pl?gene=EGF>, printed on Jan. 12, 2012.*
Hirschhorn et al. Genetics in Medicine. vol. 4, No. 2, pp. 45-61, Mar. 2002.*
, Lucentini et al. The Scientist (2004) vol. 18, p. 20.*
Wacholder et al. J. Natl. Cancer Institute (2004) 96(6):434-442.*
Halushka et al. Nature. Jul. 1999. 22: 239-247.*
Qi et al. Pathology. 2009. 41: 555-560.*
Goto et al. Cancer Epidemiol Biomarkers Prey. 2005. 14: 2454-2456.*
Zhu et al. J Human Genetics. 2010. 55: 236-240.*
Araujo et al. Experimental Biology and Medicine. 2009. 241-245.*
Amend, K. L., et al., "EGF gene polymorphism and the risk of incident primary melanoma." Cancer Res 2004;64 :2668-72.
Bhowmick, D. A., et al., "A functional polymorphism in the EGF gene is found with increased frequency in glioblastoma multiforme patients and is associated with more aggressive disease." Cancer Res 2004;64: 1220-3.
Blanc, P., et al., "Mitotic responsiveness of cultured adult human hepatocytes to epidermal growth factor, transforming growth factor alpha, and human serum." Gastroenterology 1992; 102:1340-50.
Borlak, J., et al., "Epidermal growth factor-induced hepatocellular carcinoma: gene expression profiles in precursor lesions, early stage and solitary tumours." Oncogene 2005;24:1809-19.
Carpenter, G., et al., "Epidermal growth factor." Annu Rev Biochem 1979;48:193-216.
Cohen, S. "Isolation of a mouse submaxillary gland protein accelerating incisor eruption and eyelid opening in the new-born animal." J Biol Chem 1962;237: 1555-62.
Ding, C., et al., "Simultaneous quantitative and allele-specific expression analysis with real competitive PCR." BMC Genet 2004;5:8.
Fisher, D. A., et al., "Metabolism and effects of epidermal growth factor and related growth factors in mammals." Endocr Rev 1990;1 1:418-42.
Greulich, H., et al., "Oncogenic transformation by inhibitor-sensitive and -resistant EGFR mutants." PLoS Med 2005;2:e313.
Hoffmann, B., et al., "Proliferation of fetal rat hepatocytes in response to growth factors and hormones in primary culture." J Cell Physiol 1989;139:654-62.
Lakshmanan, J. et al., "Epidermal growth factor prohormone is secreted in human urine." Am. J. Physiol. 1992; 263, E142-E150.

(Continued)

*Primary Examiner* — Carla Myers
(74) *Attorney, Agent, or Firm* — David S. Resnick; Nixon Peabody LLP

(57) ABSTRACT

The present invention relates to diagnostic and prognostic methods to determine the likelihood of a subject who has a inflammatory disease or liver disease of developing cancer. In particular, the present invention relates to methods for identifying subjects with increased susceptibility to developing cancer, such as hepatocellular carcinoma (HCC) where the subject has an inflammatory disease, such as, but not limited to cirrhosis, by identifying a variance or polymorphism in the human EGF gene. In particular, the methods of the present invention relate to identifying subjects with increased susceptibility to developing cancer such as HCC, where the subject has an inflammatory disease, such as but not limited to cirrhosis, and the subject is identified to have a single nucleotide polymorphism 61A>G in the 5'UTR of the EGF gene. Alternatively, the methods of the present invention relate to identifying subjects with increased susceptibility to developing cancer such as HCC, where the subject has an inflammatory disease, such as but not limited to cirrhosis, and the subject is identified to have increased expression of EGF as compared to a reference level of EGF expression. The present invention also relates to administering an effective amount of an anti-cancer therapy to subjects identified to have an increased susceptibility of developing cancer such as HCC by the methods as disclosed herein, and kits to identify a subject with a 61A>G polymorphism in the 5'UTR of the EGF gene or kits to determine increased EGF expression in subjects with chronic inflammatory disease.

4 Claims, 13 Drawing Sheets

OTHER PUBLICATIONS

Le Gall, S. M., et al., "Regulated Cell Surface Pro-EGF Ectodomain Shedding is a Zinc Metalloprotease-dependent Process." JBC 2003: 45255-68.

Lev Ran, A. et al., "Human serum and plasma have different sources of epidermal growth factor." Am. J. Physiol. 1990, 259; R545-R548.

Llovet, J. M., et al., "Hepatocellular carcinoma." Lancet 2003;362:1907-17.

Lynch, T. J., et al. "Activating mutations in the epidermal growth factor receptor underlying responsiveness of non-small-cell lung cancer to gefitinib." N. Engl. J. Med. 2004;350:2129-2 139.

Marti, et al., "Biological Effects of EGF, with Emphasis on the GI Tract and Liver: An Update." Hepatology 1989. 9; 126-138.

Mullhaupt, B., et al., "Liver expression of epidermal growth factor RNA. Rapid increases in immediate-early phase of liver regeneration." J Biol Chem 1994;269: 19667-70.

Park, J. G., et al., "Characterization of cell lines established from human hepatocellular carcinoma." Int J Cancer 1995;62:276-82.

Parkin, D. M., et al., "Global cancer statistics." 2002. CA Cancer J Clin 2005;55 :74-108.

Pesonen, et al., "Size Heterogeneity of EGF in Human Body Fluids." Life Sciences, vol. 40: 1987: 2489-94.

Sahin, U. et al., "Distinct roles for ADAM10 and ADAM17 in ectodomain shedding of six EGFR ligands." J. Cell Biol. 2004: 164: 769-79.

Sainsbury, J. R., et al., "Epidermal-growth-factor receptors and oestrogen receptors in human breast cancer." Lancet 1985;1 :364-366.

Schiffer, E., et al., "Gefitinib, an EGFR inhibitor, prevents hepatocellular carcinoma development in the rat liver with cirrhosis." Hepatology 2005;41: 307-14.

Shahbazi, M., et al., "Association between functional polymorphism in EGF gene and malignant melanoma." Lancet 2002;359:397-401.

Singletary, S. E., et al., "Biological effect of epidermal growth factor on the in vitro growth of human tumors." Cancer Res 1987;47:403-6.

Stern, D. F., et al., "Construction of a novel oncogene based on synthetic sequences encoding epidermal growth factor." Science 1987;23 5:321-4.

Stoscheck, C. M., et al., "Role of epidermal growth factor in carcinogenesis." Cancer Res, 1986;46: 1030-7.

Thomas, M. B., et al., "Hepatocellular carcinoma: the need for progress." J Clin Oncol 2005 ;23 :2892-9.

Tonjes, R. R., et al., "Autocrine mitogen IgEGF cooperates with c-myc or with the Hcs locus during hepatocarcinogenesis in transgenic mice." Oncogene 1995; 10:765-8.

Shahbazi, M. et al., "Association between functional polymorphism in EGF gene and malignant melanoma." Lancet 359:397-401, 2002.

Lim, Y. J. et al., "Epidermal growth factor gene polymorphism is different between schizophrenia and lung cancer patients in Korean population." Neuroscience Letters 374:157-160, 2005.

Randerson-Moor, J. A. et al., "The Relationship Between the Epidermal Growth Factor (EGF) 5'UTR Variant A61G and Melanoma/Nevus Susceptibility." J Invest Dermatol 123:755-759, 2004.

Saffroy, R. et al., "The MTHFR 677C>T polymorphism is associated with an increased risk of hepatocellular carcinoma in patients with alcoholic cirrhosis." Carcinogenesis 25(8):1443-1448, 2004.

Silvestri, L. et al., "CYP Enzyme Polymorphisms and Susceptibility to HCV-related Chronic Liver Disease and Liver Cancer." Int J Cancer 104:310-317, 2003.

Tanabe, K. K. et al., "Epidermal Growth Factor Gene Functional Polymorphism and the Risk of Hepatocellular Carcinoma in Patients With Cirrhosis." JAMA 299(1):53-60, 2008.

\* cited by examiner

Nucleic Acid sequence for EGF (SEQ ID NO:1)
>refseq|NM_001963|NM_001963 Homo
actgttgggagaggaatcgtatctccatatttcttctttcagccccaatccaagggttgt
agctggaactttccatcagttcttcctttcttttcctctctaagcctttgccttgctct
gtcacagtgaagtcagccagagcagggctgttaaactctgtgaaatttgtcataaggtg
tcaggtatttcttactggcttccaaagaaacatagataaagaaatctttcctgtggcttc
ccttggcaggctgcattcagaaggtctctcagttgaagaaagagcttggaggacaacagc
acaacaggagagtaaaagatgccccagggctgaggcctccgctcaggcagccgcatctgg
ggtcaatcatactccacttgcccgggccatgctccagcaaaatcaagctgttttcttttg
aaagttcaaactcatcaagattatgctgctcactcttatcattctgttgccagtagtttc
aaaatttagttttgttagtctctcagcaccgcagcactggagctgtcctgaaggtactct
cgcaggaaatgggaattctacttgtgtgggtcctgcacccttcttaattttctcccatgg
aaatagtatctttaggattgacacagaaggaaccaattatgagcaattggtggtggatgc
tggtgtctcagtgatcatggattttcattataatgagaaaagaatctattgggtggattt
agaaagacaacttttgcaaagagttttttctgaatgggtcaaggcaagagagagtatgtaa
tatagagaaaaatgtttctggaatggcaataaattggataaatgaagaagttatttggtc
aaatcaacaggaaggaatcattacagtaacagatatgaaaggaaataattcccacattct
tttaagtgctttaaaatatcctgcaaatgtagcagttgatccagtagaaaggtttatatt
ttggtcttcagaggtggctggaagcctttatagagcagatctcgatggtgtgggagtgaa
ggctctgttggagacatcagagaaaataacagctgtgtcattggatgtgcttgataagcg
gctgttttggattcagtacaacagagaaggaagcaattctcttatttgctcctgtgatta
tgatggaggttctgtccacattagtaaacatccaacacagcataatttgtttgcaatgtc
ccttttggtgaccgtatcttctattcaacatggaaaatgaagacaatttggatagccaa
caaacacactggaaaggacatggttagaattaacctccattcatcatttgtaccacttgg
tgaactgaaagtagtgcatccacttgcacaacccaaggcagaagatgacacttgggagcc
tgagcagaaactttgcaaattgaggaaaggaaactgcagcagcactgtgtgtgggcaaga
cctccagtcacacttgtgcatgtgtgcagagggatacgccctaagtcgagaccggaagta
ctgtgaagatgttaatgaatgtgcttttggaatcatggctgtactcttgggtgtaaaaa
caccctggatcctattactgcacgtgccctgtaggatttgttctgcttcctgatgggaa
acgatgtcatcaacttgtttcctgtccacgcaatgtgtctgaatgcagccatgactgtgt
tctgacatcagaaggtccttatgtttctgtcctgaaggctcagtgcttgagagagatgg
gaaaacatgtagcggttgttcctcacccgataatggtggatgtagccagctctgcgttcc
tcttagcccagtatcctgggaatgtgattgctttcctgggtatgacctacaactggatga
aaaaagctgtgcagcttcaggaccacaaccattttgctgtttgccaattctcaagatat
tcgacacatgcattttgatggaacagactatggaactctgctcagccagcagatgggaat

```
ggtttatgccctagatcatgaccctgtggaaaataagatatactttgcccatacagccct
gaagtggatagagagagctaatatggatggttcccagcgagaaaggcttattgaggaagg
agtagatgtgccagaaggtcttgctgtggactggattggccgtagattctattggacaga
cagagggaaatctctgattggaaggagtgatttaaatgggaacgttccaaataatcac
taaggagaacatctctcaaccacgaggaattgctgttcatccaatggccaagagattatt
ctggactgatacagggattaatccacgaattgaagttcttccctccaaggccttggccg
tctggttatagccagctctgatctaatctggcccagtggaataacgattgacttcttaac
tgacaagttgtactggtgcgatgccaagcagtctgtgattgaaatggccaatctggatgg
ttcaaaacgccgaagacttacccagaatgatgtaggtcacccatttgctgtagcagtgtt
tgaggattatgtgtggttctcagattgggctatgccatcagtaataagagtaaacaagag
gactggcaaagatagagtacgtctccaaggcagcatgctgaagccctcatcactggttgt
ggttcatccattggcaaaaccaggagcagatccctgcttatatcaaaacggaggctgtga
acatatttgcaaaagaggcttggaactgcttggtgttcgtgtcgtgaaggttttatgaa
agcctcagatgggaaaacgtgtctggctctggatggtcatcagctgttggcaggtggtga
agttgatctaaagaaccaagtaacaccattggacatcttgtccaagactagagtgtcaga
agataacattacagaatctcaacacatgctagtggctgaaatcatggtgtcagatcaaga
tgactgtgctcctgtgggatgcagcatgtatgctcggtgtatttcagagggagaggatgc
cacatgtcagtgtttgaaaggatttgctggggatggaaaactatgttctgatatagatga
atgtgagatgggtgtcccagtgtgccccctgcctcctccaagtgcatcaacaccgaagg
tggttatgtctgccggtgctcagaaggctaccaaggagatgggattcactgtcttgatat
tgatgagtgccaactggggtgcacagctgtggagagaatgccagctgcacaaatacaga
gggaggctatacctgcatgtgtgctggacgcctgtctgaaccaggactgatttgccctga
ctctactccaccccctcacctcagggaagatgaccaccactattccgtaagaaatagtga
ctctgaatgtcccctgtcccacgatgggtactgcctccatgatggtgtgtgcatgtatat
tgaagcattggacaagtatgcatgcaactgtgttgttggctacatcggggagcgatgtca
gtaccgagacctgaagtggtgggaactgcgccacgctggccacgggcagcagcagaaggt
catcgtggtggctgtctgcgtggtggtgcttgtcatgctgctcctcctgagcctgtgggg
ggcccactactacaggactcagaagctgctatcgaaaaacccaaagaatccttatgagga
gtcgagcagagatgtgaggagtcgcaggcctgctgacactgaggatgggatgtcctcttg
ccctcaaccttggtttgtggttataaaagaacaccaagacctcaagaatgggggtcaacc
agtggctggtgaggatggccaggcagcagatgggtcaatgcaaccaacttcatggaggca
ggagccccagttatgtggaatgggcacagagcaaggctgctggattccagtatccagtga
taagggctcctgtccccaggtaatggagcgaagctttcatatgccctcctatgggacaca
```

FIG. 3 (cont'd)

```
gacccttgaagggggtgtcgagaagccccattctctcctatcagctaacccattatggca
acaaagggccctggacccaccacaccaaatggagctgactcagtgaaaactggaattaaa
aggaaagtcaagaagaatgaactatgtcgatgcacagtatcttttctttcaaaagtagag
caaaactataggttttggttccacaatctctacgactaatcacctactcaatgcctggag
acagatacgtagttgtgcttttgtttgctcttttaagcagtctcactgcagtcttatttc
caagtaagagtactgggagaatcactaggtaacttattagaaacccaaattgggacaaca
gtgctttgtaaattgtgttgtcttcagcagtcaatacaaatagattttttgtttttgttgt
tcctgcagccccagaagaaattaggggttaaagcagacagtcacactggtttggtcagtt
acaaagtaatttctttgatctggacagaacatttatatcagtttcatgaaatgattggaa
tattacaataccgttaagatacagtgtaggcatttaactcctcattggcgtggtccatgc
tgatgattttgccaaaatgagttgtgatgaatcaatgaaaaatgtaatttagaaactgat
ttcttcagaattagatggccttattttttaaaatatttgaatgaaaacattttatttta
aaatattacacaggaggccttcggagtttcttagtcattactgtccttttcccctacaga
attttccctcttggtgtgattgcacagaatttgtatgtattttcagttacaagattgtaa
gtaaattgcctgatttgttttcattatagacaacgatgaatttcttctaattatttaaat
aaaatcaccaaaaacat
```

*FIG. 3 (cont'd)*

Amino acid sequence for EGF protein (Accession No: NP_001954). 1207 aa

```
   1 mlltliillp vvskfsfvsl sapqhwscpe gtlagngnst cvgpapflif shgnsifrid
  61 tegtnyeqlv vdagvsvimd fhynekriyw vdlerqllgr vflngsrqer vcnieknvsg
 121 mainwineev iwsnqqegii tvtdmkgnns hillsalkyp anvavdpver fifwssevag
 181 slyradldgv gvkalletse kitavsldvl dkrlfwiqyn regsnslics cdydggsvhi
 241 skhptqhnlf amslfgdrif ystwkmktiw iankhtgkdm vrinlhssfv plgelkvvhp
 301 laqpkaeddt wepeqklckl rkgncsstvc gqdlqshlcm caegyalsrd rkycedvnec
 361 afwnhgctlg ckntpgsyyc tcpvgfvllp dgkrchqlvs cprnvsecsh dcvltsegpl
 421 cfcpegsvle rdgktcsgcs spdnggcsql cvplspvswe cdcfpgydlq ldekscaasg
 481 pqpfllfans qdirhmhfdg tdygtllsqq mgmvyaldhd pvenkiyfah talkwieran
 541 mdgsqrerli eegvdvpegl avdwigrrfy wtdrgkslig rsdlngkrsk iitkenisqp
 601 rgiavhpmak rlfwtdtgin priessslqg lgrlviassd liwpsgitid fltdklywcd
 661 akqsvieman ldgskrrrlt qndvghpfav avfedyvwfs dwampsvirv nkrtgkdrvr
 721 lqgsmlkpss lvvvhplakp gadpclyqng gcehickkrl gtawcscreg fmkasdgktc
 781 laldghqlla ggevdlknqv tpldilsktr vsednitesq hmlvaeimvs dqddcapvgc
 841 smyarciseg edatcqclkg fagdgklcsd idecemgvpv cppasskcin teggyvcrcs
 901 egyqgdgihc ldidecqlgv hscgenasct nteggytcmc agrlsepgli cpdstppphl
 961 reddhhysvr nsdsecplsh dgyclhdgvc myiealdkya cncvvgyige rcqyrdlkww
1021 elrhaghgqq qkvivvavcv vvlvmlllls lwgahyyrtq kllsknpknp yeessrdvrs
1081 rrpadtedgm sscpqpwfvv ikehqdlkng gqpvagedgq aadgsmqpts wrqepqlcgm
1141 gteggcwipv ssdkgscpqv mersfhmpsy gtqtleggve kphsllsanp lwqqaraldpp
1201 hqmeltq
```

FIG. 4

EPIDERMAL GROWTH FACTOR (EGF) EXPRESSION AND/OR POLYMORPHISMS THEREOF FOR PREDICTING THE RISK OF DEVELOPING CANCER

CROSS-REFERENCE TO RELATED APPLICATIONS

This application is a National Phase Entry Application under 35 U.S.C. §371 of International Application PCT/US2008/058667, filed 28 Mar. 2008, which claims benefit under 35 U.S.C. 119(e) of U.S. Provisional Patent Application Ser. No. 60/921,013 filed on Mar. 30, 2007, the contents of which are incorporated herein in their entirety by reference.

FIELD OF THE INVENTION

This invention relates to the field of pharmacogenomics and specifically to the application of genetic polymorphism to diagnose and treat diseases. In particular, the present invention relates to altered levels of epidermal growth factor (EGF) expression in the diagnosis and treatment of a disease. More specifically, the present invention relates to the presence of polymorphisms in EGF gene and/or elevated EGF levels in subjects. Elevated levels of EGF and/or polymorphisms in the EGF gene or gene products in biological samples from subjects indicates the subject has increased likelihood of developing cancer, in particular hepatic cell carcinoma (HCC), in particular in subjects with liver disease. The present invention relates to methods and molecules for identifying one or more polymorphisms in the EGF gene and/or measurement of EGF levels, and also provides methods of diagnosing, prognosing and treating subjects with diseases associated with elevated EGF levels and/or one or more polymorphisms in the gene encoding EGF.

BACKGROUND OF THE INVENTION

Hepatocellular carcinoma (HCC) is the sixth most common solid tumor worldwide, with more than half occurring in China (Parkin et al., DM. Int J Cancer. 2006; 118(12):3030-3044). HCC is difficult to diagnose, in particular in early stages of the disease. Because of its poor prognosis, hepatocellular carcinoma is the third leading cause of cancer-related death. (Parkin et al., 2002. CA Cancer J Clin. 2005; 55(2):74-108). Because of its poor prognosis, it is the third leading cause of cancer-related death (2). Due to such poor prognosis, by the time a subject is diagnosed with HCC the disease has progresses to such an extent that current therapies are largely ineffective. Only a minority of patients with hepatocellular carcinoma are candidates for potentially curative treatments of resection, transplantation, or ablation.

As current therapies are ineffective for most HCC patients, prevention of HBV and HCV transmission, identification of high-risk populations suit able for screening and chemoprevention have been proposed as alternative strategies (Llovet et al., Lancet. 2003; 362(9399):1907-1917). Alternatively, identification of high-risk populations suitable for screening and chemoprevention have been proposed as alternative strategies (3).

Screening strategies for high-risk populations include alpha fetoprotein measurements and liver imaging. These techniques are costly and are hindered by suboptimal sensitivity and specificity. To this end, identification of molecular markers associated with an increased risk of hepatocellular carcinoma would better define populations at highest risk for hepatocellular carcinoma and can additionally define important therapeutic targets for prevention and treatment.

Transformation to HCC commonly occurs in the setting of underlying chronic liver disease (1). HCC commonly arises in the setting of hepatic cirrhosis (Thomas et al., J Clin Oncol. 2005; 23(13): 2892-2899) and chronic infection with hepatitis B virus (HBV) and hepatitis C virus (HCV) are the most important causes of cirrhosis and hepatocellular carcinoma. (IARC. Monographs on the Evaluation of Carcinogenic Risks to Humans. Vol 59. Lyon, France: International Agency for Research on Cancer; 2004).

EGF, first isolated in 1962 (4), has many biological functions. It stimulates proliferation and differentiation of epidermal and epithelial tissues (5, 6). EGF is a known mitogen for adult (7) and fetal hepatocytes (8) grown in culture, and its expression is up-regulated during liver regeneration (9). Mounting evidence supports a role for EGF in malignant transformation and tumor progression (10). EGF enhances in vitro growth of human epithelial and mesenchymal-derived tumors (11). Over-expression of a secreted human EGF fusion protein (IgEGF) in fibroblasts enhances their transformation to fibrosarcomas (12). Transgenic mice with liver-specific over-expression of IgEGF develop HCC (13). Gene expression profiles comparing normal liver tissue to liver tumors in these mice suggest a role for an autocrine mechanism during EGF-induced hepatocarcinogenesis (14).

SUMMARY OF THE INVENTION

The present invention provides diagnostic and prognostic methods used to determine the likelihood of a subject developing cancer. In one embodiment, the subject has liver disease. The methods comprise detecting elevated levels of epidermal growth factor (EGF) in a subject and/or detecting EGF polymorphism in a subject. Clinical relevance includes, but is not specifically limited to a subject's likelihood of developing a cancer in subjects with an inflammatory disorder or disease. In some embodiments the inflammatory disease is liver disease and in some instances the liver disease is cirrhosis. In one embodiment, the cancer is hepatocellular carcinoma (HCC). Further clinical relevance includes, but is not limited to, subjects with liver disease can be monitored more closely and treated with preventative and/prophylactic therapies such as anti-cancer and/or antagonists to the EGF-EGFR pathway.

In some embodiments, the present invention provides methods to determining the level of gene expression of EGF, in particular whether the EGF gene is over- or under-expressed in a sample as compared to a control sample. In another aspect, methods to determine the presence or absence of allelic variant of the EGF gene are provided. In yet a further embodiment, it requires determining the identity of a nucleotide of an allelic variant of EGF. In a further aspect, one or more of these is identified in the method of this invention.

In alternative embodiments, the present invention also provides methods and compositions to detect EGF levels and/or polymorphisms in the EGF gene. In some embodiments, the EGF levels are detected using nucleic acids to detect levels of the EGF RNA and/or polymorphisms in EGF. In yet further aspect, agents, for example antibodies or other molecules can be used to detect EGF protein expression levels. In another embodiment, the present invention provides methods using nucleic acids encompassing the polymorphic region of interest or adjacent to the polymorphic region as probes or primers.

In other embodiments, the present invention provides molecules and methods for diagnosis, prognosis, and treat subjects with liver disease with elevated EGF levels and/or polymorphisms in EGF gene and/or gene products. In particular, the present invention provides novel methods for screening subjects for risk of developing hepatocellular carcinoma (HCC). In some embodiments, the subjects have liver disease. In particular, the present invention relates to methods for screening subjects with increased susceptibility to, or current affliction with, a disease or disorder associated with a variance (for example a mutation and/or polymorphism) in the human EGF gene. In some embodiments, the variance in the human EGF gene product results in increased or elevated levels of the EGF gene product. In some embodiments, the subject has an inflammatory disease. In a further embodiment, the inflammatory disease is a liver disease. For example, such diseases include but are not limited to, cirrhosis, bilirubin metabolism, jaundice, syndromes of Gilbert's, Crigler-Najjar, Dubin-Johnson and Rotor; intrahepatic cholestasis, hepatomegaly, portal hypertension, ascites, Budd-Chiari syndrome, portal-systemic encephalopathy, fatty liver, steatosis, Reye's syndrome, liver diseases due to alcohol, alcoholic hepatitis or cirrhosis, fibrosis and cirrhosis, fibrosis and cirrhosis of the liver due to inborn errors of metabolism of exogenous substances, storage diseases, syndromes of Gaucher's, Zellewger's, Wilson's disease, acute or chronic hepatitis, chronic active hepatitis, viral hepatitis and its variants, inflammatory conditions of the liver due to viruses, bacteria, fungi, protozoa, helminthes, drug-induced disorders of the liver, chronic liver diseases like primary sclerosing cholangitis, alpha$_1$-antitrypsin-deficiency, primary biliary cirrhosis, postoperative liver disorders like intrahepatic cholestasis, hepatic granulomas, vascular liver disorders associated with systematic disease etc.

In one embodiment, the methods comprise obtaining a biological sample from a subject and screening for variations (e.g. changes) in the human EGF gene or gene products relative to a control group (e.g. wildtype, positive and/or negative control group). In other embodiments, screening for variations in the 5' untranslated region (5'UTR) of the human EGF gene relative to a control group.

In one embodiment of the invention, variances (e.g. a mutation and/or polymorphism) are variances in the human EGF gene which increases the expression of the EGF gene product. One such variance is, for example, where there is a guanine (G) is present at position 61 in SEQ ID NO:1 in one allele compared to a adenosine (A) in another allele. This variance is a single nucleotide polymorphism in the 5'UTR of the EGF gene, and is termed "61A>G" or "61A/G" herein. This 61A>G variance is designated rs4444903 (NCBI). Subjects that have two G alleles at position 61 (i.e. are homozygous (G/G)) or have one G-allele at position 61 (i.e. are heterozygous (A/G)) identify subjects with in increased risk of developing cancer, in particular hepatocellular carcinoma (HCC) in subjects with chronic inflammatory disease, for example liver disease and/or cirrhosis.

The presence or absence of the polymorphisms and/mutations as disclosed herein can be determined by any means known in the art. In one embodiment, the methods of the present invention encompass the screening for any changes in the nucleic acid sequence of the 5'UTR of the EGF gene, and/or the coding region of the EGF gene. For example, the nucleotides to be screened are, but not limited to, the nucleotides located at positions 61 in the 5'UTR of the EGF gene (SEQ ID NO:1).

Also encompassed in the methods of this invention is the screening and/or detection of any change or variation in coding and/or non-coding region of EGF gene, including 3' UTR sequences, and intron sequences of the EGF gene is encompassed in this invention, particularly if the variance alters the expression of the EGF gene, for example increase the expression of EGF, and therefore is a predictor of the clinical phenotype in terms of increased risk of developing cancer, for example HCC. If a subject is identified with having a variance results in an increase in EGF expression, the subject has increased likelihood of risk of developing cancer, in particular HCC in subjects with liver disease and/or cirrhosis. Changes in non-coding regions also include modifications in the nucleic acid such as methylation and acetylation. In such embodiments, any variances or changes that result in an increased EGF RNA stability and/or increase in EGF expression function as "susceptibility alleles" and are encompassed in this invention and will likely indicate a subject will have an increased likelihood developing cancer, in particular HCC, in particular if the subject has an inflammatory disease, for example liver disease. Variances in the 5'UTR of the EGF gene can also be determined via sequence analysis, such as, for example, amplification assays, such as PCR, qPCR, RT-PCR or gene arrays.

Accordingly, also encompassed in the present invention are methods for screening for variances in the EGF gene that affect the stability of the EGF RNA. For example, variances (mutations and/or polymorphisms) that result in an increase in the stability of the EGF RNA can predict the clinical phenotype in terms of increased likelihood of developing cancer, in particular hepatocellular carcinoma in subjects with cirrhosis.

While a previous report by Shahbazi et al. (2002, Lancet, 359; 397-401) (15) identified an A to G transition at position 61 in the 5' untranslated region of the EGF gene resulted in increased secretion of EGF from PBMC cells in culture from individuals with the homozygous (G/G) genotype as compared with normal (or wildtype) individuals with the A/A genotype, and that the G/G genotype was also associated with a 4.9-fold increase in relative risk of developing malignant melanoma, this is different from the present invention as disclosed herein, because Shahbazi et al. only correlates the presence of A to G transition at position 61 in the 5'UTR of the EGF with melanoma. Further, Shahbazi et al. did not identify subjects with an inflammatory disease that carry the A to G transition at position 61 in the 5'UTR of the EGF to have an increased likelihood to develop cancer. The present invention as disclosed herein correlates the G transition at position 61 in the 5'UTR of the EGF as a predictor of developing HCC in subjects with an inflammatory disease, such as but not limited to liver disease, for example cirrhosis.

Accordingly, variances in the human 5'UTR of EGF and/or coding region of EGF gene can also be detected in the gene product (e.g. mRNA or protein). The detection of increased levels of the EGF gene product (either protein and/or RNA for example) in a biological sample likely indicates a subject has increase risk of developing cancer, in particular hepatocellular carcinoma (HCC) in a subject with inflammatory disease, for example liver disease.

In another embodiment, the present invention further provides that the absence or presence of a variance in the human EGF gene can be detected by analyzing gene product (e.g. RNA and/or EGF protein). In one embodiment, a probe can specifically bind to a variant of EGF gene product or protein. In some embodiments, a probe can bind to different variants of the EGF protein. In some embodiments, a plurality of different probes are used, where each probe can bind to at least one or more variants of the EGF gene and/or EGF gene product or protein. In one embodiment, the probe is an antibody or other molecule or agent that preferentially binds to the EGF protein. The presence of higher or increased levels of the EGF protein or mRNA in a biological sample from a subject as compared to the levels of EGF protein or mRNA in a reference biological sample predicts the likelihood of a subject at increased risk of developing cancer, in particular hepatic cell carcinoma (HCC) in subjects with cirrhosis and/or liver disease. In some embodiments, the reference biological sample is from a normal subject, and in some embodiments, the reference biological sample is from the same subject where the sample was taken at a different time point.

Alternatively, probes can also be used for screening for variances in EGF protein expression levels and/or in variances in the amino acid sequence of the EGF protein. For example, but not limited to, one can screen for any changes in the amino acid sequence of EGF (SEQ ID NO:2).

In some embodiments the biological sample is from a normal subject. In other embodiments, the biological sample is from a subject with a disease and/or disorder associated with inflammatory condition. In some embodiments, the inflammatory disorder is liver disease. And in further embodiments, the liver disease is for example, but not limited to, cirrhosis. A variance of a 'susceptibility allele' in the 5'UTR of the EGF gene is indicative of the presence of, or the possibility of future affliction with developing cancer, for example hepatic cell carcinoma (HCC). For example, susceptibility alleles of this invention include, but are not limited to, a G allele at position 61 in the EGF gene (61A/G), or any variance in the 5'UTR and/or 3'UTR and or intron and exon sequences of the EGF gene that result in increase expression of the EGF protein.

In one aspect, the biological sample or sample to be tested is the actual liver tissue and/or tumor tissue. In another aspect the sample can be normal tissue isolated adjacent to the tumor. In a further aspect, the sample is any tissue of the subject, and can include, for example but not limited to, plasma, serum, blood, peripheral blood lymphocytes, liver, bile, urine etc.

The detection of the presence or absence of a least one nucleic acid variance can be determined by amplifying a segment of nucleic acid encoding the 5'UTR of the EGF gene. The segments to be amplified is 1000 nucleotides in length, 500 nucleotides in length or 100 nucleotides in length or less. The segments to be amplified can include a plurality of variances.

The present invention provides methods, molecules, kits, and primers useful for detecting one or more polymorphic sites in polynucleotides encoding the epidermal growth factor (EGF) gene and gene products.

In some embodiments, the present invention provides polymorphisms in nucleic acids encoding epidermal growth factor (EGF) gene and expressed EGF molecule.

While in the exemplary embodiment variances in the 5' UTR of EGF gene in subjects with inflammatory disease, for example liver disease, indicate subjects are of increased likelihood to develop hepatic cell carcinoma (HCC), the methods of the present invention are not so limited. In one aspect, the cancer comprises a cancer or neoplasm that is treatable by use of chemotherapy, immunotherapy, radiotherapy surgery or alternative therapies such as thermal-therapy or hormonal therapy. In another aspect, the cancer is treatable by blocking or inhibiting one or more members of the Epidermal Growth Factor Receptor (EGFR) pathway. Non limiting examples of such cancers are for example, but are not limited to, hepatocellular carcinoma, rectal cancer, colorectal cancer, colon cancer, gastric cancer, lung cancer, esophageal cancers and melanoma.

In yet a further embodiment, the present invention provides a kit for amplifying and/or for determining the molecular structure of at least a portion of the EGF gene, comprising a probe or primer capable of detecting to the EGF gene and instructions for use. In one embodiment, the probe or primer is capable of detecting to an allelic variant of the EGF gene. In other aspect, the probe or primer is used to determine the expression level of the EGF gene. In yet a further embodiment, the kit contains a molecule, such as an antibody, that can detect the expression product of the EGF gene.

The present invention further provides a novel method for treating subjects affected with or at risk of developing cancer, in particular hepatocellular carcinoma (HCC). The methods involve determining whether the 5'UTR of the human EGF gene from a subject contains at least one nucleic acid variance, and/or determining whether EGF mRNA or protein levels are elevated relative to a control population. In some embodiments, where subjects are identified as having a variance at a 'susceptibility allele' which results in the increase in the expression of the EGF gene product (protein and/or RNA), the subject is administered a therapeutically effective amount of an anti-cancer therapy. Examples of anti-cancer therapies are known in the art, and in some embodiments the anti-cancer therapy is a therapy targeting the EFG-EGFR pathway. In another aspect, the present invention comprises administration of an appropriate therapy or combination therapy after identification of the at least one G-allele variance of the 61A>G polymorphism, or other susceptibility alleles in the EGF gene and/or altered levels of EGF protein and/or EGF RNA.

The present invention further provides for a method to assess the effects of the treatment by assessment of EGF mRNA or protein levels before, during, and/or after the treatment.

Accordingly, one aspect of the present invention relates to a method of identifying a subject with an inflammatory disease with having increased likelihood of developing cancer, the method comprising analyzing a biological sample from the subject for the presence of mutations and/or polymorphisms in the EGF gene, wherein the presence of at least one mutation and/or polymorphism that results in an increased level of EGF expression as compared to the level of EGF expression in the absence of said mutation and/or polymorphism identifies a subject with an inflammatory disease as having increased likelihood of developing cancer. In some embodiments, the subject is selected for an inflammatory disease prior to assessment for identification for increased risk of developing cancer.

Another aspect of the present invention relates to a method of identifying a subject with an inflammatory disease as having increased likelihood of developing cancer, the method comprising: (a) measuring the level of EGF gene product in a biological sample obtained from the subject; (b) comparing the level of EGF gene product in the biological sample from the subject with a reference EGF level; wherein an increase in the level of EGF gene product in the biological sample from the subject as compared to the reference EGF level identifies the subject with an inflammatory disease as having an increased likelihood of developing cancer.

Another aspect of the present invention relates to a method of identifying a subject with an inflammatory disease as having increased likelihood of developing or having cancer, the method comprising: (a) measuring the level of EGF gene product in a biological sample obtained from the subject at a first time point; (b) measuring the level of EGF gene product in a biological sample obtained from the subject at a second time point; the second time point being after the first time point; and (c) comparing the level of EGF gene product in the biological sample from the first time point with the level of EGF gene product in the biological sample from the second time point; where if an increase in the level of EGF gene product in the biological sample from the second time point is detected as compared to the level of EGF gene product in the biological sample from the first time point identifies the subject with an inflammatory disease as having an increased likelihood of developing cancer.

In some embodiments, the subject is selected for having an inflammatory disease prior to assessment for identification for increased risk of developing cancer, by either determining the presence of mutations and/or polymorphisms, or by measuring the level of EGF expression in a biological sample at one or more time points.

In some embodiments, the methods to identify a subject with an inflammatory disease with an increased risk of developing cancer as disclosed by the methods herein, further comprises comparing the level of the EGF gene product in the test biological sample from the first and/or the second time point with a reference EGF gene product level, where if an increase in the level of the EGF gene product in the biological sample from the first time point and/or from the second time point is detected as compared to the reference EGF gene product level, the subject is identified as having an increased likelihood of developing cancer.

In some embodiments in the methods to identify a subject with an inflammatory disease with an increased risk of developing cancer as disclosed herein, the subject is identified with a cancer which is hepatocellular carcinoma (HCC).

In some embodiments, the subject is selected for having an inflammatory disease prior to assessment for identification for increased risk of developing cancer, by either determining the presence of mutations and/or polymorphisms, or by measuring the level of EGF expression in a biological sample at one or more time points. In some embodiments, the inflammatory disorder is chronic-inflammatory disorder, for example a liver disease. In some embodiments, the liver disease is cirrhosis. Other liver disease include, for example but not limited to, Hepatitis A, Hepatitis B, Hepatitis C, hemochromatosis, bilirubin metabolism, jaundice, syndromes of Gilbert's, Crigler-Najjar, Dubin-Johnson and Rotor; intrahepatic cholestasis, hepatomegaly, portal hypertension, ascites, Budd-Chiari syndrome, portal-systemic encephalopathy, fatty liver, steatosis, Reye's syndrome, liver diseases due to alcohol, alcoholic hepatitis or cirrhosis, fibrosis and cirrhosis, fibrosis and cirrhosis of the liver due to inborn errors of metabolism of exogenous substances, storage diseases, syndromes of Gaucher's, Zellewger's, Wilson's disease, acute or chronic hepatitis, chronic active hepatitis, viral hepatitis and its variants, inflammatory conditions of the liver due to viruses, bacteria, fungi, protozoa, helminthes, drug-induced disorders of the liver, chronic liver diseases like primary sclerosing cholangitis, alpha$_1$-antitrypsin-deficiency, primary biliary cirrhosis, postoperative liver disorders like intrahepatic cholestasis, hepatic granulomas, vascular liver disorders associated with systematic disease.

In some embodiments, identification of a subject with an inflammatory disease with an increased risk of developing cancer by the methods as disclosed herein, involves determining the presence of a mutation and/or polymorphism in the EGF gene, for example such a mutation or polymorphism can be a single polymorphism (SNP). In some embodiments, the mutation and/or polymorphism is a non-coding region of the gene encoding EGF, for example in the 3' UTR or 5' UTR of the gene encoding EGF. In some embodiments, the mutation and/or polymorphism is a change of adenosine (A) in the 5'UTR of the EGF gene at position 61 of SEQ ID NO:1 to a guanine (G) (61A>G). In some embodiments, the presence of at least one mutation and/or polymorphism is heterozygous for at least one mutation and/or polymorphism, and in alternative embodiments, the presence of at least one mutation and/or polymorphism is homozygous for at least one mutation and/or polymorphism.

In some embodiments, identification of a subject with an inflammatory disease with an increased risk of developing cancer by the methods as disclosed herein involves either determining the presence of mutations and/or polymorphisms, or by measuring the level of EGF expression in a biological sample obtained from the subject. In some embodiments, the biological sample is selected from the group consisting of: serum, plasma, blood or tissue sample, such as for example but not limited to a biopsy tissue sample, such as a liver biopsy tissue sample. In some embodiments, a tissue sample is ex vivo cultivated biopsy tissue sample. Alternatively, a biological sample obtained from the subject can be, but is not limited to, any one or a combination of the following biological samples; blood, serum, plasma, urine, stool, spinal fluid, pleural fluid, sputum, nipple aspirates, lymph fluid, the external secretions of the skin, respiratory, intestinal, and genitourinary tracts, bile, tears, sweat, saliva, milk, cells, tumors, organs, or samples of in vitro cell culture constituent.

In some embodiments, identification of a subject with an inflammatory disease with an increased risk of developing cancer by the methods as disclosed herein, involves measuring the level of EGF expression in a biological sample obtained from the subject. In such embodiments, the levels of EGF gene product are levels of EGF protein or isoforms thereof, such as for example, but not limited to proEGF protein or matureEGF which is disclosed herein and commonly known by persons of ordinary skill in the art. EGF proteins, such as proEGF protein or matureEGF protein can be detected by any protein detection method commonly known by persons of ordinary skill in the art, such as but not limited to, detection methods using an antibody, human antibody, humanized antibody, recombinant antibody, monoclonal antibody, chimeric antibody, aptamer, peptide, or analogues and fragments thereof. In some embodiments, the levels of EGF protein or isoforms thereof are assessed by ELISA.

In alternative embodiments, the levels of EGF gene product measured are levels of EGF nucleic acid, such as but not limited to EGF messenger RNA (mRNA), or preproEGF mRNA which is disclosed herein and commonly known by persons of ordinary skill in the art. In some embodiments, EGF mRNA such as preproEGF can be assessed by any method commonly known by one of ordinary skill in the art, including use of probes which are nucleic acids or nucleic acid analogues, such as but not limited to, DNA, RNA, PNA, pseudo-complementary (pcPNA), locked nucleic acid (LNA) and variants and analogues thereof. In some embodiments, the level of EGF mRNA, such as preproEGF mRNA can be assessed by reverse-transcription polymerase-chain reaction (RT-PCR) or quantitative RT-PCR.

In some embodiments where identification of a subject with an inflammatory disease with an increased risk of developing cancer by the methods as disclosed herein involves determining the presence of mutations and/or polymorphisms, the presence of a mutation and/or polymorphism in the EGF gene can be detected by restriction fragment length polymorphism (RFLP), for example RFLP can be used to detect the 61A>G polymorphism in the EGF gene as disclosed in the Examples herein. In alternative embodiments, mutations and/or polymorphisms can be detected in the EGF gene by any methods commonly known by persons of ordinary skill in the art, such as but not limited to polymerase-chain reaction (PCR) or direct DNA sequencing, quantitative PCR (QPCR) or allele-specific QPCR as disclosed in the Examples herein to detect the 61A>G polymorphism in the EGF gene.

In some embodiments, where a subject with an inflammatory disorder is identified as having an increased likelihood of developing cancer, such as HCC by the methods as disclosed herein, the subject can be optionally administered an effective amount of at least one anti-cancer therapy. Any anti-cancer therapy commonly known by persons of ordinary skill in the art can be administered to such identified subjects, for example but not limited to, an anti-cancer therapy which is an agent or inhibitor of EGF and/or agent or inhibitor of EGF receptor (EGFR), such as but not limited to an agent or inhibitor of EGF and/or EGFR such as a nucleic acid inhibitors, DNA, RNA, siRNA, microRNAi, PNA, pcPNA, LNA, peptides, antibodies, small molecules, aptamer, peptidomimetics, and analogues and variants thereof.

Another aspect of the present invention relates to a kit to detect a guanine (G) allele at position 61 in the EGF sequence corresponding to SEQ ID NO:1, where the kit comprises at least (a) one primer pair comprising SEQ ID NO: 9 and SEQ ID NO: 11, or functional variants thereof; (b) one primer pair comprising SEQ ID NO: 10 and SEQ ID NO: 11 or functional variants thereof; and optionally (c) products and reagents to carry out EGF61A>G allele-specific QRT-PCR amplification.

An alternative kit is for detecting a guanine (G) allele at position 61 on the EGF sequence corresponding to SEQ ID NO:1 is encompassed in the present invention, where the kit comprises (a) at least one primer pair designed to anneal to the nucleic acid region of EGF at positions −78 to +164; (b) a AluI restriction enzyme or functional isoform thereof; and optionally (c) products and reagents to carry out the assay reaction. In some embodiments, the primers in such a kit can comprise the sequence primers SEQ ID NO: 3 and SEQ ID NO: 4 or functional variants thereof as disclosed herein in the Examples.

Another embodiments provides a alternative kit to amplify a region of the EGF gene comprising the guanine (G) allele at position 61, where such a kit comprises at least (a) one primer pair comprising SEQ ID NO: 5 and SEQ ID NO: 6 or functional variants thereof as disclose herein in the Examples; and optionally (b) products and reagents to carry out QRT-PCR amplification of human EGF RNA.

In some embodiments, the kits as disclosed herein further optionally comprise instructions and any other information or reagents or products useful to optimize or perform the kit.

Another aspect of the present invention relates to a method for preventing the development of cancer in subject, the method comprising selecting a subject with an inflammatory disease, and measuring the level of a EGF gene product in a biological sample obtained from a subject at least one time point according to the methods as disclosed herein, wherein a clinician reviews the results and if the clinician determines the subject has an increased level of EGF expression as compared to a reference level of EGF gene product expression, then the clinician directs the subject to be treated an effective amount of an appropriate anti-cancer therapy.

Another aspect of the present invention a method preventing the development of cancer in a subject, the method comprising selecting a subject with an inflammatory disease and detecting for the presence of at least one guanine (G) nucleotide at position 61 in the EGF gene corresponding to SEQ ID NO:1 in a biological sample obtained from the subject, wherein a clinician reviews the results and if the clinician determines the subject has at least one guanine (G) nucleotide at position 61 in the EGF gene corresponding to SEQ ID NO:1 then the clinician directs the subject to be treated an effective amount of an appropriate anti-cancer therapy.

Another aspect of the present invention relates to a method for preventing the development cancer in a subject, the method comprising selecting a subject with an inflammatory disease and assessing the presence of mutations and/or polymorphisms in the EGF gene in a biological sample obtained from a subject according to the methods as disclosed herein, wherein a clinician reviews the results and if the clinician determines the subject has the presence of at least one mutation and/or one polymorphism in the EGF gene which results in the increased stability of the EGF mRNA as compared to the absence of such a mutation and/or polymorphism, then the clinician directs the subject to be treated an effective amount of an appropriate anti-cancer therapy. In such an embodiment, the mutation and/or polymorphism is a single polymorphism (SNP), for example but not limited to a mutation and/or polymorphism is a non-coding region of the gene encoding EGF, such as in the 3' UTR, 5'UTR or intron sequences of the gene encoding EGF. In some embodiments, the mutation and/or polymorphism is a change of adenosine (A) in the 5'UTR of the EGF gene at position 61 of SEQ ID NO:1 to a guanine (G) (61A>G) as disclosed herein. In some embodiments, the subject is identified as being heterozygous or homozygous for at least one mutation and/or polymorphism.

In any of the methods as disclosed herein, the present invention enables identification of subject with an inflammatory disease with an increase risk of developing cancer, for example but not limited to hepatocellular carcinoma (HCC). In some embodiments, such a subject has been identified and/or selected for having an inflammatory disease or disorder, for example but not limited to a chronic-inflammatory disorder such as a liver disease such as cirrhosis. Other examples of inflammatory diseases which the subject has been identified to have, or have been selected for are, but are not limited to, liver diseases such as Hepatitis A, Hepatitis B, Hepatitis C, hemochromatosis, bilirubin metabolism, jaundice, syndromes of Gilbert's, Crigler-Najjar, Dubin-Johnson and Rotor; intrahepatic cholestasis, hepatomegaly, portal hypertension, ascites, Budd-Chiari syndrome, portal-systemic encephalopathy, fatty liver, steatosis, Reye's syndrome, liver diseases due to alcohol, alcoholic hepatitis or cirrhosis, fibrosis and cirrhosis, fibrosis and cirrhosis of the liver due to inborn errors of metabolism of exogenous substances, storage diseases, syndromes of Gaucher's, Zellewger's, Wilson's disease, acute or chronic hepatitis, chronic active hepatitis, viral hepatitis and its variants, inflammatory conditions of the liver due to viruses, bacteria, fungi, protozoa, helminthes, drug-induced disorders of the liver, chronic liver diseases like primary sclerosing cholangitis, alpha$_1$-antitrypsin-deficiency, primary biliary cirrhosis, postoperative liver disorders like intrahepatic cholestasis, hepatic granulomas, vascular liver disorders associated with systematic disease.

In some embodiments, the subject with an inflammatory disease as disclosed herein is mammalian subject, for example a subject with an inflammatory disease is a human.

Another aspect of the present invention relates to the use of at least one guanine (G) nucleotide at position 61 in the EGF gene corresponding to SEQ ID NO:1 in a subject with a inflammatory disease for the identification of a subject as having an increased likelihood of developing cancer as compared to a subject with a inflammatory disease that has two adenosine (A) nucleotides at position 61 in the EGF gene corresponding to SEQ ID NO:1.

Another aspect of the present invention relates to the use of the presence of two guanine (G) nucleotides at position 61 in the EGF gene corresponding to SEQ ID NO:1 in a subject with a inflammatory disease for the identification of a subject as having an increased likelihood of developing cancer as compared to a subject with a inflammatory disease that has at least one adenosine (A) nucleotides at position 61 in the EGF gene corresponding to SEQ ID NO:1.

Another aspect of the present invention relates to the use of the presence of at least one mutation and/or one polymorphism in the EGF gene of a subject with a inflammatory disease which results in the increased stability of the EGF mRNA as compared to the absence of such a mutation and/or polymorphism for the identification of a subject with an increased likelihood of developing cancer as compared to a subject with a inflammatory disease that does not have said mutation and/or polymorphism.

In some embodiments, where the use of the presence of at least one guanine (G) nucleotides at position 61 in the EGF gene corresponding to SEQ ID NO:1 or at least one mutation and/or one polymorphism in the EGF gene of a subject with a inflammatory disease to identify a subject with cancer, some embodiments the cancer is hepatocellular carcinoma (HCC). In some embodiments, the subject has been selected for an inflammatory disorder such as a chronic-inflammatory disorder, for example a liver disease. Such subjects can be identified and selected by one of ordinary skill in the art and by clinical criteria as disclosed herein. In some embodiments, the subjects have been identified with, or selected for a liver disease such as cirrhosis. In alternative embodiments, the subjects have been identified with, or selected for a liver disease selected from one of the following liver diseases but not limited to Hepatitis A, Hepatitis B, Hepatitis C, hemochromatosis, bilirubin metabolism, jaundice, syndromes of Gilbert's, Crigler-Najjar, Dubin-Johnson and Rotor; intrahepatic cholestasis, hepatomegaly, portal hypertension, ascites, Budd-Chiari syndrome, portal-systemic encephalopathy, fatty liver, steatosis, Reye's syndrome, liver diseases due to alcohol, alcoholic hepatitis or cirrhosis, fibrosis and cirrhosis, fibrosis and cirrhosis of the liver due to inborn errors of metabolism of exogenous substances, storage diseases, syndromes of Gaucher's, Zellewger's, Wilson's disease, acute or chronic hepatitis, chronic active hepatitis, viral hepatitis and its variants, inflammatory conditions of the liver due to viruses, bacteria, fungi, protozoa, helminthes, drug-induced disorders of the liver, chronic liver diseases like primary sclerosing cholangitis, alpha$_1$-antitrypsin-deficiency, primary biliary cirrhosis, postoperative liver disorders like intrahepatic cholestasis, hepatic granulomas, vascular liver disorders associated with systematic disease.

In some embodiments, the subject with an inflammatory disease or disorder is a mammal and in some embodiments the subject with an inflammatory disease or disorder is a human.

For a better understanding of the present invention together with other and further advantages and embodiments, reference is made to the following description taken in conjunction with the examples, the scope of which is set forth in the appended claims.

BRIEF DESCRIPTION OF FIGURES

FIG. 1A shows AluI RFLP analysis was used to perform EGF SNP genotype analysis in 12 human hepatoma cell lines. FIG. 1B shows allelic mRNA stability in PLC/PRF/5 cells (heterozygous at the EGF SNP) after treatment with actinomycin D (5 mg/ml) for the indicated times was determined by real-time PCR with allele-specific primers. FIG. 1C shows allelic mRNA stability in a primary hepatocyte culture from a patient heterozygous at the EGF SNP after treatment with actinomycin D. Results are representative of experiments performed in A/G patients.

FIG. 3 shows the nucleic acid sequence for human EGF (SEQ ID NO:1)

FIG. 4 shows the amino acid sequence for human EGF (SEQ ID NO:2)

FIG. 5A shows PLC/PRF/5 cell line, and FIG. 5B shows HepG2 cell line. FIGS. 5C and 5D each show results from a primary culture of human hepatocytes from a patient (two different patients) heterologous at the EGF gene single nucleotide polymorphism. Dashed lines indicate half-life (time at which the messenger RNA levels had dropped by 50%). Error bars indicate standard deviations.

FIG. 6A shows anchorage-independent growth of primary human hepatocytes and FIG. 6B shows THLE-5B cells assessed by an over agar assay after treatment with increasing doses of EGF.

FIG. 7A shows THLE-5B in vitro transformation assays in the presence of 10 ng/ml EGF with addition of the EGFR inhibitor AG1478 at concentrations (ranging between 0.01-1 µM) that are not cytotoxic to the cells as determined by MTT, shown in FIG. 7B. FIG. 7C shows THLE-5B in vitro transformation assays in the presence of 10 ng/ml EGF with addition of the EGFR inhibitor Erlotinib at concentrations (ranging between 0.01-1 µM) that are not cytotoxic to the cells as determined by MTT, shown in FIG. 7D. FIG. 7E shows THLE-5B in vitro transformation assays in the presence of 10 ng/ml EGF with addition of the EGFR inhibitor Gefitinib at concentrations (ranging between 0.01-1 µM) that are not cytotoxic to the cells as determined by MTT, shown in FIG. 7F.

DETAILED DESCRIPTION OF THE INVENTION

Figure 1A:
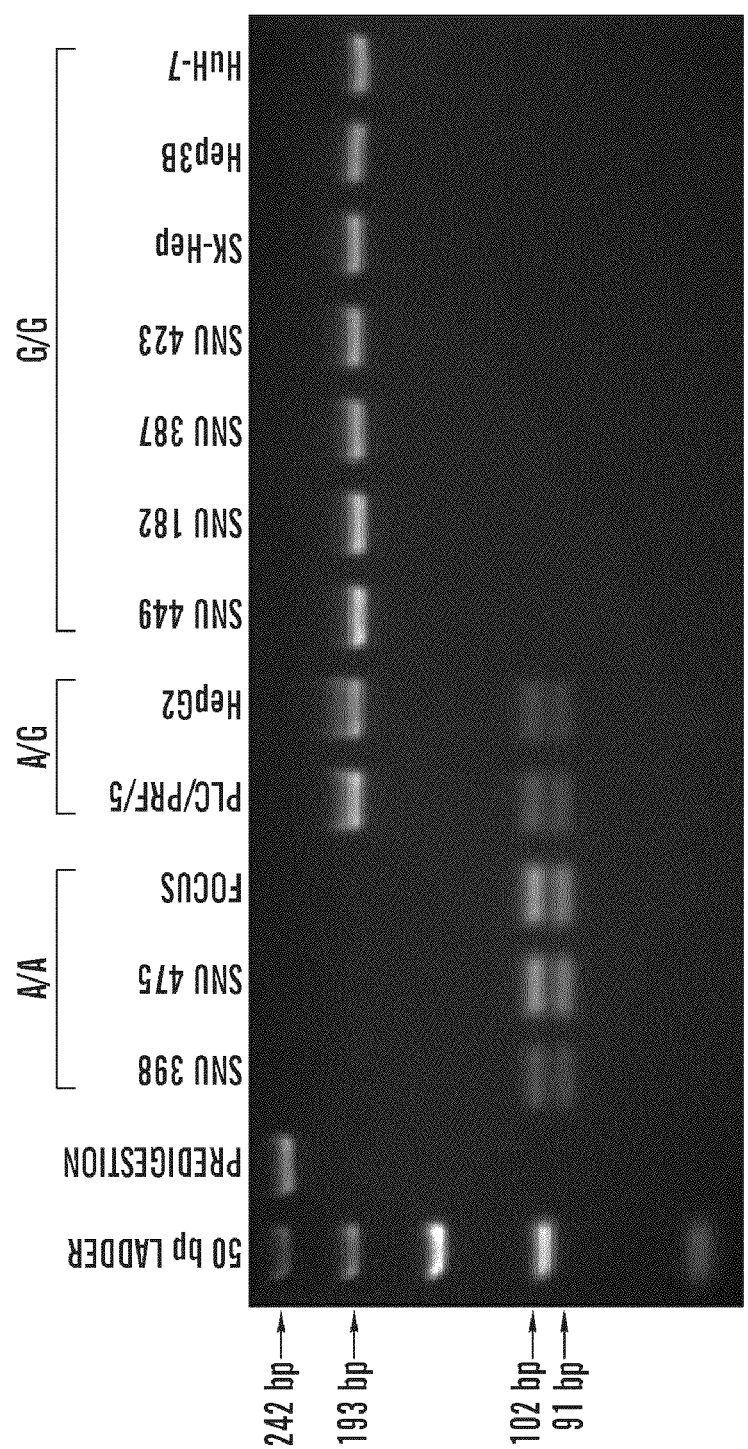
FIGS. 1A-1C show EGF SNP analysis and expression in human hepatoma cell lines.
Figure 1C:
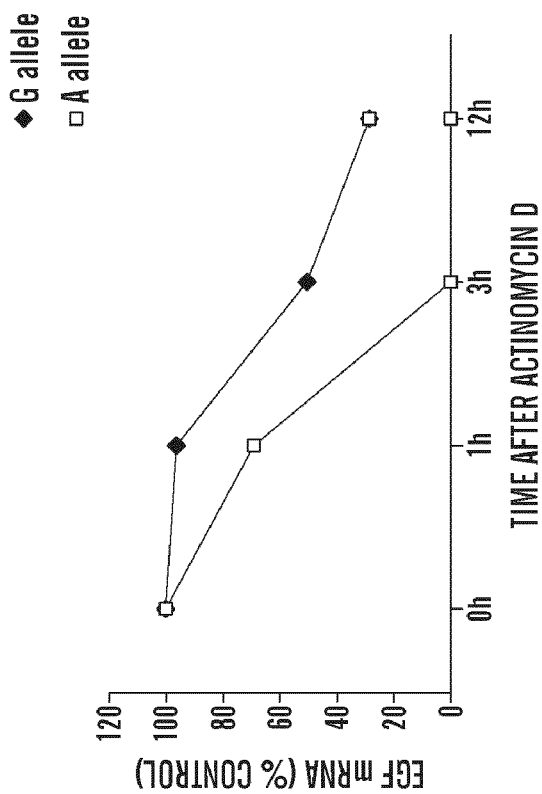

The inventors have discovered that variances (e.g. changes such as mutations and/or polymorphisms) in the human gene encoding EGF from the wild type sequence are associated with an increased risk of developing cancer, for example hepatic cell carcinoma. In particular the inventors have discovered that variance (mutations and/or polymorphisms) that result in an increased expression of the EGF gene product (for example but not limited to increase level of EGF RNA and/or EGF protein) predict increase likelihood of developing cancer, in particular HCC. The inventors of the present invention identified polymorphisms in the epidermal growth factor (EGF) gene by sequencing DNA obtained from normal individuals, from patients with liver disease, in particular cirrhosis. In addition, the inventors assessed the impact of the 61A>G polymorphism in the EGF gene on likelihood of developing cancer in a carefully phenotyped population of patients with cirrhosis.

The present invention is based on the discovery that variances (for example mutations and/or polymorphisms) in the gene encoding EGF compared with wildtype sequences of EGF predict increased risk of developing or being afflicted with cancer. In particular, the present invention relates to the discovery of predicting increased risk of developing hepatocellular carcinoma (HCC) in subjects with liver disease and/or an inflammatory disease.

The present invention is also based on the discovery that higher or increased levels of EGF mRNA and/or protein in a biological sample from a subject as compared to the levels of EGF mRNA and/or protein in a reference biological sample indicates the subject is of increased risk of developing HCC in subjects with liver disease and/or an inflammatory disease. In some embodiments, the biological sample is serum and/or liver tissue.

Accordingly, the present invention provides novel methods for screening subjects for mutations and polymorphisms in the EGF gene. In other embodiments, the present invention provides methods for screening subjects for levels of a variety of different EGF gene products, for example but not limited to levels of EGF mRNA and/or EGF protein. In particular, the present invention provides screening of subjects with increase susceptibility to, or current affliction with a disease or disorder associated with an inflammatory disorder, in particular a liver disease or liver disorder, to identify subjects with a likelihood of an increased risk of developing cancer, in particular HCC. In some embodiments, the subject is a human subject.

Mutations and/or Polymorphisms in the EGF Gene

The methods of this invention disclose a single nucleotide polymorphism (SNP) and/or mutations in the 5'-untranslated region (5' UTR) of the gene encoding human epidermal growth factor (EGF).

In one embodiment of the invention, a SNPs in the 5' UTR of the human EGF gene, referred to herein as "61A>G" was discovered to affect the expression of the gene product of EGF. This 61A>G variance is also designated rs4444903 (NCBI), and also known as "dbSNP126" or SNP002554212. The nucleotide numbers are based on Ensemble cDNA ID: ENSG00000138798 (Ref Seq ID, NM_001963) for EGF referred to herein as SEQ ID NO:1. Since the SNP is not in the coding region of the gene encoding human EGF but in the 5'UTR, it does not confer an amino acid change in the polynucleotide sequence. However, the 61A>G SNP resulted in significant changes in the expression of the gene product of the EGF gene. The SNP in EGF 5'UTR termed 61A>G, is where there is a guanine (G) at position 61 in SEQ ID NO:1 as apposed to the wildtype (e.g negative control) where adenosine (A) is present at position 61, and is alternatively referred to as "61A/G" or "A61G". An individual having a single allele (heterozygous) or two (homozygous) alleles comprising either a G-allele at 61A>G is associated with an increased likelihood of the risk of developing cancer, in particular hepatocellular carcinoma in subjects with inflammatory disease, for example liver disease and/or cirrhosis.

In one embodiment, the present methods of the present invention involves using a probe to screen for variances (e.g. changes, mutations, polymorphisms, SNPs) in either the nucleic acid sequence of the human EGF 5'UTR, and its variants from alternative splicing or homologues of human EGF gene relative to the control group or wild type allele.

According to the present invention, a "baseline" or "control" or "control group" can include a normal or negative control and/or disease or positive control, against which test samples can be compared. Therefore it can be determined, based on the control, whether the sample to be evaluated for mutations and/or polymorphisms in the human EGF 5'UTR has measurable difference or substantially no difference, as compared to the control group. In one aspect, the baseline control is a negative control. The negative control has the EGF 5'UTR as expected in the sample of normal (e.g. healthy, negative control) individual. Therefore, the term "negative control" used herein typically refers to a population of individuals whose sequence for the EGF is the wildtype allele for the nucleic acid sequences encoding EGF, for example they have the wild type allele at position 61 in the EGF 5'UTR. For example, there is an A-allele at nucleic acid site 61 of the EGF gene (SEQ ID NO:1).

In alternative embodiments, the 'negative control' can be a sample comprising the expression level of EGF of a normal (e.g. healthy negative control), which can be compared with the test sample for the subject to assess if there is a measurable difference or substantially no difference as compared with the level of EGF expression in the control group.

In some embodiments of the invention, it can also be useful to compare the gene expression in a test sample to a baseline that has previously been established from a subject or population having susceptibility to cancer, in particular hepatic cellular carcinoma (HCC). Such a baseline level, also referred to herein as a "positive control", refers to EGF gene expression established from one or preferably a population of individuals who have been diagnosed with or having increase risk of developing cancer and whom have a similar nucleic acid sequence of the 5'UTR of the EGF gene. In some embodiments, the positive control can be from the same subject as the test sample. For example, the positive control sample and test sample can be from the same subject wherein the control and test sample was taken at different time points. Such positive controls can be used, for example, to assess the change in the levels of EGF gene product or protein expression in a subject from the first sample taken to a second sample taken. Such assessing the levels of EGF gene product or EGF protein are useful to monitor increased likelihood of developing or having cancer from the time the first sample was taken to the time the second sample was taken from the subject, and also, for example useful for monitoring the effect of a therapeutic protocol, regime or treatment on the levels of EGF protein from the time the first and second sample were taken from the subject.

The present invention provides methods and kits for determining a subject's risk for developing cancer and likely response to specific cancer treatment and/or treatment to prevent cancer by determining the subject's genotype at the gene of interest and/or the level of transcription of a gene of interest. Other aspects of the present invention are described below or will be apparent to one of skill in the art in light of the present disclosure.

DEFINITIONS

For convenience, certain terms employed in the entire application (including the specification, examples, and appended claims) are collected here. Unless defined otherwise, all technical and scientific terms used herein have the same meaning as commonly understood by one of ordinary skill in the art to which this invention belongs.

As used herein, certain terms can have the following defined meanings. As used in the specification and claims, the singular form "a," "an" and "the" include plural references unless the context clearly dictates otherwise. For example, the term "a cell" includes a plurality of cells, including mixtures thereof. As used herein, the term "comprising" is intended to mean that the compositions and methods include the recited elements, but not excluding others The term "EGF" used herein refers to gene encoding Epidermal growth factor. The wild-type human EGF molecule is disclosed in Ref Seq. ID No. NM_001963 (SEQ ID NO:1), the entire disclosure is herein incorporated by reference. The term "EGF gene product" refers to the mRNA or protein encoded by the EGF gene and for reference purposes only, corresponds to the sequence of Ref Seq ID No: NP_001954 (SEQ ID NO:2), or variants thereof.

The term "functional derivative" and "mimetic" are used interchangeably herein, and refers to agents or compounds which possess a biological activity (in particular functional biological activity) that is substantially similar to the biological activity of the entity or molecule for which it's a functional derivative of. The term functional derivative is intended to include the fragments, variants, analogues or chemical derivatives of a molecule.

The term "substantially similar", when used to define the biological activity of a derivative or analogue of EGF as compared to the biological activity of the EGF molecule to which it is a derivative or analogue of, means that a particular derivative or analogue differs from the initial EGF in amino acid or nucleic acid sequence, by one or more amino acids or nucleic acids, including substitutions, deletions, or additions, while the net effect results in the functional derivative retaining at least some of the biological activity found in the initial EGF molecule with respect to the biological activity of EGF with respect to activation of the EGF receptor and EGF signaling pathway. Such biological activity can be assessed by one of ordinary skill in the art using the assay as disclosed herein. As such, derivative or analogue of EGF having lesser degrees of structural similarity but a substantially similar or comparable biological activity of the original EGF from which is based with respect to activation of EGF receptor or EGF signaling are considered to be equivalents. Substantially similar derivatives or analogues of EGF will typically have at least about 60%, or at least about 70% or at least about 80% or at least about 90% or at least about 95%, or at least about 100% the biological activity of wild type EGF or EGF signalling as compared to the EGF it is a derivative or analogue of, or at least at least 2-fold, or at least about 3-fold, or at least about a 4-fold, or at least about a 5-fold or at least about a 10-fold, or any increase between 2-fold and 10-fold or greater the biological activity of EGF signaling as compared to the EGF are to be considered a functional derivative or a functional analogue of the EGF they are based on, as can be assayed using the methods as disclosed herein.

The terms "lower", "reduced", "reduction" or "decrease" or "inhibit" are all used herein generally to mean a decrease by a statistically significant amount. However, for avoidance of doubt, "lower", "reduced", "reduction" or "decrease" or "inhibit" means a decrease by at least 10% as compared to a reference level, for example a decrease by at least about 20%, or at least about 30%, or at least about 40%, or at least about 50%, or at least about 60%, or at least about 70%, or at least about 80%, or at least about 90% or up to and including a 100% decrease (i.e. absent level as compared to a reference sample), or any decrease between 10-100% as compared to a reference level.

The terms "increased", "increase" or "enhance" or "higher" are all used herein to generally mean an increase by a statically significant amount; for the avoidance of any doubt, the terms "increased", "increase" or "enhance" or "higher" means an increase of at least 10% as compared to a reference level, for example an increase of at least about 20%, or at least about 30%, or at least about 40%, or at least about 50%, or at least about 60%, or at least about 70%, or at least about 80%, or at least about 90% or up to and including a 100% increase or any increase between 10-100% as compared to a reference level, or at least about a 2-fold, or at least about a 3-fold, or at least about a 4-fold, or at least about a 5-fold or at least about a 10-fold increase, or any increase between 2-fold and 10-fold or greater as compared to a reference level.

As used herein, the term "subject" refers to any living organism which can be administered to the pharmaceutical compositions of the present invention and in which cancer or a proliferative disorder can occur. The term "subject" includes, but is not limited to, humans and non-human primates such as chimpanzees and other apes and monkey species; and non-human animals, such farm animals such as cattle, sheep, pigs, goats and horses, domestic subjects such as dogs and cats, laboratory animals including rodents such as mice, rats and guinea pigs, and the like. The term "non-human animals" and "non-human mammals" are used interchangeably herein includes all vertebrates, e.g., mammals, such as non-human primates, (particularly higher primates), horses, sheep, dog, rodent (e.g. mouse or rat), guinea pig, goat, pig, cat, rabbits, cows, and non-mammals such as chickens, amphibians, reptiles etc. In one embodiment, the subject is human. In another embodiment, the subject is an experimental animal or animal substitute as a disease model. The term does not denote a particular age or sex. Thus, adult and newborn subjects, as well as fetuses, whether male or female, are intended to be covered. The term "subject" is also intended to include living organisms susceptible to conditions or disease states as generally disclosed, but not limited to, throughout this specification. The term subject is further intended to include transgenic species. In another embodiment, the subject is an experimental animal or animal substitute as a disease model.

The term "tissue" is intended to include intact cells, blood, blood preparations such as plasma and serum, bones, joints, muscles, smooth muscles, and organs.

The term "disease" or "disorder" is used interchangeably herein, refers to any alternation in state of the body or of some of the organs, interrupting or disturbing the performance of the functions and/or causing symptoms such as discomfort, dysfunction, distress, or even death to the person afflicted or those in contact with a person. A disease or disorder can also related to a distemper, ailing, ailment, malady, disorder, sickness, illness, complaint, interdisposition, affection. A disease and disorder, includes but is not limited to any condition manifested as one or more physical and/or psychological symptoms for which treatment is desirable, and includes previously and newly identified diseases and other disorders.

The term "cancer" or "malignancy" are used interchangeably herein, refers to diseases that are characterized by uncontrolled, abnormal growth of cells which results in an increase in a particular cell type or increase in a tissue growth or tissue mass. Cancer cells can spread locally or through the bloodstream and lymphatic system to other parts of the body. The term is also intended to include any disease of an organ or tissue in mammals characterized by poorly controlled or uncontrolled multiplication of normal or abnormal cells in that tissue and its effect on the body as a whole. Cancer diseases within the scope of the definition comprise benign neoplasms, dysplasias, hyperplasias as well as neoplasms showing metastatic growth or any other transformations like e.g. leukoplakias which often precede a breakout of cancer.

As used herein, the term "tumor" refers to a mass of transformed cells that are characterized, at least in part, by containing angiogenic vasculature. The transformed cells are characterized by neoplastic uncontrolled cell multiplication which is rapid and continues even after the stimuli that initiated the new growth has ceased. The term "tumor" is used broadly to include the tumor parenchymal cells as well as the supporting stroma, including the angiogenic blood vessels that infiltrate the tumor parenchymal cell mass. Although a tumor generally is a malignant tumor, i.e., a cancer having the ability to metastasize (i.e. a metastatic tumor), a tumor also can be nonmalignant (i.e. non-metastatic tumor). Tumors are hallmarks of cancer, a neoplastic disease the natural course of which is fatal. Cancer cells exhibit the properties of invasion and metastasis and are highly anaplastic.

As used herein, the term "metastases" or "metastatic tumor" refers to a secondary tumor that grows separately elsewhere in the body from the primary tumor and has arisen from detached, transported cells, wherein the primary tumor is a solid tumor. The primary tumor, as used herein, refers to a tumor that originated in the location or organ in which it is present and did not metastasize to that location from another location. As used herein, a "malignant tumor" is one having the properties of invasion and metastasis and showing a high degree of anaplasia. Anaplasia is the reversion of cells to an immature or a less differentiated form, and it occurs in most malignant tumors.

The term "hepatocellular carcinoma", "hepatic cell carcinoma" and "HCC" are used interchangeably herein, refers to a tumor of the liver. Tumors of the liver can be malignant or benign and are the most common primary malignant liver tumor. Risk factors include chronic active hepatitis B, hepatitis C, and cirrhosis of the liver, (for example alcohol etiology). The term "hepatocarcinoma" refers to a malignant tumor derived from hepatocytes.

The term "inflammation" refers to the localized response elicited by injury or destruction of tissues, which serves to destroy, or prevent damage by the offending agent (e.g. chemical or virus) and the insured tissue.

The term "inflammatory disorder" or "inflammatory disease" used interchangeably herein comprise diseases triggered by cellular or non-cellular mediators of the immune system or tissues causing the inflammation of body tissues and subsequently producing an acute or chronic inflammatory condition. Examples for such inflammatory diseases include, for example, liver disease and/or cirrhosis, hypersensitivity reactions of type-IV, for example but not limited to hypersensitivity diseases of the lung including asthma, atopic diseases, allergic rhinitis or conjunctivitis, angioedema of the lids, hereditary angioedema, antireceptor hypersensitivity reactions and autoimmune diseases, Hashimoto's thyroiditis, systemic lupus erythematosus, Goodpasture's syndrome, pemphigus, myasthenia gravis, Grave's and Raynaud's disease, type B insulin-resistant diabetes, rheumatoid arthritis, psoriasis, Crohn's disease, scleroderma, mixed connective tissue disease, polymyositis, sarcoidosis, glomerulonephritis, acute or chronic host versus graft reactions.

The term "liver disease" refers to disorders of the liver and comprise primary and secondary, acute or chronic diseases or injury to the liver which can be acquired or inherited, begin or malignant, and which affect the liver or the body as a whole. Liver diseases comprise for example, but are not limited to disorders of the bilirubin metabolism, jaundice, syndromes of Gilbert's, Crigler-Najjar, Dubin-Johnson and Rotor; intrahepatic cholestasis, hepatomegaly, portal hypertension, ascites, Budd-Chiari syndrome, portal-systemic encephalopathy, fatty liver, steatosis, Reye's syndrome, liver diseases due to alcohol, alcoholic hepatitis or cirrhosis, fibrosis and cirrhosis, fibrosis and cirrhosis of the liver due to inborn errors of metabolism of exogenous substances, storage diseases, syndromes of Gaucher's, Zellewger's, Wilson's disease, acute or chronic hepatitis, chronic active hepatitis, viral hepatitis (including Hepatitis A, Hepatitis B, Hepatitis C, and hepatitis D) and its variants, inflammatory conditions of the liver due to viruses, bacteria, fungi, protozoa, helminthes, drug-induced disorders of the liver, chronic liver diseases like primary sclerosing cholangitis, alpha$_1$-antitrypsin-deficiency, primary biliary cirrhosis, postoperative liver disorders like intrahepatic cholestasis, hepatic granulomas, vascular liver disorders associated with systematic disease, benign or malignant neoplasms of the liver, disturbance of liver metabolism in the new born or prematurely born.

The term "cirrhosis" refers to liver disease characterized by pathological loss of normal microscopic lobular architecture of the liver, fibrosis and nodular regeneration. Liver cirrhosis refers to chronic interstitial inflammation of the liver.

The term "chronic active hepatitis" refers to a form of continuing liver inflammation that results in liver cell death. Causes of chronic active hepatitis include viral infection (including hepatitis D, hepatitis B and hepatitis C) autoimmune diseases, drug ingestion and metabolic causes. Chronic active hepatitis will lead to hepatic failure and death in a small percentage of patients.

As used herein, the term "gene" includes a segment of DNA that contains all the information for the regulated biosynthesis of an RNA product, including promoters, exons, introns, and other untranslated regions that control expression. Those in the art will readily recognize that nucleic acid molecules can be double-stranded molecules and that reference to a particular site on one strand refers, as well, to the corresponding site on a complementary strand. Thus, in defining a polymorphic site, reference to an adenine, a thymine (uridine), a cytosine, or a guanine at a particular site on the plus (sense) strand of a nucleic acid molecule is also intended to include the thymine (uridine), adenine, guanine, or cytosine (respectively) at the corresponding site on a minus (antisense) strand of a complementary strand of a nucleic acid molecule. Thus, reference can be made to either strand and still comprise the same polymorphic site and an oligonucleotide can be designed to hybridize to either strand. Throughout this specification, in identifying a polymorphic site, reference is made to the sense strand, only for the purpose of convenience. As used herein, the term "gene" or "recombinant gene" refers to a nucleic acid molecule comprising an open reading frame and including at least one exon and (optionally) an intron sequence. The term "intron" refers to a DNA sequence present in a given gene which is spliced out during mRNA maturation.

As used herein, the term "nucleic acid" refers to polynucleotides such as deoxyribonucleic acid (DNA), and, where appropriate, ribonucleic acid (RNA). The term should also be understood to include, as equivalents, derivatives, variants and analogs of either RNA or DNA made from nucleotide analogs, and, as applicable to the embodiment being described, single (sense or antisense) and double-stranded polynucleotides. Deoxyribonucleotides include deoxyedenosine, deoxycytidine, deoxyguanosine, and deoxythymidine. For purposes of clarity, when referring herein to a nucleotide of a nucleic acid, which can be DNA or RNA, the terms "adenosine", "cytosine", "guanosine", and "thymidine" are used. It is understood that if the nucleic acid is RNA, a nucleotide having a uracil base is uridine. The term "nucleotide" or nucleic acid as used herein is intended to refer to ribonucleotides, deoxyribonucleotides, acylic derivatives of nucleotides, and functional equivalents thereof, of any phosphorylation state. Functional equivalents of nucleotides are those that act as substrates for a polymerase as, for example, in an amplification method. Functional equivalents of nucleotides are also those that can be formed into a polynucleotide that retains the ability to hybridize in a sequence specific manner to a target polynucleotide. As used herein, the term "polynucleotide" includes nucleotides of any number. A polynucleotide includes a nucleic acid molecule of any number of nucleotides including single-stranded RNA, DNA or complements thereof, double-stranded DNA or RNA, and the like.

The term "polymorphism" refers to the coexistence of more than one form of a gene or portion thereof. A portion of a gene of which there are at least two different forms, i.e., two different nucleotide sequences, is referred to as a "polymorphic region of a gene". A polymorphic region can be a single nucleotide, the identity of which differs in different alleles. A "polymorphic gene" refers to a gene having at least one polymorphic region.

The term "genotype" refers to the specific allelic composition of an entire cell or a certain gene, whereas the term "phenotype" refers to the detectable outward manifestations of a specific genotype.

The term "allele", which is used interchangeably herein with "allelic variant" refers to alternative forms of a gene or portions thereof. Alleles occupy the same locus or position on homologous chromosomes. When a subject has two identical alleles of a gene, the subject is said to be homozygous for the gene or allele. When a subject has two different alleles of a gene, the subject is said to be heterozygous for the gene. Alleles of a specific gene can differ from each other in a single nucleotide, or several nucleotides, and can include substitutions, deletions and insertions of nucleotides. An allele of a gene can also be a form of a gene containing a mutation.

The term "variant", "variance", "mutation" or "polymorphism" are used interchangeably herein and as used herein with respect to nucleic acid sequence refers to a difference in nucleic acid sequence in the population. Polymorphisms are sometimes referred to as "single nucleotide polymorphism" or "SNP" can be synonymous or non-synonymous. Synonymous polymorphisms when present in the coding region typically do not result in an amino acid change. Non-synonymous polymorphism when present in the coding region alter one or more codons resulting in an amino acid replacement in the amino acid chain. Such mutations and polymorphisms can be either heterozygous or homozygous within an individual. Homozygous individuals have identical alleles at one or more corresponding loci on homologous chromosomes. While heterozygous individuals have two different alleles at one or more corresponding loci on homologous chromosomes. A polymorphism is thus said to be "allelic," in that, due to the existence of the polymorphism, some members of a species carry a gene with one sequence (e.g., the original or wild-type "allele"), whereas other members can have an altered sequence (e.g., the variant or, mutant "allele"). In the simplest case, only one mutated variant of the sequence can exist, and the polymorphism is said to be diallelic. For example, if the two alleles at a locus are indistinguishable in their effects on the organism, then the individual is said to be homozygous at the locus under consideration. If the two alleles at a locus are distinguishable because of their differing effects on the organism, then the individual is said to be heterozygous at the locus. In the present application, typographically, alleles are distinguished "+" or "−". Using these symbols, homozygous individuals are +/+, or −/− or two of the same symbol, for example A/A, G/G, T/T and C/C. Heterozygous individuals are +/− or two different symbols, for example A/G, A/T. A/C, G/T etc. The occurrence of alternative mutations can give rise to tri-allelic and tetra-allelic polymorphisms, etc. An allele can be referred to by the nucleotide(s) that comprise the mutation. In some instances a "silent mutation" is a synonymous codon change, or silent SNP is one that does not result in a change of amino acid due to the degeneracy of the genetic code. A substitution that changes a codon coding for one amino acid to a codon coding for a different amino acid (i.e., a non-synonymous codon change) is referred to as a missense mutation. A nonsense mutation results in a type of non-synonymous codon change in which a stop codon is formed, thereby leading to premature termination of a polypeptide chain and a truncated protein. A read-through mutation is another type of non-synonymous codon change that causes the destruction of a stop codon, thereby resulting in an extended polypeptide product. While SNPs can be bi-, tri-, or tetra-allelic, the vast majority of the SNPs are bi-allelic, and are thus often referred to as "bi-allelic markers", or "di-allelic markers".

The terms "EGF polymorphism" as used herein refers to at least one polymorphic site in the polynucleotide or amino acid sequence of EGF gene or gene product. For purposes of the present application, the wild-type polynucleotide encoding the EGF is designated SEQ ID NO: 1 and the wild-type gene product comprising the EGF molecule, is designated amino acid SEQ ID NO: 2. In one embodiment of the present invention, the EGF polymorphism is rs444903 (NCBI).

The term "allele" or "allelic variant of a polymorphic region of the gene of interest" are used interchangeably herein, refers to a region of the gene of interest having one of a plurality of nucleotide sequences found in that region of the gene in other individuals.

The terms "polymorphic site with increased likelihood of developing cancer" includes associating the polymorphism which occurs at a higher allelic frequency or rate in individuals with the disease than individuals without the disease. Correlation of the disease with the polymorphism can be accomplished by bio-statistical methods known in the art, such as for example, by Chi-squared tests or other methods described by L. D. Fisher and G. vanBelle, Biostatistics: A Methodology for the Health Sciences, Wiley-Interscience (New York) 1993.

The term "wild-type allele" refers to an allele of a gene which, when present in two copies in a subject results in a wild-type phenotype. There can be several different wild-type alleles of a specific gene, since certain nucleotide changes in a gene can not affect the phenotype of a subject having two copies of the gene with the nucleotide changes The term "sample" as used herein generally refers to any material containing nucleic acid, either DNA or RNA or amino acids. Generally, such material will be in the form of a blood sample, stool sample, tissue sample, cells, bacteria, histology section, or buccal swab. Samples can be prepared, for example samples can be fresh, fixed, frozen, or embedded in paraffin.

The term "biological sample" as used herein refers to a cell or population of cells or a quantity of tissue or fluid from a subject. Most often, the sample has been removed from a subject, but the term "biological sample" can also refer to cells or tissue analyzed in vivo, i.e. without removal from the subject. Often, a "biological sample" will contain cells from the animal, but the term can also refer to non-cellular biological material, such as non-cellular fractions of blood, saliva, or urine, that can be used to measure gene expression levels. Biological samples include, but are not limited to, tissue biopsies, scrapes (e.g. buccal scrapes), whole blood, plasma, serum, urine, saliva, cell culture, or cerebrospinal fluid. Biological samples also include tissue biopsies, cell culture. A biological sample or tissue sample can refers to a sample of tissue or fluid isolated from an individual, including but not limited to, for example, blood, plasma, serum, tumor biopsy, urine, stool, sputum, spinal fluid, pleural fluid, nipple aspirates, lymph fluid, the external sections of the skin, respiratory, intestinal, and genitourinary tracts, tears, saliva, milk, cells (including but not limited to blood cells), tumors, organs, and also samples of in vitro cell culture constituent. In some embodiments, the sample is from a resection, bronchoscopic biopsy, or core needle biopsy of a primary or metastatic tumor, or a cellblock from pleural fluid. In addition, fine needle aspirate samples are used. Samples can be either paraffin-embedded or frozen tissue. The sample can be obtained by removing a sample of cells from a subject, but can also be accomplished by using previously isolated cells (e.g. isolated by another person), or by performing the methods of the present invention in vivo. Biological sample also refers to a sample of tissue or fluid isolated from an individual, including but not limited to, for example, blood, plasma, serum, tumor biopsy, urine, stool, sputum, spinal fluid, pleural fluid, nipple aspirates, lymph fluid, the external sections of the skin, respiratory, intestinal, and genitourinary tracts, tears, saliva, milk, cells (including but not limited to blood cells), tumors, organs, and also samples of in vitro cell culture constituent. In some embodiments, the biological samples can be prepared, for example biological samples can be fresh, fixed, frozen, or embedded in paraffin.

The term "isolated" as used herein refers to the state of being substantially free of other material such as nucleic acids, proteins, lipids, carbohydrates, or other materials such as cellular debris or growth media with which EGF polynucleotide encoding EGF, primer oligonucleotide, or allele-specific oligonucleotide can be associated. Typically, the term "isolated" is not intended to refer to a complete absence of these materials. Neither is the term "isolated" generally intended to refer to water, buffers, or salts, unless they are present in amounts that substantially interfere with the methods of the present invention.

The term "cells," "host cells" or "recombinant host cells" are terms used interchangeably herein. It is understood that such terms refer not only to the particular subject cell but to the progeny or potential progeny of such a cell. Because certain modifications can occur in succeeding generations due to either mutation or environmental influences, such progeny can not, in fact, be identical to the parent cell, but are still included within the scope of the term as used herein The term "expression" as used herein refers to interchangeably to the expression of a polypeptide or protein or expression of a polynucleotide or expression of a gene. Expression also refers to the expression of pre-translational modified and post-translationally modified proteins, as well as expression of pre-mRNA molecules, alternatively spliced and mature mRNA molecules. Expression of a polynucleotide can be determined, for example, by measuring the production of RNA transcript molecules, for example messenger RNA (mRNA) transcript levels. Expression of a protein or polypeptide can be determined, for example, by immunoassay using an antibody(ies) that bind with the polypeptide.

The term "encode" as it is applied to polynucleotides refers to a polynucleotide which is said to "encode" a polypeptide or protein if, in its native state or when manipulated by methods well known to those skilled in the art, it can be transcribed to produce the RNA which can be translated into an amino acid sequence to generate the polypeptide and/or a fragment thereof. The antisense strand is the complement of such a nucleic acid, and the encoding sequence can be deduced therefrom.

The term "endogenously expressed" or "endogenous expression" refers to the expression of a gene product at normal levels and under normal regulation for that cell type.

The terms "protein", "polypeptide" and "peptide" are used interchangeably herein refer to a gene product.

The term "gene product(s)" as used herein refers to include RNA transcribed from a gene, or a polypeptide encoded by a gene or translated from RNA.

As used herein, the terms "isoform", or "isoforms" or "variant of protein" are used interchangeably herein, refer to specific forms of the same protein, the specific form differing from other forms of the same protein in the sequence of at least one, and frequently more than one, amino acids. Isoforms are proteins produced from the same gene, due to, for example but not limited to, transcription from different promoters, alternative splicing, differential mRNA splicing and/or post-translational modification such as, for example, glycosylation, sumoylation, phosphorylation, truncation and ectodomain shedding.

The term "EGF protein" as used herein is intended to include all isoforms of the EGF protein, which encompasses EGF proteins with amino-acid sequence variations, as well as pre- and post-translationally modified EGF proteins. Any post-translational modification is encompassed, for example but not limited to glycosylation, phosphorylation, sumoylation, truncation and ectodomain shedding etc. The term EGF protein is also intended to encompass all isoforms of EGF, for example truncated forms of EGF, as well as proEGF and mature EGF as well as other EGF isoforms and variants. Isoforms of EGF protein useful in the present invention are fragments of the EGF protein, and include, but is not limited to isoforms of the following sizes; between 140-170 kDa, 97 kDa, between 70-66 kDa, 50 kDa, 42 kDa, 35 kDa, 20 kDa and 6 kDa.

The term "EGF mRNA" as used herein is intended to include all EGF mRNA species or variants and all post-transcription RNA products, for example mRNA products transcribed from the EGF gene, such as but not limited to pre-mRNA and mature mRNA molecules. For example, the EGF gene is transcribed into what is commonly referred to in the art as "preproEGF mRNA", which is included in the term EGF mRNA. Also encompassed in the term EGF mRNA is pre-mRNA, mature mRNA molecules and alternatively spliced mRNA molecules of EGF.

The term "recombinant protein" refers to a polypeptide which is produced by recombinant DNA techniques, wherein generally, DNA encoding the polypeptide is inserted into a suitable expression vector which is in turn used to transform a host cell to produce the heterologous protein.

The term "immunohistochemistry" or "IHC" or "immunochemistry" refer to the family of techniques based on the use of a specific antibody, wherein antibodies are used to specifically target molecules inside or on the surface of cells. The antibody typically contains a marker that will undergo a biochemical reaction, and thereby experience a change color, upon encountering the targeted molecules. In some instances, signal amplification can be integrated into the particular protocol, wherein a secondary antibody, that includes the marker stain, follows the application of a primary specific antibody.

The term "antigen" is well understood in the art and includes substances which are immunogenic. For example, EGF and EGF receptor (EGFR) are both antigens. A "native" or "natural" or "wild-type" antigen, when used in the context of an antigen, is a polypeptide, protein or a fragment which contains an epitope and which has been isolated from a natural biological source. It also can specifically bind to an antigen receptor.

As used herein, an "antibody" includes whole antibodies and any antigen binding fragment or a single chain thereof. Thus the term "antibody" includes any protein or peptide containing molecule that comprises at least a portion of an immunoglobulin molecule. Examples of such include, but are not limited to a complimentarily determining region (CDR) of a heavy or light chain or a ligand binding portion thereof, a heavy chain or light chain variable region, a heavy chain or light chain constant region, a framework (FR) region, or any portion thereof, or at least one portion of a binding protein, any of which can be incorporated into an antibody of the present invention. The antibodies can be polyclonal or monoclonal and can be isolated from any suitable biological source, e.g., murine, rat, sheep and canine. Additional sources are identified infra. The term "antibody" is further intended to encompass digestion fragments, specified portions, derivatives and variants thereof, including antibody mimetics or comprising portions of antibodies that mimic the; structure and/or function of an antibody or specified fragment or portion thereof, including single chain antibodies and fragments thereof. Examples of binding fragments encompassed within the term "antigen binding portion" of an antibody include a Fab fragment, a monovalent fragment consisting of the VL, VH, CL and CH, domains; a F(ab') 2 fragment, a bivalent fragment comprising two Fab fragments linked by a disulfide bridge at the hinge region; a Ed fragment consisting of the VH and CH, domains; a Fv fragment consisting of the VL and VH domains of a single arm of an antibody, a dAb fragment (Ward et al. (1989) Nature 341:544-546), which consists of a VH domain; and an isolated complimentarily determining region (CDR). Furthermore, although the two domains of the Fv fragment, VL and VH, are coded for by separate genes, they can be joined, using recombinant methods, by a synthetic linker that enables them to be made as a single protein chain in which the VL and VH regions pair to form monovalent molecules (known as single chain Fv (scFv)). Bird et al. (1988) Science 242:423-426 and Huston et al. (1988) Proc. Natl. Acad Sci. USA 85:5879-5883. Single chain antibodies are also intended to be encompassed within the term "fragment of an antibody." Any of the above-noted antibody fragments are obtained using conventional techniques known to those of skill in the art, and the fragments are screened for binding specificity and neutralization activity in the same manner as are intact antibodies.

The term "epitope" means a protein determinant capable of specific binding to an antibody. Epitopes usually consist of chemically active surface groupings of molecules such as amino acids or sugar side chains and usually have specific three dimensional structural characteristics, as well as specific charge characteristics. Conformational and non-conformational epitopes are distinguished in that the binding to the former but not the latter is lost in the presence of denaturing solvents.

The term "antibody variant" is intended to include antibodies produced in a species other than a mouse. It also includes antibodies containing post translational modifications to the linear polypeptide sequence of the antibody or fragment. It further encompasses fully human antibodies. The term "antibody derivative" is intended to encompass molecules that bind an epitope as defined above and which are modifications or derivatives of a native monoclonal antibody of this invention. Derivatives include, but are not limited to, for example, bispecific, multispecific, heterospecific, trispecific, tetraspecific, multispecific antibodies, diabodies; chimeric, recombinant and humanized.

The term "bispecific molecule" is intended to include any agent, e. g., a protein, peptide, or protein or peptide complex, which has two different binding specificities. The term "multispecific molecule" or "heterospecific molecule" is intended to include any agent, e.g. a protein, peptide, or protein or peptide complex, which has more than two different binding specificities.

The term "heteroantibodies" refers to two or more antibodies, antibody binding fragments (e.g., Fab), derivatives thereof, or antigen binding regions linked together, at least two of which have different specificities.

The term "human antibody" as used herein, is intended to include antibodies having variable and constant regions derived from human germline immunoglobulin sequences. The human antibodies of the present invention can include amino acid residues not encoded by human germline immunoglobulin sequences (e.g., mutations introduced by random or site-specific mutagenesis in vitro or by somatic mutation in viva). However, the term "human antibody" as used herein, is not intended to include antibodies in which CDR sequences derived from the germline of another mammalian species, such as a mouse, have been grafted onto human framework sequences. Thus, as used herein, the term "human antibody" refers to an antibody in which substantially every part of the protein (e. g., CDR, framework, CL, CH domains (e.g., CH1, CH2, CH3), hinge, (Via, VH)) is substantially non-immunogenic in humans, with only minor sequence changes or variations. Similarly, antibodies designated primate (monkey, baboon, chimpanzee, etc.), rodent (mouse, rat, rabbit, guinea pig, hamster, and the like) and other mammals designate such species, sub-genus, genus, sub-family, family specific antibodies. Further, chimeric antibodies include any combination of the above. Such changes or variations optionally and preferably retain or reduce the immunogenicity in humans or other species relative to non-modified antibodies. Thus, a human antibody is distinct from a chimeric or humanized antibody. It is pointed out that a human antibody can be produced by a non-human animal or prokaryotic or eukaryotic cell that is capable of expressing functionally rearranged human immunoglobulin (e.g., heavy chain and/or light chain); genes. Further, when a human antibody is a single chain antibody, it can comprise a linker peptide that is not found in native human antibodies. For example, an Fv can comprise a linker peptide, such as two to about eight glycine or other amino acid residues, which connects the variable region of the heavy chain and the variable region of the light chain. Such linker peptides are considered to be of human origin.

As used herein, a human antibody is "derived from" a particular germline sequence if the antibody is obtained from a system using human immunoglobulin sequences, e.g., by immunizing a transgenic mouse carrying human immunoglobulin genes or by screening a human immunoglobulin gene library. A human antibody that is "derived from" a human germline immunoglobulin sequence can be identified as such by comparing the amino acid sequence of the human antibody to the amino acid sequence of human germline immunoglobulins. A selected human antibody typically is at least 90% identical in amino acids sequence to an amino acid sequence encoded by a human germline immunoglobulin gene and contains amino acid residues that identify the human antibody as being human when compared to the germline immunoglobulin amino acid sequences of other species (e.g., murine germline sequences). In certain cases, a human antibody can be at least about 95%, or even at least about 96%, or least about 97%, or least about 98%, or least about 99% identical in amino acid sequence to the amino acid sequence encoded by the germline immunoglobulin gene. Typically, a human antibody derived from a particular human germline sequence will display no more than 10 amino acid differences from the amino acid sequence encoded by the human germline immunoglobulin gene. In certain cases, the human antibody can display no more than 5, or even no more than 4, 3, 2, or 1 amino acid difference from the amino acid sequence encoded by the germline immunoglobulin gene.

The terms "monoclonal antibody" or "monoclonal antibody composition" as used herein refer to a preparation of antibody molecules of single molecular composition. A monoclonal antibody composition displays a single binding specificity and affinity for a particular epitope.

The term "human monoclonal antibody" refers to antibodies displaying a single binding specificity which have variable and constant regions derived from human germline immunoglobulin sequences. The term "recombinant human antibody", as used herein, includes all human antibodies that are prepared, expressed, created or isolated by recombinant means, such as antibodies isolated from an animal (e.g., a mouse) that is transgenic or transchromosomal for human immunoglobulin genes or a hybridoma prepared therefrom, antibodies isolated from a host cell transformed to express the antibody, e.g., from a transfectoma, antibodies isolated from a recombinant, combinatorial human antibody library, and antibodies prepared, expressed, created or isolated by any other means that involve splicing of human immunoglobulin gene sequences to other DNA sequences. Such recombinant human antibodies have variable and constant regions derived from human germline immunoglobulin sequences. In certain embodiments, however, such recombinant human antibodies can be subjected to in vitro mutagenesis (or, when an animal transgenic for human Ig sequences is used, in viva somatic mutagenesis) and thus the amino acid sequences of the VH and VL regions of the recombinant antibodies are sequences that, while derived from and related to human germline VH and VL sequences, can not naturally exist within the human antibody germline repertoire in vivo. As used herein, "isotype" refers to the antibody class (e. g., IgM or IgG1) that is encoded by heavy chain constant region genes.

The terms "oligonucleotide" or "polynucleotide", or "portion," or "segment" thereof refer to a stretch of polynucleotide residues which is long enough to use in PCR or various hybridization procedures to identify or amplify identical or related parts of mRNA or DNA molecules. The polynucleotide compositions of this invention include RNA, cDNA, genomic DNA, synthetic forms, and mixed polymers, both sense and antisense strands, and can be chemically or biochemically modified or can contain! non-natural or derivatized nucleotide bases, as will be readily appreciated by those skilled in the art. Such modifications include, for example, labels, methylation, substitution of one or more of the naturally occurring nucleotides with an analog, internucleotide modifications such as uncharged linkages (e.g., methyl phosphonates, phosphotriesters, phosphoamidates, carbamates, etc.), charged linkages (e. g., phosphorothioates, phosphorodithioates, etc.); pendent moieties (e.g., polypeptides), intercalators (e.g., acridine, psoralen, etc.), chelators, alkylators, and modified linkages (e.g., alpha anomeric nucleic acids, etc.). Also included are synthetic molecules that mimic polynucleotides in their ability to bind to a designated sequence via hydrogen bonding and other chemical interactions. Such molecules are known in the art and include, for example, those in which peptide linkages substitute for phosphate linkages in the backbone of the molecule. The term "oligonucleotide" as used herein includes a polynucleotide molecule comprising any number of nucleotides which has sufficient number of bases to be used as an oligomer, aptimer or probe in a polymerase chain reaction (PCR). Oligonucleotides are prepared from genomic or cDNA sequence and used to amplify, reveal and confirm the presence of similar DNA or RNA in a particular cell or tissue. Oligonucleotides or oligomers comprise portions of a DNA sequence having at least about 10 nucleotides and as many as about 35 nucleotides and preferably, less than about 200 nucleotides. Oligonucleotides can be between about 5 and about 100 nucleotides in length, preferably between at least about 10 to about 50 nucleotides in length. The exact length of a particular oligonucleotide, however, will depend on many factors, which in turn depend on the ultimate function or use of the oligonucleotide. Oligonucleotides can be synthesized chemically by any suitable means known in the art or derived from a biological sample, as for example, by restriction digestion. The source of the oligonucleotides is not essential to the present invention. Oligonucleotides can be labeled, according to any technique known in the art, such as with radiolabels, fluorescent labels, enzymatic labels, proteins, haptens, antibodies, sequence tags, mass tags, fluorescent polarization etc.

The term "primer", as used herein, refers to an oligonucleotide which is capable of acting as a point of initiation of polynucleotide synthesis along a complementary strand when placed under conditions in which synthesis of a primer extension product which is complementary to a polynucleotide is catalyzed. Such conditions include the presence of four different nucleotide triphosphates or nucleoside analogs and one or more agents for polymerization such as DNA polymerase and/or reverse transcriptase, in an appropriate buffer ("buffer" includes substituents which are cofactors, or which affect pH, ionic strength, etc.), and at a suitable temperature, A primer must be sufficiently long to prime the synthesis of extension products in the presence of an agent for polymerase. A typical primer contains at least about 5 nucleotides in length of a sequence substantially complementary to the target sequence, but somewhat longer primers are preferred. Usually primers contain about 15-26 nucleotides, but longer primers can also be employed. Oligonucleotides, such as "primer" oligonucleotides are preferably single stranded, but can alternatively be double stranded. If double stranded, the oligonucleotide is generally first treated to separate its strands before being used for hybridization purposes or being used to prepare extension products. Primer oligonucleotides can be oligodeoxyribonucleotide. A primer will always contain a sequence substantially complementary to the target sequence which is the specific sequence to be amplified, to which it can anneal, A primer may, optionally, also comprise a promoter sequence.

In the context of this invention, the term "probe" refers to a molecule which can detectably distinguish between target molecules differing in structure. Detection can be accomplished in a variety of different ways depending on the type of probe used and the type of target molecule, thus, for example, detection can be based on discrimination of activity levels of the target molecule, but preferably is based on detection of specific binding. Examples of such specific binding include antibody binding and nucleic acid probe hybridization. Thus, for example, probes can include enzyme substrates, antibodies and antibody fragments, and preferably nucleic acid hybridization probes, for example DNA, RNA, PNA, pseudo-complementary PNA (pcPNA), locked nucleic acid (LNA) and nucleic acid analogues thereof.

Oligonucleotides can be used as "probes", and refer to such as genomic DNA, mRNA, or other suitable sources of nucleic acid oligonucleotides. For such purposes, the oligonucleotides must be capable of specifically hybridizing to a target polynucleotide or DNA nucleic acid molecule. As used herein, two nucleic acid molecules are said to be capable of specifically hybridizing to one another if the two molecules are capable of forming an anti-parallel, double-stranded nucleic acid structure under hybridizing conditions.

The term "allele-specific oligonucleotide" refers to an oligonucleotide that is able to hybridize to a region of a target polynucleotide spanning the sequence, mutation, or polymorphism being detected and is substantially unable to hybridize to a corresponding region of a target polynucleotide that either does not contain the sequence, mutation, or polymorphism being detected or contains an altered sequence, mutation, or polymorphism. As will be appreciated by those in the art, allele-specific is not meant to denote an absolute condition. Allele-specificity will depend upon a variety of environmental conditions, including salt and formamide concentrations, hybridization and washing conditions and stringency. Depending on the sequences being analyzed, one or more allele-specific oligonucleotides can be employed for each target polynucleotide. Preferably, allele-specific oligonucleotides will be completely complementary to the target polynucleotide. However, departures from complete complementarity are permissible. In order for an oligonucleotide to serve as a primer oligonucleotide, however, it typically need only be sufficiently complementary in sequence to be able to form a stable double-stranded structure under the particular environmental conditions employed. Establishing environmental conditions typically involves selection of solvent and salt concentration, incubation temperatures, and incubation times.

The term "hybridizing" as used herein, refers to the binding of one nucleic acid sequence to another by complementation or complementary base pair matching.

A nucleic acid molecule is said to be the "complement" of another nucleic acid molecule if it exhibits complete complementarity. As used herein, molecules are said to exhibit "complete complementarity" when every nucleotide of one of the molecules is complementary to a nucleotide of the other. Two molecules are said to be "substantially complementary" if they can hybridize to one another with sufficient stability to permit them to remain annealed to one another under at least conventional "low-stringency" conditions. Similarly, the molecules are said to be "complementary" if they can hybridize to one another with sufficient stability to permit them to remain annealed to one another under conventional "high-stringency" conditions. Conventional stringency conditions are described, for example, by Sambrook, J., et al, in Molecular Cloning, a Laboratory Manual, 2nd Edition, Cold Spring Harbor Press, Cold Spring Harbor, N.Y. (1989), and by Haymes, B. D., et al. in Nucleic Acid Hybridization, A Practical Approach, IRL Press, Washington, D.C. (1985), both herein incorporated by reference). Departures from complete complementarity are therefore permissible, as long as such departures do not completely preclude the capacity of the molecules to form a double-stranded structure. For example, a non-complementary nucleotide fragment can be attached to the 5' end of the primer, with the remainder of the primer sequence being complementary to the strand. Alternatively, non-complementary bases or longer sequences can be interspersed into the primer, provided that the primer sequence has sufficient complementarity with the sequence of the strand to hybridize therewith for the purposes employed. However, for detection purposes, particularly using labeled sequence-specific probes, the primers typically have exact complementarity to obtain the best results. Thus, for an oligonucleotide to serve as an allele-specific oligonucleotide, it must generally be complementary in sequence and be able to form a stable double-stranded structure with a target polynucleotide under the particular environmental conditions employed.

The term "real-time quantitative RT-PCR" or "quantitative RT-PCR" or "QRT-PCR" are used interchangeably herein, refers to reverse transcription (RT) polymerase chain reaction (PCR) which enables detection of gene transcription. The method is known to those ordinary skilled in the art and comprises of the reverse transcription and amplification of messenger RNA (mRNA) species to cDNA, which is further amplified by the PCR reaction. QRT-PCR enables a one skilled in the art to quantitatively measure the level of gene transcription from the test gene in a particular biological sample. The methods of RNA isolation, RNA reverse transcription (RT) to cDNA (copy DNA) and cDNA or nucleic acid amplification and analysis are routine for one skilled in the art and examples of protocols can be found, for example, in the Molecular Cloning: A Laboratory Manual (3-Volume Set) Ed. Joseph Sambrook, David W. Russel, and Joe Sambrook, Cold Spring Harbor Laboratory; 3rd edition (Jan. 15, 2001), ISBN: 0879695773. Particularly useful protocol source for methods used in PCR amplification is PCR (Basics: From Background to Bench) by M. J. McPherson, S. G. Møller, R. Beynon, C. Howe, Springer Verlag; 1st edition (Oct. 15, 2000), ISBN: 0387916008.

The term "multiplex" as used herein refers to the testing and/or the assessment of more than one gene within the same reaction sample.

The term "amplify" is used in the broad sense to mean creating an amplification product which can include, for example, additional target molecules, or target-like molecules or molecules complementary to the target molecule, which molecules are created by virtue of the presence of the target molecule in the sample. In the situation where the target is a nucleic acid, an amplification product can be made enzymatically with DNA or RNA polymerases or reverse transcriptases. The term "amplification of polynucleotides" includes methods such as PCR, ligation amplification (or ligase chain reaction, LCR) and amplification methods. These methods are known and widely practiced in the art. See, e.g., U.S. Pat. Nos. 4,683,195 and 4,683,202 and Innis et al., 1990 (for PCR); and Wu, D. Y. et al. (1989) Genomics 4:560-569 (for LCR).

The term "Homology" or "identity" or "similarity" refers to sequence similarity between two peptides or between two nucleic acid molecules. Homology can be determined by comparing a position in each sequence which can be aligned for purposes of comparison. When a position in the compared sequence is occupied by the same base or amino acid, then the molecules are homologous at that position. A degree of homology between sequences is a function of the number of matching or homologous positions shared by the sequences. An "unrelated" or "non-homologous" sequence shares less than about 40% identity, though preferably less than about 25% identity, with one of the sequences of the present invention.

The term "a homolog of a nucleic acid" refers to a nucleic acid having a nucleotide sequence having a certain degree of homology with the nucleotide sequence of the nucleic acid or complement thereof. A homolog of a double stranded nucleic acid is intended to include nucleic acids having a nucleotide sequence which has a certain degree of homology with or with the complement thereof. In one aspect, homologs of nucleic acids are capable of hybridizing to the nucleic acid or complement thereof.

The term "interact" as used herein is meant to include detectable interactions between molecules, such as can be detected using, for example, e. hybridization assay. The term interact is also meant to include "binding" interactions between molecules. Interactions can be, for example, protein-protein, protein-nucleic acid, protein-small molecule or small molecule-nucleic acid in nature.

The term "isolated" as used herein with respect to nucleic acids, such as DNA or RNA, refers to molecules separated from other DNAs or RNAs, respectively that are present in the natural source of the macromolecule. The term isolated as used herein also refers to a nucleic acid or peptide that is substantially free of cellular material, viral material, or culture medium when produced by recombinant DNA techniques, or chemical precursors or other chemicals when chemically synthesized. Moreover, an "isolated nucleic acid" is meant to include nucleic acid fragments which are not naturally occurring as fragments and would not be found in the natural state. The term "isolated" is also used herein to refer to, polypeptides which are isolated from other cellular proteins and is meant to encompass both purified and recombinant polypeptides.

The term "mismatches" refers to hybridized nucleic acid duplexes which are not 100% homologous. The lack of total homology can be due to deletions, insertions, inversions, substitutions or frame shift mutations.

As used herein, the terms "treat" or "treatment" or "treating" refers to both therapeutic treatment and prophylactic or preventative measures, wherein the object is to prevent or slow the development of the disease, such as slow down the development of a tumor, the spread of cancer, or to reduce at least one effect or symptom of the condition, disease or disorder associated with inappropriate proliferation or a cell mass, for example cancer. For example, in the case of cancer, treatment can be, for example a reduction in cachexia. Evidence of treatment can be clinical or sub-clinical. Treatment is generally "effective" if one or more symptoms or clinical markers are reduced as that term is defined herein. Alternatively, treatment is "effective" if the progression of a disease is reduced or halted. That is, "treatment" includes not just the improvement of symptoms or markers, but also a cessation of at least slowing of progress or worsening of symptoms that would be expected in absence of treatment. Beneficial or desired clinical results include, but are not limited to, alleviation of one or more symptom(s), diminishment of extent of disease, stabilized (i.e., not worsening) state of disease, delay or slowing of disease progression, amelioration or palliation of the disease state, and remission (whether partial or total), whether detectable or undetectable. "Treatment" can also mean prolonging survival as compared to expected survival if not receiving treatment. Those in need of treatment include those already diagnosed with cancer, as well as those likely to develop secondary tumors due to metastasis.

The term "effective amount" as used herein refers to the amount of therapeutic agent of an anti-cancer therapy as disclosed herein, to alleviate at least one or more symptom of the disease or disorder, and relates to a sufficient amount of pharmacological composition to provide the desired effect. The phrase "therapeutically effective amount" as used herein, e.g., a pharmaceutical composition comprising at least one anti-cancer therapy as disclosed herein means a sufficient amount of the composition to treat a disorder, at a reasonable benefit/risk ratio applicable to any medical treatment. The term "therapeutically effective amount" therefore refers to an amount of the composition as disclosed herein that is sufficient to effect a therapeutically or prophylactically significant reduction in a symptom or clinical marker associated with a cancer or a cancer-mediated condition.

A therapeutically or prophylactically significant reduction in a symptom is, e.g. at least about 10%, at least about 20%, at least about 30%, at least about 40%, at least about 50%, at least about 60%, at least about 70%, at least about 80%, at least about 90%, at least about 100%, at least about 125%, at least about 150% or more in a measured parameter as compared to a control or non-treated subject. Measured or measurable parameters include clinically detectable markers of disease, for example, elevated or depressed levels of a biological marker, as well as parameters related to a clinically accepted scale of symptoms or markers for a disease or disorder. It will be understood, however, that the total daily usage of the compositions and formulations as disclosed herein will be decided by the attending physician within the scope of sound medical judgment. The exact amount required will vary depending on factors such as the type of disease being treated.

With reference to the treatment of a subject with a cancer with a pharmaceutical composition comprising an anti-cancer therapy as disclosed herein, the term "therapeutically effective amount" refers to the amount that is safe and sufficient to prevent or delay the development or growth of a tumor or the spread of a metastases in a subjects identified to be at risk of developing cancer, such as HCC by the methods as disclosed herein. The amount can prevent the cancer from developing, or cause the cancer to go into remission, or slow the course of cancer progression, or slow or inhibit the development of a tumor growth, or slow or inhibit tumor metastasis, or slow or inhibit the establishment of secondary tumors at metastatic sites, or inhibit the formation of new tumor metastases. The effective amount for the treatment of cancer depends on the tumor to be treated, the severity of the tumor, the drug resistance level of the tumor, the species being treated, the age and general condition of the subject, the mode of administration and so forth. Thus, it is not possible to specify the exact "effective amount". However, for any given case, an appropriate "effective amount" can be determined by one of ordinary skill in the art using only routine experimentation. The efficacy of treatment can be judged by an ordinarily skilled practitioner, for example, efficacy can be assessed in animal models of cancer and tumor, for example treatment of a rodent with a cancer, and any treatment or administration of the compositions or formulations that leads to a decrease of at least one symptom of the cancer, for example a reduction in the size of the tumor or a slowing or cessation of the rate of growth of the tumor indicates effective treatment. In embodiments where the compositions are used for the treatment of cancer, the efficacy of the composition can be judged using an experimental animal model of cancer, e.g., wild-type mice or rats, or preferably, transplantation of tumor cells. When using an experimental animal model, efficacy of treatment is evidenced when a reduction in a symptom of the cancer, for example a reduction in the size of the tumor or a slowing or cessation of the rate of growth of the tumor occurs earlier in treated, versus untreated animals. By "earlier" is meant that a decrease, for example in the size of the tumor occurs at least 5% earlier, but preferably more, e.g., one day earlier, two days earlier, 3 days earlier, or more.

As used herein, the term "treating" when used in reference to a cancer treatment is used to refer to the reduction of a symptom and/or a biochemical marker of cancer, such as HCC, for example a reduction in at least one biochemical marker of cancer by at least about 10% would be considered an effective treatment. In some embodiments, the reduction is a reduction in EGF protein or EGF mRNA in the cancer or tumor, such as EGF. Examples of other biochemical markers of cancer include, for example but are not limited to, CD44, telomerase, TGF-α, TGF-β, erbB-2, erbB-3, MUC1, MUC2, CK20, PSA, CA125 and FOBT. A prevention of the development of cancer, such as the prevention of the development HCC in a subject with an inflammatory disease such as cirrhosis would be considered an effective treatment. Alternatively, a reduction by at least about 10% in the rate of development of cancer, such as HCC in a subject with an inflammatory disease such as cirrhosis, would also be considered effective treatment by the methods as disclosed herein. Alternatively, a reduction in the rate of proliferation of the cancer cells by at least about 10% would also be considered effective treatment by the methods as disclosed herein. As alternative examples, a reduction in a symptom of cancer, for example, a slowing of the rate of growth of the cancer by at least about 10% or a cessation of the increase in tumor size, or a reduction in the size of a tumor by at least about 10% or a reduction in the tumor spread (i.e. tumor metastasis) by at least about 10% would also be considered as affective treatments by the methods as disclosed herein. In some embodiments, it is preferred, but not required that the therapeutic agent actually kill the tumor.

The term "effective amount" as used herein refers to the amount of therapeutic agent of pharmaceutical composition to alleviate at least some of the symptoms of the disease or disorder.

The term "agent" or "compound" as used herein and throughout the application is intended to refer to any entity or means such as an organic or inorganic molecule, including but not limited to, small molecules, compounds, modified and unmodified nucleic acids such as antisense nucleic acids, RNAi, such as siRNA or shRNA, peptides, peptidomimetics, receptors, ligands, and antibodies, aptamers, polypeptides, nucleic acid analogues or variants thereof.

The articles "a" and "an" are used herein to refer to one or to more than one (i.e., to at least one) of the grammatical object of the article. By way of example, "an element" means one element or more than one element.

Other than in the operating examples, or where otherwise indicated, all numbers expressing quantities of ingredients or reaction conditions used herein should be understood as modified in all instances by the term "about." The term "about" when used in connection with percentages can mean±1%. The present invention is further explained in detail by the following examples, but the scope of the present invention should not be limited thereto.

It should be understood that this invention is not limited to the particular methodology, protocols, and reagents, etc., described herein and as such can vary. The terminology used herein is for the purpose of describing particular embodiments only, and is not intended to limit the scope of the present invention, which is defined solely by the claims.

Screening a Subject for a Risk of Developing Cancer

The present invention features diagnostic and prognostic methods, which are based, at least in part, on determination of the identity of the polymorphic region and/or expression level (separately, sequentially in any order or together at the same time) of the EGF gene. For example, information obtained using the diagnostic assays described herein is useful for determining if a subject with an inflammatory disorders likely to develop cancer. In certain embodiments, the inflammatory disease is liver disease and/or cirrhosis. In some embodiments, the cancer is hepatocellular carcinoma (HCC). The methods of the present invention relate to determining the expression and/or polymorphisms in EGF. Based on the prognostic information, a clinician can recommend a regimen (for example, increased screening, surveillance and monitoring) or therapeutic protocol (for example prophylactic therapies and preventative therapies), useful in preventing or reducing the risk of developing cancer in the subject.

In one embodiment of the present invention are methods of determining the risk a subject has for developing cancer. In another embodiment, the cancer is hepatic cell carcinoma (HCC) in subjects with liver disease. The present invention can be used to diagnose or prognose an individual with liver disease in developing cancer. In one embodiment, the method comprises determining the level of EGF gene product expression in a biological sample. The level of EGF gene product expression can be level of EGF nucleic acid expression or EGF protein expression. In some embodiments, the EGF protein is an isoform of EGF protein, as disclosed herein, and in some embodiments, the level of more than one isoform of EGF protein is measured.

In one embodiment, the method comprises determining the presence of polymorphisms in the EGF gene. For example, a polymorphic site in the gene encoding the EGF (SEQ ID NO: 1) for example, at nucleotide position 61 can be detected. In some embodiments, the A- or G-allele at nucleotide position 61 in the EGF gene can be detected. Thus, the variance of the EGF gene wherein a substitution of one nucleotide, for example variance 61A>G of SEQ ID NO:1, when compared to the nucleotide sequence encoding the wild-type EGF gene (RefSeq ID: NM_001963) (SEQ ID NO:1) is encompassed in the present invention. A subject identified as having such a polymorphism, for example 61A>G in the EGF gene, is identified as having an increased risk for developing a disease, or can be used to determine a diagnosis or prognosis for the disease.

In addition, knowledge of the identity of a particular allele (i.e. the genetic profile) in a subject allows prioritization and customization of therapy in subjects with liver disease, enabling matching the subject's genetic profile to a particular therapy, regime or monitoring frequency which is one of the goals of "pharmacogenomics". For example, the present invention provides methods to match a subject's genetic profile, i.e. if a subject is identified using the methods of the present invention as having increased risk of developing cancer, for example hepatic cell carcinoma (HCC), the clinician can monitor the therapeutic regime accordingly, for example: 1) increase frequency of screening to monitor for cancer; 2) identify populations of subjects at high risk of developing cancer; 3) more effectively prescribe prophylactic therapies and/or agents that will prevent the development of cancer; 4) to better recommend appropriate therapeutic intervention including dosage of a particular drug, anti-cancer therapy and/or lifestyle change. Further, the expression profile of subjects can be compared before and after to monitor efficacy of an appropriate drug and dose to administered to the subject.

Further, the ability to identify populations of subjects at high risk of developing cancers enables prioritization of subjects with highest clinical benefit, based on the normal or disease genetic profile, and can enable: 1) monitoring efficacy of therapeutic interventions targeting the EGF and/or EFG pathway; 2) possible repositioning of marketed drugs with disappointing market results; 3) the rescue of drug candidates whose clinical development has been discontinued as a result of safety or efficacy limitations, which are patient subgroup-specific; and 4) an accelerated and less costly development for drug candidates and more optimal drug labeling.

The method of this invention relates to nucleic acid molecules containing polymorphisms, methods and reagents for the detection of the changes in the wildtype sequence of EGF 5'UTR, uses of these polymorphisms for the development of detection reagents, and assays or kits that utilize such reagents. In one embodiment, the SNP in EGF 5'UTR as described herein are useful for diagnosing, screening for, and evaluating predisposition and prognosis of risk of developing cancer and related pathologies in humans. Furthermore, these mutations are therefore useful for assessing the likelihood of a subject with an inflammatory disorder, for example liver disease and/or cirrhosis of developing hepatocellular carcinoma. Therefore an appropriate treatment regime can be implicated, for example administration of a prophylactic therapy to reduce the chance of cancer and/or change of lifestyle/exercise routine. In some embodiments, one begins treatment as soon as possible.

Accordingly, the method of this invention also encompass that, if a subject is identified as to being likely to have increased risk of developing cancer, in particular hepatocellular carcinoma, for example subjects with the G-allele at position 61 in the EGF gene are administered an effective amount of an anti-cancer therapy, or chemopreventative therapy. In some embodiments, the anti-cancer therapy is a therapy that suppresses the activity of the EGF-EGFR pathway, for example antibodies which block the action of EGF on the EGR receptor, for example, ERBITUX® (Cetuximab, ImClone), a monoclonal antibody against EGFR, is approved for treatment of colon carcinomas. IRESSA® (Gefitinib, AstraZeneca) and TARCEVA® (Erlonitib, Genentech) are small molecule kinase inhibitors of EGFR that are approved for treating non-small cell lung cancer (NSCLC) patients.

Detection of nucleic acids encoding EGF, as well as nucleic acids involved in the expression or stability of EGF polypeptides or transcripts are also encompassed by the invention. General methods of nucleic acid detection are provided below, followed by specific examples employed for the identification of polymorphisms, including single nucleotide polymorphisms (SNPs).

In one embodiment, the tissue is the tumor tissue itself or normal tissue immediately adjacent to the tumor. In yet a further embodiment when the subject is being assayed for a genetic polymorphism, any cell expected to carry the gene of interest can be used, for example but not limited to peripheral blood lymphocytes, any other suitable cell or tissue sample, or biological sample, including serum, blood, liver etc obtained from the subject.

Sample nucleic acid for use in the diagnostic and prognostic methods can be obtained from any cell type or tissue of a subject, if the sample nucleic acid is genomic DNA. If the sample nucleic acid is mRNA, the sample must be obtained from the cell type or tissues of a subject in which the mRNA is expressed. Similarity, if EGF protein or peptide is to be detected, the sample must be obtained from the cell type or tissue in which EGF expression is located, either expressed within the cell type or tissue, or translocated to the cell type or tissue.

For example, a subject's bodily fluid (e.g. blood) can be obtained by known techniques (e.g., venipuncture). Alternatively, nucleic acid tests can be performed on dry samples (e.g., hair or skin). Fetal nucleic acid samples can be obtained from maternal blood as described in International Patent Application No. WO91/07660 to Bianchi.

Diagnostic procedures can also be performed in situ directly upon tissue sections (fixed and/or frozen) of patient tissue obtained from biopsies or resections, such that no nucleic acid purification is necessary. Nucleic acid reagents can be used as probes and/or primers for such in situ procedures (see, for example, Nuovo, G. J. (1992) "PCR In Situ Hybridization: Protocols And Applications", Raven Press, NY).

Detection of Expression Level of EGF Gene Product

In some embodiments, the present invention related to the measurement of the level of the EGF gene product in a biological sample from a subject. In some embodiment, the EGF gene product is the EGF protein and isoforms of EGF and in alternative embodiments, the EGF gene product is RNA transcribed from the EGF gene, for example EGF mRNA.

In one embodiment where EGF gene expression is determined by level of EGF protein expression, the method encompasses the measurement of all isoforms of EGF proteins, EGF peptides or fragments thereof as discussed briefly below. In some embodiments, the EGF protein is mature EGF protein. In some embodiments the EGF protein is glycosylated EGF protein. In alternative embodiments, the EGF protein is between 140-170 kDa, 97 kDa, between 70-66 kDa, 50 kDa, 42 kDa, 35 kDa, 20 kDa and 6 kDa. In some embodiments, the EGF protein or isoforms thereof can be detected in a complex with its receptor, for example in a complex with EGFR. In such embodiments, the EGF/EGFR complex is 250-300 kDa. Protein from biological samples, for example the tissue or cell type to be analyzed can easily be detected or isolated using techniques which are well known to one of skill in the art, including but not limited to Western blot analysis, ELISA, immunoblot, etc.

Without being bound to theory, the EGF gene is transcribed into what is commonly known in the art as preproEGF mRNA. This mRNA is translated into the proEGF protein which is approximately 170 kd polypeptide after glycosylation (24). This protein 17-kDa protein undergoes a process called ectodomain shedding (25), which is likely mediated by ADAM10 (26). The resultant EGF protein isoforms range in size depending on the source, with the 6 kd isoform commonly referred to in the art as matureEGF. Briefly, the EGF protein is synthesized as a 140-170 kDa protein based on the amount of glycosylation. That protein can bind the EGF receptor that can be identified as yielding a band of 250-300 kDa on a western blot analysis. The 140-170 kDa protein is then processed into the smaller sizes 97, 70-66, 50, 42, 35, 20 and 6 kDa.

Without being bound to theory, isoforms of 165, 97, 66, 50, 42 and 6 kDa are found in urine (27). However, in a more comprehensive study examining EGF protein expression in urine, milk, seminal plasma, saliva, tears, amniotic fluid, breast sweat, armpit sweat and gastric juice, EGF protein isoforms of sizes ranging from 300, 150, 70, 20 and 6 kDa were found (28). Human serum has been reported to contain five different sized isoforms of 140, 67, 35, 20 and 6 kDa (27). In HCC cell line lysates, isoforms of approximately 250-300 kDa were found and also isoforms of EGF of approximately 150-165 kDa along with isoforms of 97, 50 and 42 kDa. Similar sized isoforms as to those found in HCC cell lysates have also been found in the liver, with the 97 kDa and 42 kDa isoforms being most prevalent.

In such an embodiment, methods to detect EGF proteins and peptides include ELISA (enzyme linked immunosorbent assay), western blot, immunoprecipitation, immunofluorescence using detection reagents such as an antibody or protein binding agents. Alternatively, a peptide can be detected in a subject by introducing into a subject a labeled anti-peptide antibody and other types of detection agent. For example, the antibody can be labeled with a radioactive marker whose presence and location in the subject is detected by standard imaging techniques, particularly useful are methods that detect the allelic variant of a peptide expressed in a subject and methods which detect fragments of a peptide in a sample.

Methods to detect level of EGF expression in a biological sample are well known to persons skilled in the art, and are encompassed for use in this invention. Commercially available ELISA kits for detection of EGF are also useful in the methods of this invention. Some examples of such kits available include, but are not limited to, ELISA kits to detect levels of human EGF from Serotec, US Biological (MA, USA), Cell Signaling Technologies (MA, USA), Abnova corporation, Anogen, Alpco Diagnostics, Ray Biotech, alphagenix, autogen, R&D Systems, Pepro Tech EC Ltd, cytolab, Bender MedSystems GmbH, Biovision Research Products, EBD biosciences, Chemicon, Axxora Platform, Promo Cell Distrubuters etc.

In alternative embodiments, antibodies directed against wild type or mutant peptides encoded by the allelic variants of the gene of interest, for example EGF, can also be used in disease diagnostics and prognostics. Such diagnostic methods can be used to detect abnormalities in the level of expression of the peptide, or abnormalities in the structure and/or tissue, cellular, or subcellular location of the peptide.

In another embodiment, immunohistochemistry ("IHC") and immunocytochemistry ("ICC") techniques can be used. IHC is the application of immunochemistry to tissue sections, whereas ICC is the application of immunochemistry to cells or tissue imprints after they have undergone specific cytological preparations such as, for example, liquid-based preparations. Immunochemistry is a family of techniques based on the use of a antibody, wherein the antibodies are used to specifically target molecules inside or on the surface of cells. The antibody typically contains a marker that will undergo a biochemical reaction, and thereby experience a change color, upon encountering the targeted molecules. In some instances, signal amplification can be integrated into the particular protocol, wherein a secondary antibody, that includes the marker stain or marker signal, follows the application of a primary specific antibody.

The methods described herein can be performed, for example, by utilizing pre-packaged diagnostic kits, such as those described above, comprising at least one probe which can be conveniently used, e.g., to determine whether a subject has or is at risk of developing disease such as hepatocellular cancer (HCC).

In an alternative embodiment, EGF levels can be determined by determining the level of EGF messenger RNA (mRNA) expression. In some embodiments, EGF mRNA is any mRNA molecules or species transcribed from the EGF gene, for example EGF pre-mRNA and EGF mature mRNA. In some embodiments, the EGF mRNA is prepromRNA. In some embodiments, the EGF mRNA molecules are fragments, portions, and segments of pre-mRNA, for example EGF prepromRNA or EGF mature mRNA. Such molecules can be isolated, derived, or amplified from a biological sample. Detection of mRNA expression is known by persons skilled in the art, and comprise, for example but not limited to, PCR procedures, RT-PCR, Northern blot analysis, differential gene expression, RNA protection assay, microarray analysis, hybridization methods etc.

Nucleic acid and ribonucleic acid (RNA) molecules can be isolated from a particular biological sample using any of a number of procedures, which are well-known in the art, the particular isolation procedure chosen being appropriate for the particular biological sample. For example, freeze-thaw and alkaline lysis procedures can be useful for obtaining nucleic acid molecules from solid materials; heat and alkaline lysis procedures can be useful for obtaining nucleic acid molecules from urine; and proteinase K extraction can be used to obtain nucleic acid from blood (Roiff, A et al. PCR: Clinical Diagnostics and Research, Springer (1994)).

In general, the PCR procedure describes a method of gene amplification which is comprised of (i) sequence-specific hybridization of primers to specific genes within a nucleic acid sample or library, (ii) subsequent amplification involving multiple rounds of annealing, elongation, and denaturation using a DNA polymerase, and (iii) screening the PCR products for a band of the correct size. The primers used are oligonucleotides of sufficient length and appropriate sequence to provide initiation of polymerization, i.e. each primer is specifically designed to be complementary to each strand of the genomic locus to be amplified.

In an alternative embodiment, EGF levels can be determined by reverse-transcription (RT) PCR and by quantitative RT-PCR (QRT-PCR) or real-time PCR methods. Methods of RT-PCR and QRT-PCR are well known in the art, and are described in more detail below.

Probes can be affixed to surfaces for use as "gene chips." Such gene chips can be used to detect genetic variations by a number of techniques known to one of skill in the art. In one technique, oligonucleotides are arrayed on a gene chip for determining the DNA sequence of a by the sequencing by hybridization approach, such as that outlined in U.S. Pat. Nos. 6,025,136 and 6,018,041. The probes of the present invention also can be used for fluorescent detection of a genetic sequence. Such techniques have been described, for example, in U.S. Pat. Nos. 5,968,740 and 5,858,659. A probe also can be affixed to an electrode surface for the electrochemical detection of nucleic acid sequences such as described by Kayyem et al. U.S. Pat. No. 5,952,172 and by Kelley, S. O. et al. (1999) Nucleic Acids Res. 27:4830-4837.

Detection of Novel Polymorphisms in Non-Coding and Coding Regions of the Gene Encoding EGF The present invention described herein relates to methods and compositions for determining and identifying alleles present at particular loci of the EGF gene, or other alleles in the EGF gene that result in increased expression of the EGF protein. This information is useful to diagnose and prognose disease progression as well as select the most effective treatment among treatment options.

In one embodiment, the polymorphisms of the present invention occur in the gene encoding the EGF molecule identified as SEQ ID NO: 1 or fragments thereof or complements thereof. The probes of the present invention will preferably be "biologically active" with respect to either a structural attribute, such as the capacity of a nucleic acid to hybridize to another nucleic acid molecule or to be used by a polymerase as a primer. Alternatively, such an attribute can be catalytic, and thus involve the capacity of the agent to mediate a chemical reaction or response.

In one embodiment, the identity of at least one polymorphic site in EGF is determined. As used herein a polymorphic site includes one or more nucleotide substitutions (SUB), deletions (DEL), insertions (IN), or base changes at a particular site in a nucleic acid sequence. In some embodiments, the identity of between about one and about six polymorphic sites is determined, though the identification of other numbers of sites is also possible. In some embodiments, the polymorphisms and molecules of the present invention are utilized in determining the identity of at least one polymorphic site of the EGF molecule and using that identity as a predictor of increased risk for developing a disease. The type of polymorphism present can also dictate the appropriate drug selection. In other embodiments, the polymorphisms and molecules of the present are used for diagnosing or prognosing an individual with a disease associated with EGF SNP 61A>G.

In one aspect, the polymorphism is present in a open reading frame (coded) region of the gene, in a "silent" region of the gene, in another it is in the promoter region or 5'untranslated region (5"UTR) and in yet another it is in the 3' untranslated region of the transcript. In yet a further embodiment, the polymorphism increases expression at the mRNA level.

Genetic polymorphisms that can be predictive of outcome include, but is not limited to polymorphisms occurring in a gene selected from the group consisting of EGF, epidermal growth factor receptor gene (EGFR), and transforming growth factor alpha (TGFα).

SNPs, Polymorphisms and Alleles

The genomes of all organisms undergo spontaneous mutation in the course of their continuing evolution, generating variant forms of progenitor genetic sequences (Gusella, Ann. Rev. Biochem. 55, 831-854 (1986)). The coexistence of multiple forms of a genetic sequence gives rise to genetic polymorphisms, including SNPs.

Approximately 90% of all polymorphisms in the human genome are SNPs. SNPs are single base positions in DNA at which different alleles, or alternative nucleotides, exist in a population. The SNP position (interchangeably referred to herein as SNP, SNP site, SNP allele or SNP locus) is usually preceded by and followed by highly conserved sequences of the allele (e.g., sequences that vary in less than 1/100 or 1/1000 members of the populations). An individual can be homozygous or heterozygous for an allele at each SNP position. A SNP can, in some instances, be referred to as a "cSNP" to denote that the nucleotide sequence containing the SNP is an amino acid coding sequence.

A SNP can arise from a substitution of one nucleotide for another at the polymorphic site. Substitutions can be transitions or transversions. A transition is the replacement of one purine nucleotide by another purine nucleotide, or one pyrimidine by another pyrimidine. A transversion is the replacement of a purine by a pyrimidine, or vice versa. A SNP can also be a single base insertion or deletion variant referred to as an "in/del" (Weber et al., "Human diallelic insertion/deletion polymorphisms", Am J Hum Genet October 2002; 71(4):854-62).

A synonymous codon change, or silent mutation/SNP (the terms "SNP" and "mutation" are used herein interchangeably), is one that does not result in a change of amino acid due to the degeneracy of the genetic code. A substitution that changes a codon coding for one amino acid to a codon coding for a different amino acid (i.e., a non-synonymous codon change) is referred to as a missense mutation. A nonsense mutation results in a type of non-synonymous codon change in which a stop codon is formed, thereby leading to premature termination of a polypeptide chain and a truncated protein. A read-through mutation is another type of non-synonymous codon change that causes the destruction of a stop codon, thereby resulting in an extended polypeptide product. While SNPs can be bi-, tri-, or tetra-allelic, the vast majority of the SNPs are bi-allelic, and are thus often referred to as "bi-allelic markers", or "di-allelic markers".

As used herein, references to SNPs and SNP genotypes include individual SNPs and/or haplotypes, which are groups of SNPs that are generally inherited together. Haplotypes can have stronger correlations with diseases or other phenotypic effects compared with individual SNPs, and therefore can provide increased diagnostic accuracy in some cases (Stephens et al. Science 293, 489-493, 20 Jul. 2001).

Causative SNPs are those SNPs that produce alterations in gene expression or in the expression, structure, and/or function of a gene product, and therefore are most predictive of a possible clinical phenotype. One such class includes SNPs falling within regions of genes encoding a polypeptide product, i.e. cSNPs. These SNPs can result in an alteration of the amino acid sequence of the polypeptide product (i.e., non-synonymous codon changes) and give rise to the expression of a defective or other variant protein. Furthermore, in the case of nonsense mutations, a SNP can lead to premature termination of a polypeptide product. Such variant products can result in a pathological condition, e.g., genetic disease. Examples of genes in which a SNP within a coding sequence causes a genetic disease include sickle cell anemia and cystic fibrosis.

Causative SNPs do not necessarily have to occur in coding regions; causative SNPs can occur in, for example, any genetic region that can ultimately affect the expression, structure, and/or activity of the protein encoded by a nucleic acid and are encompassed within the scope of the present invention. Such genetic regions include, for example, those involved in transcription, such as SNPs in transcription factor binding domains, SNPs in promoter regions, in areas involved in transcript processing, such as SNPs at intron-exon boundaries that can cause defective splicing, or SNPs in mRNA processing signal sequences such as polyadenylation signal regions. Some SNPs that are not causative SNPs nevertheless are in close association with, and therefore segregate with, a disease-causing sequence. In this situation, the presence of a SNP correlates with the presence of, or predisposition to, or an increased risk in developing the disease. These SNPs, although not causative, are nonetheless also useful for diagnostics, disease predisposition screening, and other uses.

An association study of a SNP and a specific disorder involves determining the presence or frequency of the SNP allele in biological samples from subjects with the disorder of interest, such as liver disease and/or cirrhosis, and comparing the information to that of controls (i.e., individuals who do not have the disorder; controls can be also referred to as "healthy" or "normal" individuals) who are preferably of similar age and race. The appropriate selection of patients and controls is important to the success of SNP association studies. Therefore, a pool of individuals with well-characterized phenotypes is extremely desirable.

A SNP can be screened in diseased tissue samples or any biological sample obtained from a diseased individual, and compared to control samples, and selected for its increased (or decreased) occurrence in a specific pathological condition, such as pathologies related to coronary artery disease and coronary syndrome. Once a statistically significant association is established between one or more SNP(s) and a pathological condition (or other phenotype) of interest, then the region around the SNP can optionally be thoroughly screened to identify the causative genetic locus/sequence(s) (e.g., causative SNP/mutation, gene, regulatory region, etc.) that influences the pathological condition or phenotype. Association studies can be conducted within the general population and are not limited to studies performed on related individuals in affected families (linkage studies).

Particular SNP alleles, sometimes referred to as polymorphisms or polymorphic alleles, of the present invention can be associated with a risk of developing cancer. In some embodiments the cancer is hepatocellular carcinoma (HCC). Mutations or alleles identifying a subject with an increased risk of developing cancer, in particular HCC in subjects with inflammatory diseases, for example liver disease and/or cirrhosis can be referred to as "susceptibility" alleles, and mutations and/or alleles.

Those skilled in the art will readily recognize that nucleic acid molecules can be double-stranded molecules and that reference to a particular site on one strand refers, as well, to the corresponding site on a complementary strand. In defining a SNP position, SNP allele, or nucleotide sequence, reference to an adenine, a thymine (uridine), a cytosine, or a guanine at a particular site on one strand of a nucleic acid molecule also defines the thymine (uridine), adenine, guanine, or cytosine (respectively) at the corresponding site on a complementary strand of the nucleic acid molecule. Thus, reference can be made to either strand in order to refer to a particular SNP position, SNP allele, or nucleotide sequence. Probes and primers, can be designed to hybridize to either strand and SNP genotyping methods disclosed herein can generally target either strand. Throughout the specification, in identifying a SNP position, reference is generally made to the protein-encoding strand, only for the purpose of convenience.

Identification method of SNPs can be of either a positive-type or a negative-type. Positive-type methods determine the identity of a nucleotide contained in a polymorphic site, whereas negative-type methods determine the identity of a nucleotide not present in a polymorphic site. Thus, a wild-type site can be identified either as wild-type or not mutant. For example, at a biallelic polymorphic site where the wild-type allele contains a cytosine and the mutant allele contains adenine, a site can be positively determined to be either adenine or cytosine or negatively determined to be not adenine (and thus cytosine) or not cytosine (and thus adenine).

Alternately, if the polymorphism is a deletion, or addition then the complementary sequence can be detected. As another example, in hybridization-based assay, a target polynucleotide containing a mutated site can be identified positively by hybridizing to an allele-specific oligonucleotide containing the mutated site or negatively, by failing to hybridize to a wild-type allele-specific oligonucleotide. Similarly, a restriction site can be determined to be present or lacking.

In one aspect, the nucleic acid sequences of the gene's allelic variants, or portions thereof, can be the basis for probes or primers, e.g., in methods for determining the identity of the allelic variant of the polymorphic region. Thus, in one embodiment, nucleic acid probes or primers can be used in the methods of the present invention to determine whether a subject is at risk of developing disease such as hepatocellular carcinoma or alternatively, which therapy is most appropriate to prevent the development of the subject getting cancer.

Alleles resulting in an increased expression of the EGF gene product can be located within the non-coding and coding region of EGF gene. Non-coding regions include, for example, intron sequences as well as 5' and 3' untranslated sequences. In one embodiment, one allele associated with increased risk of developing cancer, in particular hepatocellular carcinoma (HCC) in subjects with inflammatory disease, for example cirrhosis is located within a 5'UTR portion of the EGF gene. Changes of interest in a non-coding region include modifications of the nucleic acid such as methylation and/or acetylation are also within the scope of the present invention.

Another embodiment of the present invention provides methods for identifying novel polymorphisms in the EGF gene which are associated with increased risk of developing cancer. The strength of the association between a polymorphic allele and likelihood of developing cancer can be characterized by a particular odds ratio such as an odds ratio of at least 2 with a lower 95% confidence interval limit of greater than 1. Such an odds ratio can be, for example, at least 3.0, 4.0, 5.0, 6.0, 7.0, or 8.0 or greater with a lower 95% confidence interval limit of greater than 1. In one embodiment, the predisposing polymorphic allele is associated with HCC with an odds ratio of at least 2 and a lower 95% confidence limit greater than 1. Methods for determining an odds ratio are well known in the art (see, for example, Schlesselman et al., Case Control Studies: Design, Conduct and Analysis Oxford University Press, New York (1982)).

In one embodiment, alleles associated with an increased likelihood of getting cancer and/or increased levels of EGF is associated with a p value of equal to or less than 0.05. In other embodiments, the p value is equal to or less than 0.01. As used herein, the term "p value" is synonymous with "probability value." As is well known in the art, the expected p value for the association between a random allele and disease is 1.00. A p value of less than about 0.05 indicates that the allele and disease do not appear together by chance but are influenced by positive factors. Generally, the statistical threshold for significance of linkage has been set at a level of allele sharing for which false positives would occur once in twenty genome scans (p=0.05). In particular embodiments, alleles associated with infarct size and responsiveness to adenosine agonists is associated with infarct size with a p value of equal to or less than 0.1, 0.05, 0.04, 0.03, 0.02, 0.01, 0.009, 0.008, 0.007, 0.006, 0.005, 0.004, 0.003, 0.002 or 0.001, or with a p value of less than 0.00095, 0.0009, 0.00085, 0.0008 or 0.0005. It is recognized that, in some cases, p values can need to be corrected, for example, to account for factors such as sample size (number of families), genetic heterogeneity, clinical heterogeneity, or analytical approach (parametric or nonparametric method).

Genotyping EGF Alleles

According to one aspect of the present invention, a method for determining whether a human is homozygous for a polymorphism, heterozygous for a polymorphism, or lacking the polymorphism altogether (i.e. homozygous wildtype) is encompassed. As an exemplary embodiment only, method to detect the 61A>G variance in the EGF gene, a method for determining the G-allele, heterozygous for the G- and A-alleles, or homozygous for the G-allele of the human EGF gene are provided. Substantially any method of detecting any allele of the EGF gene (including coding and no-coding regions, for example the 5'UTR) gene, such as hybridization, amplification, restriction enzyme digestion, and sequencing methods, can be used.

In one embodiment, a haplotyping method useful according to the present invention is a physical separation of alleles by cloning, followed by sequencing. Other methods of haplotyping, useful according to the present invention include, but are not limited to monoallelic mutation analysis (MAMA) (Papadopoulos et al. (1995) Nature Genet. 11:99-102) and carbon nanotube probes (Woolley et al. (2000) Nature Biotech. 18:760-763). U.S. Patent Application No. US 2002/0081598 also discloses a useful haplotyping method which involves the use of PCR amplification.

Computational algorithms such as expectation-maximization (EM), subtraction and PHASE are useful methods for statistical estimation of haplotypes (see, e.g., Clark, A. G. Inference of haplotypes from PCR-amplified samples of diploid populations. *Mol Biol Evol* 7, 111-22. (1990); Stephens, M., Smith, N. J. & Donnelly, P. A new statistical method for haplotype reconstruction from population data. *Am J Hum Genet* 68, 978-89. (2001); Templeton, A. R., Sing, C. F., Kessling, A. & Humphries, S. A cladistic analysis of phenotype associations with haplotypes inferred from restriction endonuclease mapping. The analysis of natural populations. *Genetics* 120, 1145-54. (1988)).

In one embodiment, an allelic discrimination method for identifying the EGF genotype of a human can be used. In one embodiment, the allelic discrimination method of the present invention involves use of a first oligonucleotide probe which anneals with a target portion of the individual's genome. As an illustrative example only, the target portion comprises a portion of the region of EGF gene to be screened, for example, including the nucleotide residue at position 61 in SEQ ID NO: 1. Because the nucleotide residue at this position differs, for example at position in the G-allele and the A-allele, the first probe is completely complementary to only one of the two alleles. Alternatively, a second oligonucleotide probe can also be used which is completely complementary to the target portion of the other of the two alleles. The allelic discrimination method of the present invention also involves use of at least one, and preferably a pair of amplification primers for amplifying a reference region of the EGF gene of a subject. The reference region includes at least a portion of the human EGF, for example a portion including the nucleotide residue at position 61 of the EGF gene in SEQ ID NO: 1.

The probe in some embodiments is a DNA oligonucleotide having a length in the range from about 20 to about 40 nucleotide residues, preferably from about 20 to about 30 nucleotide residues, and more preferably having a length of about 25 nucleotide residues. In one embodiment, the probe is rendered incapable of extension by a PCR-catalyzing enzyme such as Taq polymerase, for example by having a fluorescent probe attached at one or both ends thereof. Although non-labeled oligonucleotide probes can be used in the kits and methods of the invention, the probes are preferably detectably labeled. Exemplary labels include radionuclides, light-absorbing chemical moieties (e.g. dyes), fluorescent moieties, and the like. Preferably, the label is a fluorescent moiety, such as 6-carboxyfluorescein (FAM), 6-carboxy-4,7,2',7'-tetrachlorofluoroscein (TET), rhodamine, JOE (2,7-dimethoxy-4, 5-dichloro-6-carboxyfluorescein), HEX (hexachloro-6-carboxyfluorescein), or VIC.

In some embodiments, the probe of the present invention comprises both a fluorescent label and a fluorescence-quenching moiety such as 6-carboxy-N,N,N',N'-tetramethylrhodamine (TAMRA), or 4-(4'-dimethylaminophenylazo) benzoic acid (DABCYL). When the fluorescent label and the fluorescence-quenching moiety are attached to the same oligonucleotide and separated by no more than about 40 nucleotide residues, and preferably by no more than about 30 nucleotide residues, the fluorescent intensity of the fluorescent label is diminished. When one or both of the fluorescent label and the fluorescence-quenching moiety are separated from the oligonucleotide, the intensity of the fluorescent label is no longer diminished. In some embodiments, the probe of the present invention has a fluorescent label attached at or near (i.e. within about 10 nucleotide residues of) one end of the probe and a fluorescence-quenching moiety attached at or near the other end. Degradation of the probe by a PCR-catalyzing enzyme releases at least one of the fluorescent label and the fluorescence-quenching moiety from the probe, thereby discontinuing fluorescence quenching and increasing the detectable intensity of the fluorescent labels. Thus, cleavage of the probe (which, as discussed above, is correlated with complete complementarity of the probe with the target portion) can be detected as an increase in fluorescence of the assay mixture.

If different detectable labels are used, more than one labeled probe can be used, and therefore polymorphisms can be performed in multiplex. For example, the assay mixture can contain a first probe which is completely complementary to the target portion of the polymorphism of EGF gene and to which a first label is attached, and a second probe which is completely complementary to the target portion of the wildtype allele. When two probes are used, the probes are detectably different from each other, having, for example, detectably different size, absorbance, excitation, or emission spectra, radiative emission properties, or the like. For example, a first probe can be completely complementary to the target portion of the polymorphism and have FAM and TAMRA attached at or near opposite ends thereof. The first probe can be used in the method of the present invention together with a second probe which is completely complementary to the target portion of the wildtype allele and has TET and TAMRA attached at or near opposite ends thereof. Fluorescent enhancement of FAM (i.e. effected by cessation of fluorescence quenching upon degradation of the first probe by Taq polymerase) can be detected at one wavelength (e.g. 518 nanometers), and fluorescent enhancement of TET (i.e. effected by cessation of fluorescence quenching upon degradation of the second probe by Taq polymerase) can be detected at a different wavelength (e.g. 582 nanometers).

In some embodiments, the probe exhibits a melting temperature (Tm) within the range from about 60° C. to 70° C., and often within the range from 65° C. to 67° C. Furthermore, because each probe is completely complementary to only one of the alleles of the EGF gene, each probe will necessarily have at least one nucleotide residue which is not complementary to the corresponding residue of the other allele. This non-complementary nucleotide residue of the probe is often located near the midsection of the probe (i.e. within about the central third of the probe sequence) and is usually approximately equidistant from the ends of the probe. As an illustrative example, the probe which is completely complementary to the polymorphic allele of EGF gene can, for example, be completely complementary to nucleotide residues surrounding position 61 of the polymorphic allele, as defined by the positions of SEQ ID NO:1. For example, because the G- and A-alleles differ at position 61, this probe will have a mismatched base pair at the nucleotide residues where the variance is, for instance a mismatch in the annealed probe at one nucleotide position corresponding with the target position of the G-allele.

By way of example, labeled probes having the sequences of SEQ ID NO:1 can be used in order to determine the allelic content of an individual (e.g. to assess whether the mammal comprises one or both of an G allele and an A allele of EGF at position 61). For example, custom TaqMan SNP genotyping probes for each allele can be designed using Primer Express® v2.0 software (Applied Biosystems) using recommended guidelines. Successful discrimination of each allele can be verified using population control individuals. Genomic DNA (e.g. 20 ng) can be amplified according to assay recommendations and genotyping analysis performed, as described in greater detail below.

The size of the reference portion which is amplified according to the allelic discrimination method of the present invention is typically not more than about 100 nucleotide residues. It is also typical that the Tm for the amplified reference portion with the genomic DNA or fragment thereof be in the range from about 57° C. to 61° C., where possible.

It is understood that binding of the probe(s) and primers and that amplification of the reference portion of the EGF gene according to the allelic discrimination method of the present invention will be affected by, among other factors, the concentration of $Mg^{++}$ in the assay mixture, the annealing and extension temperatures, and the amplification cycle times. Optimization of these factors requires merely routine experimentation which are well known to skilled artisans.

Another allelic discrimination method suitable for use in the present invention employs "molecular beacons". Detailed description of this methodology can be found in Kostrikis et al., Science 1998; 279:1228-1229, which is incorporated herein by reference.

The use of microarrays comprising a multiplicity of reference sequences is becoming increasingly common in the art. Accordingly, another aspect of the present invention comprises a microarray having at least one oligonucleotide probe, as described above, appended thereon.

It is understood, however, that any method of ascertaining an allele of a gene can be used to assess the genotype of the 5'UTR of the EGF gene and the coding region of EGF gene in a mammal. Thus, the present invention includes known methods (both those described herein and those not explicitly described herein) and allelic discrimination methods which can be hereafter developed.

As used herein, a first region of an oligonucleotide "flanks" a second region of the oligonucleotide if the two regions are adjacent one another or if the two regions are separated by no more than about 1000 nucleotide residues, and preferably no more than about 100 nucleotide residues.

A second set of primers is "nested" with respect to a first pair of primers if, after amplifying a nucleic acid using the first pair of primers, each of the second pair of primers anneals with the amplified nucleic acid, such that the amplified nucleic acid can be further amplified using the second pair of primers.

Nucleic acid molecules of the present invention can be prepared by two general methods: (1) Synthesis from appropriate nucleotide triphosphates, or (2) Isolation from biological sources. Both methods utilize protocols well known in the art.

The availability of nucleotide sequence information, such as a full length nucleic acid sequence of SEQ ID NO: 1 or a part or fragment thereof, enables preparation of isolated nucleic acid molecules of the present invention by oligonucleotide synthesis. Synthetic oligonucleotides can be prepared by the phosphoramidite method employed in the Applied Biosystems 38A DNA Synthesizer or similar devices. The resultant construct can be purified according to methods known in the art, such as high performance liquid chromatography (HPLC). Long, double-stranded polynucleotides, such as a DNA molecule of the present invention, must be synthesized in stages, due to the size limitations inherent in current oligonucleotide synthetic methods. Thus, for example, a 1.4 kb double-stranded molecule can be synthesized as several smaller segments of appropriate complementarity. Complementary segments thus produced can be annealed such that each segment possesses appropriate cohesive termini for attachment of an adjacent segment. Adjacent segments can be ligated by annealing cohesive termini in the presence of DNA ligase to construct an entire 1.4 kb double-stranded molecule. A synthetic DNA molecule so constructed can then be cloned and amplified in an appropriate vector.

Nucleic acid sequences of the present invention can also be isolated from appropriate biological sources using methods known in the art.

Also contemplated with the scope of the present invention are vectors or plasmids containing the nucleic acid sequence of SEQ ID NO:1 or fragment thereof and host cells or animals containing such vectors or plasmids. Also encompassed within the scope of the present invention are vectors or plasmids containing the nucleic acid sequences of portions of the nucleic acid sequences of SEQ ID NO:1 comprising the variants of the 5'UTR of EGF as disclosed in this invention, and host cells or animals containing such vectors or plasmids. Methods for constructing vectors or plasmids containing the nucleic acid sequence of SEQ ID NO:1 and host cells or animals containing the same are within the ability of persons skilled in the art of molecular biology.

Nucleic acids. Certain embodiments of the present invention concern various nucleic acids, including promoters, amplification primers, oligonucleotide probes and other nucleic acid elements involved in the analysis of genomic DNA. In certain aspects, a nucleic acid comprises a wild type, a mutant and/or a polymorphic nucleic acid.

Detection of Variances Mutations and/or Polymorphisms in the Gene Encoding EGF.

The polymorphisms of the present invention can be detected directly or indirectly using any of a variety of suitable methods including fluorescent polarization, mass spectroscopy, and the like. Suitable methods comprise direct or indirect sequencing methods, restriction site analysis, hybridization methods, nucleic acid amplification methods, gel migration methods, the use of antibodies that are specific for the proteins encoded by the different alleles of the polymorphism, or by other suitable means. Alternatively, many such methods are well known in the art and are described, for example in T. Maniatis et al., Molecular Cloning, a Laboratory Manual, 2nd Edition, Cold Spring Harbor Press, Cold Spring Harbor, N.Y. (1989), J. W. Zyskind et al., Recombinant DNA Laboratory Manual, Academic Press, Inc., New York (1988), and in R. Elles, Molecular Diagnosis of Genetic Diseases, Humana Press, Totowa, N.J. (1996), and Mamotte et al, 2006, Clin Biochem Rev, 27; 63-75) each herein incorporated by reference.

According to the present invention, any approach that detects mutations or polymorphisms in a gene can be used, including but not limited to single-strand conformational polymorphism (SSCP) analysis (Orita et al. (1989) Proc. Natl. Acad. Sci. USA 86:2766-2770), heteroduplex analysis (Prior et al. (1995) Hum. Mutat. 5:263-268), oligonucleotide ligation (Nickerson et al. (1990) Proc. Natl. Acad. Sci. USA 87:8923-8927) and hybridization assays (Conner et al. (1983) Proc. Natl. Acad. Sci. USA 80:278-282). Traditional Taq polymerase PCR-based strategies, such as PCR-RFLP, allele-specific amplification (ASA) (Ruano and Kidd (1989) Nucleic Acids Res. 17:8392), single-molecule dilution (SMD) (Ruano et al. (1990) Proc. Natl. Acad. Sci. USA 87:6296-6300), and coupled amplification and sequencing (CAS) (Ruano and Kidd (1991) Nucleic Acids Res. 19:6877-6882), are easily performed and highly sensitive methods to determine haplotypes of the present invention (Michalatos-Beloin et al. (1996) Nucleic Acids Res. 24:4841-4843; Barnes (1994) Proc. Natl. Acad. Sci. USA 91:5695-5699; Ruano and Kidd (1991) Nucleic Acids Res. 19:6877-6882).

Restriction Enzyme Analysis

In one embodiment, restriction enzymes can be utilized to identify variances or a polymorphic site using "restriction fragment length polymorphism" (RFLP) analysis (Lentes et al., Nucleic Acids Res. 16:2359 (1988); and C. K. McQuitty et al., Hum. Genet. 93:225 (1994)). In RFLP, at least one target polynucleotide is digested with at least one restriction enzyme and the resulting restriction fragments are separated based on mobility in a gel. Typically, smaller fragments migrate faster than larger fragments. Consequently, a target polynucleotide that contains a particular restriction enzyme recognition site will be digested into two or more smaller fragments, which will migrate faster than a larger fragment lacking the restriction enzyme site. Knowledge of the nucleotide sequence of the target polynucleotide, the nature of the polymorphic site, and knowledge of restriction enzyme recognition sequences guide the design of such assays. In another embodiment of the present invention, restriction site analysis of particular nucleotide sequence by restriction enzymes the identity of a nucleotide at a polymorphic site is determined by the presence or absence of a restriction enzyme site. A large number of restriction enzymes are known in the art and, taken together, they are capable of recognizing at least one allele of many polymorphisms.

Allele-Specific Amplification (ASA).

Allele-specific Amplification is also known as amplification refectory mutation system (ARMS) uses allele specific oligonucleotides (ASO) PCR primers and is an well established and known PCR based method for genotyping (Newton et al, J Med Genet, 1991; 28; 248-51). Typically, one of the two oligonucleotide primers used for the PCR binds to the mutation suite, and amplification only takes place if the nucleotide of the mutation is present, with a mismatch being refractory to amplification. The resulting PCR Products can be analyzed by any means known to persons skilled in the art. In a variation of the approach, termed mutagenically separated PCR (MS-PCR) the two ARMS primer of different lengths, one specific for the normal gene and one for the mutation are used, to yield PCR procures of different lengths for the normal and mutant alleles (Rust et al, Nucl Acids Res, 1993; 21; 3623-9). Subsequent gel electrophoresis, for example will show at least one of the two allelic products, with normal, mutant or both (heterozygote) genes. A further variation of this forms the basis of the Masscode System™ (www.bioserve.com) which uses small molecular weight tags covalently attached through a photo-cleavable linker to the ARMS primers, with each ARMS primers labeled with a tag of differing weight (Kokoris et al, 2000, 5; 329-40). A catalogue of numerous tags allows simultaneous amplification/genotyping (multiplexing) of 24 different targets in a single PCR reaction. For any one mutation, genotyping is based on comparison of the relative abundance of the two relevant mass tags by mass spectrometry.

Ligation Based Assays

A number of approaches use DNA ligase, an enzyme that can join two adjacent oligonucleotides hybridized to a DNA template. In Oligonucleotide ligation assay (OLA) the sequence surrounding the mutation site is first amplified and one strand serves as a template for three ligation probes, two of these are ASO (allele-specific oligonucleotides) and a third common probe. Numerous approaches cane be used for the detection of the ligated products, for example the ASOs with differentially labeled with fluorescent of hapten labels and ligated products detected by fluorogenic of colorimetric enzyme-linked immunosorbent assays (Tobe et al, Nuclic Acid Res, 1996; 24; 3728-32). For electrophorosis-based systems, use of a morbidity modifier taqgs or variation in probe length coupled with fluorescence detection enables the multiplex genotyping of several single nucleotide substitutions in a single tube (Baron et al, 1997; Clinical Chem., 43; 1984-6). When used on arrays, ASOs can be spotted at specific locations or addresses on a chip, PCR amplified DNA can then be added and ligation to labeled oligonucleotides at specific addresses on the array measured (Zhong et al, Proc Natl Acad Sci 2003; 100; 11559-64).

Single-Base Extension

Single base-extension or minisequencing involves annealing an oligonucleotide primer to the single strand of a PCR product and the addition of a single dideoxynucleotide by thermal DNA polymerase. The oligonucleotide is designed to be one base short of the mutation site. The dideoxynucleotide incorporated is complementary to the base at the mutation site. Approaches cans uses different fluorescent tags or haptens for each of the four different dideoxynucleotides (Pastinen et al, Clin Chem 1996, 42; 1391-7). The dideoxynucleotide differ in molecular weight and this is the basis for single-base extension methods utilizing mass-spectrometry, and genotyping based on the mass of the extended oligonucleotide primer, can be used, for example matrix-assisted laser adsorption/ionization time of flight mass spectrometry or MALDI-TOF (Li et al, Electrophorosis, 1999, 20; 1258-65), which is quantitative and can be used to calculate the relative allele abundance making the approach suitable for other applications such as gene dosage studies (for example for estimation of allele frequencies on pooled DNA samples).

Minisequencing or Microsequencing by MALDI-TOF can be performed by means known by persons skilled in the art. In a variation of the MALDI-TOF technique, some embodiments can use the Sequenom's Mass Array Technology (www.sequenom.com) (Sauser et al, Nucleic Acid Res, 2000, 28; E13 and Sauser et al, Nucleic Acid Res 2000, 28: E100). and also the GOOD Assay (Sauer S et al, Nucleic Acid Res, 2000; 28, E13 and Sauer et al, Nucleic Acid Res, 2000; 28:E100).

In some embodiments, variations of MALDI-TOF can be performed for analysis of variances in the EGF gene. For example, MALDI and electrospray ionization (ESI) (Sauer S. Clin Chem Acta, 2006; 363; 93-105) is also useful with the methods of the present invention.

Hybridization Based Genotyping

Normal or mutant alleles can also be genotypes by measuring the binding of allele-specific oligonucleotides (ASO) hybridization probes. In such embodiments, two ASO probes, one complementary to the normal allele and the other to the mutant allele are hybridized to PCR-amplified DNA spanning the mutation site. In some embodiments, the amplified products can be immobilized on a solid surface and hybridization to radiolabelled oligonucleotides such as known as a 'dot-blot' assay. In alternative embodiments, the binding of the PCR products containing a quantifiable label (eg biotin or fluorescent labels) to a solid phase allele-specific oligonucleotide can be measured. Alternatively, for a reverse hybridization assay, or "reverse dot-blot" the binding of PCR products containing a quantifiable label (for example but not limited to biotin or fluorescent labels) to a solid phase allele-specific oligonucleotide can be measured. In some embodiments, the use of microarrays comprising hundreds of ASO immobilized onto a sold support surfaces to form an array of ASP can also be used for large scale genotyping of multiple single polymorphisms simultaneously, for example Affymetrix GeneChip® Mapping 10K Array, which can easily be performed by persons skilled in the art.

Homogenous Assays

Homogenous assays, also called "closed tube" arrays, genomic DNA and all the reagents required for the amplification and genotyping are added simultaneously. Genotyping can be achieved without any post-amplification processing. In some embodiments, one such homogenous assay is the 5'fluorogenic nuclease assay, also known as the TaqMan® Assay (Livak et al, Genet Anal, 1999; 14:143-9) and in alternative embodiments Melting curve analyses of FRET probes are used. Such methods are carried out using "real-time" thermocyclers, and utilize two dual-labeled ASO hybridization probes complementary to normal and mutant alleles, where the two probes have different reported labels but a common quencher dye. In such embodiments, the changes in fluorescence characteristics of the probes upon binding to PCR products of target genes during amplification enables "real-time" monitoring of PCR amplification and differences in affinity of the fluorogenic probes for the PCR products of normal and mutant genes enables differentiation of genotypes. The approach uses two dual-labeled ASO hybridization probes complementary to the mutant and normal alleles. The two probes have different fluorescent reported dyes but a common quencher dye. When intact, the probes do not fluoresces due to the proximity of the reporter and quencher dyes. During annealing phase of PCR, two probes compete for hybridization to their target sequences, downstream of the primer sites and are subsequently cleaved by 5' nuclease activity of *Thermophilis aquaticus* (Taq) polymerase as the primer is extended, resulting in the separation of the reporter dyes from the quencher. Genotyping is determined by measurement of the fluorescent intensity of the two reporter dyes after PCR amplification. Thus, when intact the probes do not fluoresce due to the proximity of the quencher dyes, whereas during the annealing phase of the PCR the probes compete for hybridization of the target sequences and the separation of one of the probes from the quencher which can be detected.

Melting-curve analysis of FRET hybridization is another approach useful in the method of the invention. Briefly, the reaction includes two oligonucleotide probes which when in close proximity forms a fluorescent complex, where one probe often termed the "mutant sensor" probe is designed to specifically hybridizes across the mutation site and the other probe (often referred to as the "anchor probe") hybridizes to an adjacent site. Fluorescent light is emitted by the "donor" excites the "acceptor" fluorphore creasing a unique fluorogenic complex, which only forms when the probes bind to adjacent sites on the amplified DNA. The "sensor" probe is complementary to either the normal or the mutant allele. Once PCR is complete, heating of the sample through the melting temperatures of the probe yields a fluorescent temperature curve which differs for the mutant and normal allele.

A variation of the FRET hybridization method is the LCGreen™ method, which obviates the requirement for fluorescent labeled probes altogether. LCGreen™ is a sensitive highly fluorogenic double-stranded DNA (dsDNA) binding dye that is used to detect the dissociation of unlabeled probes (Liew et al, Clin Chem, 2004; 50; 1156-64 and Zhou et al, Clin Chem, 2005; 51; 1761-2). The method uses unlabeled allele-specific oligonucleotides probes that are perfectly complementary either to the mutant or normal allele, and the mismatch of the ASO/template double strand DNA complex results in a lower melting temperature and an earlier reduction in fluorescent signal form the dsDNA binding dye with increasing temperature.

The OLA can also be used for FRET Probes (Chen et al, 1998; 8:549-56), for example, the PCR/ligation mixture can contain PCR primers, DNA polymerase without 5' nuclease activity, thermal stable DNA ligase and oligonucleotides for the ligation reaction. The ligation of the allele-specific oligonucleotides have a different acceptor fluorophore and the third ligation oligonucleotide, which binds adjacently to the ASO has a donor fluorophore, and the three ligation oligonucleotides are designed to have a lower melting temperature for the PCR primers to prevent their interference in the PCR amplification. Following PCR, the temperature is lowered to allow ligation to proceed, which results in FRET between the donor and acceptor dyes, and alleles can be disconcerted by comparing the fluorescence emission of the two dyes.

Alternatives to homogenous PCR- and hybridization-based techniques are also encompassed. For example, molecular beacons (Tyagi et al, Nat Biotech, 1998; 16:49-53) and Scopion® probes (Thelwell et al, Nucleic Acid Res, 2000; 28; 3752-610).

The OLA can also be performed by the use of FRET probes (Chen et al, Genome Res, 1998; 8:549-56). In such an embodiment, the PCR/ligation mix contains PCR primers, a thermostable DNA polymerase without 5' exonuclease activity (to prevent the cleavage of ligation probes during the ligation phase), a thermostable DNA ligase as well as the oligonucleotides for the ligation reaction. The ligation of the ASO each have a different acceptor fluorophore and the third ligation oligonucleotide which binds adjacently to the ASO has a donor fluorophore. The three ligation oligonucleotides are designed to have a lower melting temperature than the annealing temperature for the PCR primers prevent their interference in PCR amplification. Following PCR, the temperature is lowered to allow ligation to proceed. Ligation results in FRET between donor and acceptor dyes, and alleles can be discerned by comparing the fluorescence emission of the two dyes.

Further, variations of the homogenous PCR- and hybridization based techniques to detect polymorphisms are also encompassed in the present invention. For example, the use of Molecular Beacons (Tyagi et al, Nat Biotech 1998; 16; 49-53) and Scorpion® Probes (Thelwell et al, Nucleic Acid Res 2000; 28; 3752-61). Molecular Beacons are comprised of oligonucleotides that have fluorescent reporter and dyes at their 5' and 3' ends, with the central portion of the oligonucleotide hybridizing across the target sequence, but the 5' and 3' flanking regions are complementary to each other. When not hybridized to their target sequence, the 5' and 3' flanking regions hybridize to form a stem-loop structure, and there is little fluorescence because of the proximity of the reported and the quencher dyes. However, upon hybridization to their target sequence, the dyes are separated and there is a large increase in the fluorescence. Mismatched probe-target hybrids dissociate at substantially lower temperatures than exactly matched complementary hybrids. There are a number of variations of the "molecular Beacon" approach. In some embodiments, such a variation includes use of Scorpion® Probes which are similar but incorporate a PCR primer sequence as part of the probe (Thelwell et al, Nucleic Acid Res 2000; 28; 3752-61). In another variation, 'duplex' format gives a better fluorescent signal (Solinas et al, Nucleic Acid Res, 2001, 29; E96).

In another embodiment, polymorphisms can be detected by genotyping using a homogenous or real-time analysis on whole blood samples, without the need for DNA extraction or real-time PCR. Such a method is compatible with FRET and TaqMan® (Castley et al, Clin Chem, 2005; 51; 2025-30) enabling extremely rapid screening for the particular polymorphism of interest.

Fluorescent Polarization (FP). In FP, the degree to which the emitted light remains polarized in a particular plane is proportional to the speed at which the molecules rotate and tumble in solution. Under constant pressure, temperature and viscosity, FP is directly related to the molecular weight of a fluorescent species. Therefore, when a small fluorescent molecule is incorporated into a larger molecule, there is an increase in FP. FP can be used in for genotyping of polymorphisms of interest (Chen et al, Genome Res, 1999; 9:492-8 and Latif et al, Genome Res, 2001; 11; 436-40). FP can be utilized in 5' nuclease assay (as described above), where the oligonucleotide probe is digested to a lower molecule weight species, for example is amenable to analysis by FP, but with the added benefit of not requiring a quencher. For example, Perkin-Elmers AcycloPrime™-FP SNP Detection Kit can be used as a FP minisequencing method. Following PCR amplification, unincorporated primers and nucleotides are degraded enzymatically, the enzymes heat inactivated and a minisequencing reaction using DNA polymerase and fluorescent-labelled dideoxynucleotides performed. FP is then measured, typically in a 96- to 386-well plate format on a FP-plate reader.

Pyrosequencing™. Pyrosequencing™ is a novel and rapid sequencing technique. It is a homogenous methods which is not based on chain termination, does not use dideoxynucleotides, nor does it require electrophorosis (Ahmadian et al, Anal Biochem, 2000, 280:103-10; Alderborn et al, Genome Res, 2000; 10:1249-58; and Ronaghi et al, Anal Biochem, 2000; 286:282-8). The approach is based on the generation of pyrophosphate whenever a deoxynucleotide is incorporated during polymerization of DNA, for example as nucleotides are added to the 3; end of a sequencing primer, or a primer extension: DNAn+dNTP→DNAn+1+pyrophosphate. The generation of pyrophosphate us coupled to a luciferase catalyzed reaction resulting in light emission if the particular deoxynucleotide added is incorporated, yielding a qualitative and distinctive program. Sample processing includes PCR amplification with a biotinylated primer, isolation of the biotinylated single stranded amplicon on streptavidin coated beads (or other solid phase) and annealing of a sequencing primer. Samples are then analyzed by a Pyrosequencer™ (www.pyrosequencing.com) which adds a number of enzymes and substrates required for indicator reaction, including sulfurylase and luciferase, as well as a pyrase for degradation of unincorporated nucleotides. The sample is then interrogated by addition of the four deoxynucleotides. Light emission is detected by a charge coupled device camera (CCD) and is proportional to the number of nucleotides incorporated. Results are automatically assigned by pattern recognition.

Other techniques known to persons skilled in the art are also incorporated for use with the present invention, for example see Kwok, Hum Mut 2002; 9; 315-323 and Kwok, Annu Rev Genomic Hum Genetics, 2001; 2; 235-58 for reviews, which are incorporated herein in their entirety by reference. Examples of other techniques to detect variances and/or polymorphisms are the Invader® Assay (Gut et al, Hum Mutat, 2001; 17:475-92, Shi et al, Clin Chem, 2001, 47, 164-92, and Olivier et al, Mutat Res, 2005; 573:103-110), the method utilizing FLAP endonucleases (U.S. Pat. No. 6,706, 476) and the SNPlex genotyping systems (Tobler et al, J. Biomol Tech, 2005; 16; 398-406.

In one embodiment, a long-range PCR (LR-PCR) is used to detect mutations or polymorphisms of the present invention. LR-PCR products are genotyped for mutations or polymorphisms using any genotyping methods known to one skilled in the art, and haplotypes inferred using mathematical approaches (e.g., Clark's algorithm (Clark (1990) Mol. Biol. Evol. 7:111-122).

For example, methods including complementary DNA (cDNA) arrays (Shalon et al., Genome Research 6(7):639-45, 1996; Bernard et al., Nucleic Acids Research 24(8):1435-42, 1996), solid-phase mini-sequencing technique (U.S. Pat. No. 6,013,431, Suomalainen et al. Mol. Biotechnol. June; 15(2): 123-31, 2000), ion-pair high-performance liquid chromatography (Doris et al. J. Chromatogr. A can 8; 806(1):47-60, 1998), and 5' nuclease assay or real-time RT-PCR (Holland et al. Proc Natl Acad Sci USA 88: 7276-7280, 1991), or primer extension methods described in the U.S. Pat. No. 6,355,433, can be used.

In one embodiment, the primer extension reaction and analysis is performed using PYROSEQUENCING™ (Uppsala, Sweden) which essentially is sequencing by synthesis. A sequencing primer, designed directly next to the nucleic acid differing between the disease-causing mutation and the normal allele or the different SNP alleles is first hybridized to a single stranded, PCR amplified DNA template from the individual, and incubated with the enzymes, DNA polymerase, ATP sulfurylase, luciferase and apyrase, and the substrates, adenosine 5' phosphosulfate (APS) and luciferin. One of four deoxynucleotide triphosphates (dNTP), for example, corresponding to the nucleotide present in the mutation or polymorphism, is then added to the reaction. DNA polymerase catalyzes the incorporation of the dNTP into the standard DNA strand. Each incorporation event is accompanied by release of pyrophosphate (PPi) in a quantity equimolar to the amount of incorporated nucleotide. Consequently, ATP sulfurylase converts PPi to ATP in the presence of adenosine 5' phosphosulfate. This ATP drives the luciferase-mediated conversion of luciferin to oxyluciferin that generates visible light in amounts that are proportional to the amount of ATP. The light produced in the luciferase-catalyzed reaction is detected by a charge coupled device (CCD) camera and seen as a peak in a PYROGRAM™. Each light signal is proportional to the number of nucleotides incorporated and allows a clear determination of the presence or absence of, for example, the mutation or polymorphism. Thereafter, apyrase, a nucleotide degrading enzyme, continuously degrades unincorporated dNTPs and excess ATP. When degradation is complete, another dNTP is added which corresponds to the dNTP present in for example the selected SNP. Addition of dNTPs is performed one at a time. Deoxyadenosine alfa-thio triphosphate (dATPS) is used as a substitute for the natural deoxyadenosine triphosphate (dATP) since it is efficiently used by the DNA polymerase, but not recognized by the luciferase. For detailed information about reaction conditions for the PYROSEQUENCING, see, e.g. U.S. Pat. No. 6,210,891, which is herein incorporated by reference in its entirety.

Molecular beacons also contain fluorescent and quenching dyes, but FRET only occurs when the quenching dye is directly adjacent to the fluorescent dye. Molecular beacons are designed to adopt a hairpin structure while free in solution, bringing the fluorescent dye and quencher in close proximity. Therefore, for example, two different molecular beacons are designed, one recognizing the mutation or polymorphism and the other the corresponding wildtype allele. When the molecular beacons hybridize to the nucleic acids, the fluorescent dye and quencher are separated, FRET does not occur, and the fluorescent dye emits light upon irradiation. Unlike TaqMan probes, molecular beacons are designed to remain intact during the amplification reaction, and must rebind to target in every cycle for signal measurement. TaqMan probes and molecular beacons allow multiple DNA species to be measured in the same sample (multiplex PCR), since fluorescent dyes with different emission spectra can be attached to the different probes, e.g. different dyes are used in making the probes for different disease-causing and SNP alleles. Multiplex PCR also allows internal controls to be co-amplified and permits allele discrimination in single-tube assays. (Ambion Inc, Austin, Tex., TechNotes 8(1)—February 2001, Real-time PCR goes prime time).

Another method to detect mutations or polymorphisms is by using fluorescence tagged dNTP/ddNTPs. In addition to use of the fluorescent label in the solid phase mini-sequencing method, a standard nucleic acid sequencing gel can be used to detect the fluorescent label incorporated into the PCR amplification product. A sequencing primer is designed to anneal next to the base differentiating the disease-causing and normal allele or the selected SNP alleles. A primer extension reaction is performed using chain terminating dideoxyribonucleoside triphosphates (ddNTPs) labeled with a fluorescent dye, one label attached to the ddNTP to be added to the standard nucleic acid and another to the ddNTP to be added to the target nucleic acid.

Alternatively, an INVADER® assay can be used (Third Wave Technologies, Inc (Madison, Wis.)). This assay is generally based upon a structure-specific nuclease activity of a variety of enzymes, which are used to cleave a target-dependent cleavage structure, thereby indicating the presence of specific nucleic acid sequences or specific variations thereof in a sample (see, e.g. U.S. Pat. No. 6,458,535). For example, an INVADER® operating system (OS), provides a method for detecting and quantifying DNA and RNA. The INVADER® OS is based on a "perfect match" enzyme-substrate reaction. The INVADER® OS uses proprietary CLEAVASE® enzymes (Third Wave Technologies, Inc (Madison, Wis.)), which recognize and cut only the specific structure formed during the INVADER® process which structure differs between the different alleles selected for detection, i.e. the disease-causing allele and the normal allele as well as between the different selected SNPs. Unlike the PCR-based methods, the INVADER® OS relies on linear amplification of the signal generated by the INVADER® process, rather than on exponential amplification of the target.

In the INVADER® process, two short DNA probes hybridize to the target to form a structure recognized by the CLEAVASE® enzyme. The enzyme then cuts one of the probes to release a short DNA "flap." Each released flap binds to a fluorescently-labeled probe and forms another cleavage structure. When the CLEAVASE® enzyme cuts the labeled probe, the probe emits a detectable fluorescence signal.

Mutations or polymorphisms can also be detected using allele-specific hybridization followed by a MALDI-TOF-MS detection of the different hybridization products. In the preferred embodiment, the detection of the enhanced or amplified nucleic acids representing the different alleles is performed using matrix-assisted laser desorption ionization/time-of-flight (MALDI-TOF) mass spectrometric (MS) analysis described in the Examples below. This method differentiates the alleles based on their different mass and can be applied to analyze the products from the various above-described primer-extension methods or the INVADER® process.

In one embodiment, a haplotyping method useful according to the present invention is a physical separation of alleles by cloning, followed by sequencing. Other methods of haplotyping, useful according to the present invention include, but are not limited to monoallelic mutation analysis (MAMA) (Papadopoulos et al. (1995) Nature Genet. 11:99-102) and carbon nanotube probes (Woolley et al. (2000) Nature Biotech. 18:760-763). U.S. Patent Application No. US 2002/0081598 also discloses a useful haplotying method which involves the use of PCR amplification.

Computational algorithms such as expectation-maximization (EM), subtraction and PHASE are useful methods for statistical estimation of haplotypes (see, e.g., Clark, A. G. Inference of haplotypes from PCR-amplified samples of diploid populations. Mol Biol Evol 7, 111-22. (1990); Stephens, M., Smith, N. J. & Donnelly, P. A new statistical method for haplotype reconstruction from population data. Am J Hum Genet 68, 978-89. (2001); Templeton, A. R., Sing, C. F., Kessling, A. & Humphries, S. A cladistic analysis of phenotype associations with haplotypes inferred from restriction endonuclease mapping. II. The analysis of natural populations. Genetics 120, 1145-54. (1988)).

Other Assays

Other methods for genetic screening can be used within the scope of the present invention, for example, to detect mutations in genomic DNA, cDNA and/or RNA samples. Methods commonly used, or newly developed or methods yet unknown are encompassed for used in the present invention. Examples of newly discovered methods include for example, but are not limited to; SNP mapping (Davis et al, Methods Mol Biology, 2006; 351; 75-92); Nanogen Nano Chip, (keen-Kim et al, 2006; Expert Rev Mol Diagnostic, 6; 287-294); Rolling circle amplification (RCA) combined with circularable oligonucleotide probes (c-probes) for the detection of nucleic acids (Zhang et al, 2006: 363; 61-70), luminex XMAP system for detecting multiple SNPs in a single reaction vessel (Dunbar S A, Clin Chim Acta, 2006; 363; 71-82; Dunbar et al, Methods Mol Med, 2005; 114:147-1471) and enzymatic mutation detection methods (Yeung et al, Biotechniques, 2005; 38; 749-758).

Methods used to detect point mutations include denaturing gradient gel electrophoresis ("DGGE"), restriction fragment length polymorphism analysis ("RFLP"), chemical or enzymatic cleavage methods, direct sequencing of target regions amplified by PCR (see above), single strand confirmation polymorphism analysis ("SSCP") and other methods well known in the art.

One method of screening for point mutations is based on RNase cleavage of base pair mismatches in RNA/DNA or RNA/RNA heteroduplexes. As used herein, the term "mismatch" is defined as a region of one or more unpaired or mispaired nucleotides in a double-stranded RNA/RNA, RNA/DNA or DNA/DNA molecule. This definition thus includes mismatches due to insertion/deletion mutations, as well as single or multiple base point mutations.

In such embodiments, protection from cleavage agents (such as a nuclease, hydroxylamine or osmium tetroxide and with piperidine) can be used to detect mismatched bases in RNA/RNA DNA/DNA, or RNA/DNA heteroduplexes (see, e.g., Myers et al. (1985) Science 230:1242). In general, the technique of "mismatch cleavage" starts by providing heteroduplexes formed by hybridizing a control nucleic acid, which is optionally labeled, e.g., RNA or DNA, comprising a nucleotide sequence of the allelic variant of the gene of interest with a sample nucleic acid, e. g., RNA or DNA, obtained from a tissue sample. The double-stranded duplexes are treated with an agent which cleaves single-stranded regions of the duplex such as duplexes formed based on basepair mismatches between the control and sample strands. For instance, RNA/DNA duplexes can be treated with RNase and DNA/DNA hybrids treated with S1 nuclease to enzymatically digest the mismatched regions. In other embodiments, either DNA/DNA or RNA/DNA duplexes can be treated with hydroxylamine or osmium tetroxide and with piperidine in order to digest mismatched regions. After digestion of the mismatched regions, the resulting material is then separated by size on denaturing polyacrylamide gels to determine whether the control and sample nucleic acids have an identical nucleotide sequence or in which nucleotides they are different. See, for example, U.S. Pat. No. 6,455,249, Cotton et al. (1988) Proc. Natl. Acad. Sci. USA 85:4397; Saleeba et al. (1992) Methods Enzy. 217:286-295. In another embodiment, the control or sample nucleic acid is labeled for detection.

U.S. Pat. No. 4,946,773 describes an RNaseA mismatch cleavage assay that involves annealing single-stranded DNA or RNA test samples to an RNA probe, and subsequent treatment of the nucleic acid duplexes with RNaseA. For the detection of mismatches, the single-stranded products of the RNaseA treatment, electrophoretically separated according to size, are compared to similarly treated control duplexes. Samples containing smaller fragments (cleavage products) not seen in the control duplex are scored as positive.

Other investigators have described the use of RNaseI in mismatch assays. The use of RNaseI for mismatch detection is described in literature from Promega Biotech. Promega markets a kit containing RNaseI that is reported to cleave three out of four known mismatches.

In other embodiments, alterations in electrophoretic mobility is used to identify the particular allelic variant. For example, single strand confirmation polymorphism (SSCP) can be used to detect differences in electrophoretic mobility between mutant and wild type nucleic acids (Orita et al. (1989) Proc Natl. Acad. Sol USA 86:2766; Cotton (1993) Mutat. Res. 285:125-144 and Hayashi (1992) Genet Anal Tech Appl 9:73-79). Single-stranded DNA fragments of sample and control nucleic acids are denatured and allowed to renature. The secondary structure of single-stranded nucleic acids varies according to sequence, the resulting alteration in electrophoretic mobility enables the detection of even a single base change. The DNA fragments can be labeled or detected with labeled probes. The sensitivity of the assay can be enhanced by using RNA (rather than DNA), in which the secondary structure is more sensitive to a change in sequence. In another preferred embodiment, the subject method utilizes heteroduplex analysis to separate double stranded heteroduplex molecules on the basis of changes in electrophoretic mobility (Keen et al. (1991) Trends Genet. 7:5).

Gel Migration Single strand conformational polymorphism (SSCP; M. Orita et al., Genomics 5:874-879 (1989); Huinphfies et al., In: Molecular Diagnosis of Genetic Diseases, R. Elles, ed. pp 321-340 (1996)) and temperature gradient gel electrophoresis (TGGE; R. M. Wartell et al., Nucl. Acids Res. 18:2699-2706 (1990)) are examples of suitable gel migration-based methods for determining the identity of a polymorphic site. In SSCP, a single strand of DNA will adopt a confirmation that is uniquely dependent of its sequence composition. This confirmation is usually different, if even a single base is changed. Thus, certain embodiments of the present invention, SSCP can be utilized to identify polymorphic sites, as wherein amplified products (or restriction fragments thereof of the target polynucleotide are denatured, then run on a non-denaturing gel. Alterations in the mobility of the resultant products are thus indicative of a base change. Suitable controls and knowledge of the "normal" migration patterns of the wild-type alleles can be used to identify polymorphic variants.

In yet another embodiment, the identity of the allelic variant is obtained by analyzing the movement of a nucleic acid comprising the polymorphic region in polyacrylamide gels containing a gradient of denaturant, which is assayed using denaturing gradient gel electrophoresis (DGGE) (Myers et al. (1985) Nature 313:495). When DGGE is used as the method of analysis, DNA will be modified to insure that it does not completely denature, for, example by adding a GC clamp of approximately 40 bp of high-melting GC rich DNA by PCR. In a further embodiment, a temperature gradient is used in place of a denaturing agent gradient to identify differences in the mobility of control and sample DNA (Rosenbaum and Reissner (1987) Biophys Chem 265:1275).

Others have described using the MutS protein or other DNA-repair enzymes for detection of single-base mismatches. Alternative methods for detection of deletion, insertion or substitution mutations that can be used in the practice of the present invention are disclosed in U.S. Pat. Nos. 5,849,483, 5,851,770, 5,866,337, 5,925,525 and 5,928,870, each of which is incorporated herein by reference in its entirety.

Further Examples of SNP Screening Methods

Spontaneous mutations that arise during the course of evolution in the genomes of organisms are often not immediately transmitted throughout all of the members of the species, thereby creating polymorphic alleles that co-exist in the species populations. Often polymorphisms are the cause of genetic diseases. Several classes of polymorphisms have been identified. For example, variable nucleotide type polymorphisms (VNTRs), arise from spontaneous tandem duplications of di- or trinucleotide repeated motifs of nucleotides. If such variations alter the lengths of DNA fragments generated by restriction endonuclease cleavage, the variations are referred to as restriction fragment length polymorphisms (RFLPs). RFLPs are widely used in human and animal genetic analyses.

In one embodiment, restriction enzymes can be utilized in identifying a polymorphic site in "restriction fragment length polymorphism" (RFLP) analysis (Lentes et al., Nucleic Acids Res. 16:2359 (1988); and C. K. McQuitty et al., Hum. Genet. 93:225 (1994)). In RFLP, at least one target polynucleotide is digested with at least one restriction enzyme and the resultant "restriction fragments" are separated based on mobility in a gel. Typically, smaller fragments migrate faster than larger fragments. Consequently, a target polynucleotide that contains a particular restriction enzyme recognition site will be digested into two or more smaller fragments, which will migrate faster than a larger fragment lacking the restriction enzyme site. Knowledge of the nucleotide sequence of the target polynucleotide, the nature of the polymorphic site, and knowledge of restriction enzyme recognition sequences guide the design of such assays. In another embodiment of the present invention, restriction site analysis of particular nucleotide sequence by restriction enzymes the identity of a nucleotide at a polymorphic site is determined by the presence or absence of a restriction enzyme site. A large number of restriction enzymes are known in the art and, taken together, they are capable of recognizing at least one allele of many polymorphisms.

However, such single nucleotide polymorphisms (SNPs) rarely result in changes in a restriction endonuclease site. Thus, SNPs are rarely detectable by restriction fragment length analysis. SNPs are the most common genetic variations and occur once every 100 to 300 bases and several SNP mutations have been found that affect a single nucleotide in a protein-encoding gene in a manner sufficient to actually cause a genetic disease. SNP diseases are exemplified by hemophilia, sickle-cell anemia, hereditary hemochromatosis, late-onset Alzheimer's disease etc.

In context of the present invention, polymorphic mutations that affect the activity and/or levels of the EGF gene products will be determined by a series of screening methods. In important embodiments of the present invention uses screening methods aimed at identifying SNPs that affect the inducibility, activity and/or level of the EGF gene products in in vitro or in vivo assays. The other set of screening methods will then be performed to screen an individual for the occurrence of the SNPs identified above. To do this, a sample (such as blood or other bodily fluid or tissue sample) will be taken from a subject for genotype analysis.

SNPs can be the result of deletions, point mutations and insertions. In general any single base alteration, whatever the cause, can result in a SNP. The greater frequency of SNPs means that they can be more readily identified than the other classes of polymorphisms. The greater uniformity of their distribution permits the identification of SNPs "nearer" to a particular Gait of interest. The combined effect of these two attributes makes SNPs extremely valuable. For example, if a particular Gait (e.g., increased level of EGF RNA) reflects a mutation at a particular locus, then any polymorphism that is linked to the particular locus can be used to predict the probability that an individual will be exhibit that Wait. In some cases, the SNP can be the cause of the Gait.

Several methods have been developed to screen polymorphisms and some examples are listed below. The reference of Kwok and Chen (2003) and Kwok (2001) provide overviews of some of these methods, both of these references are specifically incorporated by reference.

Examples of identifying polymorphisms and applying that information in a way that yields useful information regarding patients can be found, for example, in U.S. Pat. No. 6,472,157; U.S. Patent Application Publications 20020016293, 20030099960, 20040203034; WO 0180896, all of which are hereby incorporated by reference.

Linkage Disequilibrium

Polymorphisms in linkage disequilibrium with the polymorphism at the 61 locus of the EGF gene can also be used with the methods of the present invention. "Linkage disequilibrium" ("LD" as used herein, though also referred to as "LED" in the art) refers to a situation where a particular combination; of alleles (i.e., a variant form of a given gene) or polymorphisms at two loci appears more frequently than would be expected by chance. "Significant" as used in respect to linkage disequilibrium, as determined by one of skill in the art, is contemplated to be a statistical p or o value that can be 0.25 or 0.1 and can be 0.1, 0.05. 0.001, 0.00001 or less. The relationship between EGF haplotypes and the expression level of the EGF proteins can be used to correlate the genotype (i.e., the genetic make up of an organism) to a phenotype (i.e., the physical traits displayed by an organism or cell). "Haplotype" is used according to its plain and ordinary meaning to one skilled in the art. It refers to a collective genotype of two or more alleles or polymorphisms along one of the homologous chromosomes.

SNPs relating to the expression of EGF function can be characterized by the use of any of these methods or suitable modification thereof. Such methods include the direct or indirect sequencing of the site, the use of restriction enzymes where the respective alleles of the site create or destroy a restriction site, or the use of allele-specific hybridization probes.

The term "allele-specific PCR" refers to PCR techniques where the primer pairs are chosen such that amplification is dependent upon the input template nucleic acid containing the polymorphism of interest. In such embodiments, primer pairs are chosen such that at least one primer is an allele-specific oligonucleotide primer. In some sub-embodiments of the present invention, allele-specific primers are chosen so that amplification creates a restriction site, facilitating identification of a polymorphic site. In other embodiments of the present invention, amplification of the target polynucleotide is by multiplex PCR (Wallace et al. (PCT Application W089/10414)). Through the use of multiplex PCR, a multiplicity of regions of a target polynucleotide can be amplified simultaneously. This is particularly advantageous in embodiments where more than one SNP is to be detected.

If the polymorphic region is located in the coding region of the gene of interest, yet other methods than those described above can be used for determining the identity of the allelic variant. For example, identification of the allelic variant, which encodes a mutated signal peptide, can be performed by using an antibody specifically recognizing the mutant protein in, e.g., immunohistochemistry or immunoprecipitation. Antibodies to the wild-type or signal peptide mutated forms of the signal peptide proteins can be prepared according to methods known in the art.

In another embodiment, multiplex PCR procedures using allele-specific primers can be used to simultaneously amplify multiple regions of a target nucleic acid (PCT Application W089/10414), enabling amplification only if a particular allele is present in a sample. Other embodiments using alternative primer-guided nucleotide incorporation procedures for assaying polymorphic sites in DNA can be used, and have been described (Komher, J. S. et al., Nucl. Acids. Res. 17:7779-7784 (1989); Sokolov, B. P., Nucl. Acids Res. 18:3671 (1990); Syvanen, A.-C., et al., Genomics 8:684-692 (1990); Kuppuswamy, M. N. et al., Proc. Nad. Acad. Sci. (U.S.A) 88:1143-1147 (1991); Bajaj et al. (U.S. Pat. No. 5,846,710); Prezant, T. R. et al., Hum Mutat. 1: 159-164 (1992); Ugozzoli, L. et al., GATA 9:107-112 47 (1992); Nyr6n, P. et al., Anal. Biochem. 208:171-175 (1993)).

Other known nucleic acid amplification procedures include transcription-based amplification systems (Malek, L. T. et al., U.S. Pat. No. 5,130,238; Davey, C. et al., European Patent Application 329,822; Schuster et al.) U.S. Pat. No. 5,169,766; Miller, H. I. et al., PCT-Application W089/06700; Kwoh, D. et al., Proc. Natl. Acad Sci. (U.S.A) 86:1173 Z1989); Gingeras, T. R. et al., PCT Application W088/10315)), or isothermal amplification methods (Walker, G. T. et al., Proc. Natl. Acad Sci. (U.S.A) 89:392-396 (1992)) can also be used.

Solid Supports

Solid supports containing oligonucleotide probes for identifying the alleles, including polymorphic alleles, of the present invention can be filters, polyvinyl chloride dishes, silicon or glass based chips, etc. Such wafers and hybridization methods are widely available, for example, those disclosed by Beattie (WO 95/11755). Any solid surface to which oligonucleotides can be bound, either directly or indirectly, either covalently or noncovalently, can be used. A preferred solid support is a high density array or DNA chip. These contain a particular oligonucleotide probe in a predetermined location on the array. Each predetermined location can contain more than one molecule of the probe, but each molecule within the predetermined location has an identical sequence. Such predetermined locations are termed features. There can be, for example, about 2, 10, 100, 1000 to 10,000; 100,000, 400,000 or 1,000,000 of such features on a single solid support. The solid support, or the area within which the probes are attached can be on the order of a square centimeter.

Oligonucleotide probe arrays can be made and used according to any techniques known in the art (see for example, Lockchart et al. (1996), Nat. Biotechnol. 14: 1675-1680; McGall et al. (1996), Proc. Nat. Acad. Sci. USA 93: 13555-13460). Such probe arrays can contain at least two or more oligonucleotides that are complementary to or hybridize to two or more of the SNPs described herein.

Databases

The present invention includes databases containing information concerning polymorphic alleles associated with the coronary artery disease and coronary syndrome, for instance, information concerning polymorphic allele frequency and strength of the association of the allele with myocardial infarction and the like. Databases can also contain information associated with a given polymorphism such as descriptive information about the probability of association of the polymorphism with prediction of clinical phenotype, for example the likelihood of responsiveness to adenosine treatment and/or prediction of infarct size on myocardial infarction. Other information that can be included in the databases of the present invention include, but is not limited to, SNP sequence information, descriptive information concerning the clinical status of a tissue sample analyzed for SNP haplotype, or the subject from which the sample was derived. The database can be designed to include different parts, for instance a SNP frequency database and a SNP sequence database. Methods for the configuration and construction of databases are widely available, for instance, see Akerblom et al., (1999) U.S. Pat. No. 5,953,727, which is herein incorporated by reference in its entirety.

The databases of the present invention can be linked to an outside or external database. In a preferred embodiment, the external database can be the HGBASE database maintained by the Karolinska Institute, The SNP Consortium (TSC) and/or the databases maintained by the National Center for Biotechnology Information (NCBI) such as GenBank.

The databases of the present invention can also be used to present information identifying the polymorphic alleles in a subject and such a presentation can be used to predict the likelihood that the subject will develop cancer. Further, the databases of the present invention can comprise information relating to the expression level of one or more of the genes associated with the polymorphic alleles of the invention.

Methods of Treatment

The present invention further provides methods of treating subjects identified, using the methods of the present invention, to be at risk of developing or afflicted with cancer, wherein the subjects identified to have variances in the EGF gene and/or increased levels of expression EGF gene product identify subjects with an increased risk of getting or developing cancer. In one embodiment, the method comprises (a) determining the identity of the allelic variant; and (b) administering to the subject an effective amount of a compound that provides therapeutic benefits for the specific allelic variant. The method comprises isolating a suitable cell or tissue sample from the patient and screening for a genomic polymorphism or genotype that has been correlated by the Applicants to be clinically significant.

This invention provides a method for selecting a therapeutic regimen or determining if a certain therapeutic regimen is more likely to treat a cancer or is the appropriate chemotherapy for that patient than other available chemotherapies. In general, a therapy is considered to "treat" cancer if it provides one or more of the following treatment outcomes: reduce or delay recurrence of the cancer after the initial therapy; increase median survival time or decrease metastases. The method is particularly suited to determining which patients will be responsive or experience a positive treatment outcome to a chemotherapeutic regimen involving administration of a fluoropyrimidine drug such as 5-FU or a platinum drug such as oxaliplatin or cisplatin. Alternatively, the chemotherapy includes administration of a topoisomerase inhibitor such as irinotecan. In a yet further embodiment, the therapy comprises administration of an antibody (as broadly defined herein), ligand or small molecule that binds the Epidermal Growth Factor Receptor (EGFR).

Chemoprevention strategies that target the EGF-EGFR pathway have promise as a novel approach for patients with cirrhosis who are at risk for HCC. For example, Schiffer et al. demonstrated in a rat model in which DEN induces cirrhosis within 12 weeks and subsequent HCC at 18 weeks that concurrent treatment with the selective EGFR tyrosine kinase inhibitor gefitinib during weeks 12-18 significantly reduced the formation of HCC nodules (21).

In one aspect, after determining that a subject is at risk of developing cancer due to elevated EGF gene product levels (for example, elevated mRNA EGF and/or elevated EGF protein) and/or variances in the EGF gene that results in increased EGF expression, then a strategy to prevent the cancer can initiated, for example administration of an anti-cancer-therapy to the subject. In some embodiments, the anti-cancer therapy is a chemotherapeutic agent, radiotherapy etc. Such anti-cancer therapies are disclosed herein, as well as others that are well known by persons of ordinary skill in the art and are encompassed for use in the present invention. In some embodiments the anti-cancer therapy, or cancer prevention strategy is targets the EGF/EGFR pathway, and in other embodiments, the anti-cancer therapy or cancer prevention strategy does not target the EGF/EGFR pathway.

The term "anti-cancer therapy" or "anti-cancer agent" or "anti-cancer drug" is any agent, compound or entity that would be capably of negatively affecting the cancer in the patient, for example killing cancer cells, inducing apoptosis in cancer cells, reducing the growth rate of cancer cells, reducing the number of mestatic cells, reducing tumor size, inhibiting tumor growth, reducing blood supply to a tumor or cancer cells, promoting an immune response against cancer cells or a tumor, preventing or inhibiting the progression of cancer, or increasing the lifespan of the subject with cancer. Anti-cancer therapy includes biological agents (biotherapy), chemotherapy agents, and radiotherapy agents. The combination of chemotherapy with biological therapy is known as biochemotherapy.

Treatment can include prophylaxis, including agents which slow or reduce the risk of cancer. In other embodiments, the treatments are any means to prevent the proliferation of cancerous cells. In some embodiments, the treatment is an agent which suppresses the EGF-EGFR pathway, for example but not limited to inhibitors and agents of EGFR. Inhibitors of EGFR include, but are not limited to, tyrosine kinase inhibitors such as quinazolines, such as PID 153035, 4-(3-chloroanilino)quinazoline, or CP-358,774, pyridopyrimidines, pyrimidopyrimidines, pyrrolopyrimidines, such as CGP 59326, CGP 60261 and CGP 62706, and pyrazolopyrimidines, 4-(phenylamino)-7H-pyrrolo[2,3-d]pyrimidines (Traxler et al., (1996) J. Med Chem 39:2285-2292), curcumin (diferuloyl methane) (Laxmin arayana, et al., (1995), Carcinogen 16:1741-1745), 4,5-bis(4-fluoroanilino)phthalimide (Buchdunger et al. (1995) Clin. Cancer Res. 1:813-821; Dinney et al. (1997) Clin. Cancer Res. 3:161-168); tyrphostins containing nitrothiophene moieties (Brunton et al. (1996) Anti Cancer Drug Design 11:265-295); the protein kinase inhibitor ZD-1 839 (AstraZeneca); CP-358774 (Pfizer, Inc.); PD-01 83805 (Warner-Lambert), EKB-569 (Torrance et al., Nature Medicine, Vol. 6, No. 9, September 2000, p. 1024), HKI-272 and HKI-357 (Wyeth); or as described in International patent application WO05/018677 (Wyeth); W099/09016 (American Cyanamid); W098/43960 (American Cyanamid); WO 98/14451; WO 98/02434; W097/38983 (Warener Labert); W099/06378 (Warner Lambert); W099/06396 (Warner Lambert); W096/30347 (Pfizer, Inc.); W096/33978 (Zeneca); W096/33977 (Zeneca); and W096/33980 (Zeneca), WO 95/19970; U.S. Pat. App. Nos. 2005/0101618 assigned to Pfizer, 2005/0101617, 20050090500 assigned to OSI Pharmaceuticals, Inc.; all herein incorporated by reference. Further useful EGFR inhibitors are described in U.S. Pat. App. No. 20040127470, particularly in tables 10, 11, and 12, and are herein incorporated by reference.

In other embodiments, EGFR-inhibiting agents can be used, for example, but are not limited to, Gefitinib (compound ZD1839 developed by AstraZeneca UK Ltd.; available under the tradename IRESSA; hereinafter "IRESSA") and Erlotinib (compound OSI-774 developed by Genentech, Inc. and OSI Pharmaceuticals, Inc.; available under the tradename TARCEVA; hereinafter "TARCEVA"); the monoclonal antibodies cetuximab (Erbitux; ImmClone Systems Inc/Merck KGaA), matuzumab (Merck KGaA) and anti-EGFR 22Mab (ImClone Systems Incorporated of New York, N.Y., USA), for egf/r3 MAb (Cuban Institute of Oncology; Hybridoma, 2001, Vol. 20, No. 2: 131-136), panitumumab/ABX-EGF (Abgenix/Cell Genesys), nimotuzumab ((TheraCIM-hR3) YM BioSciences Inc. Mississauga, Ontario, Canada), EMD-700, EMD-7200, EMD-5590 (Merck KgaA), E7.6.3 (Abgenix; Cancer Research 59, 1236-1243, 1999), Mab 806 (Ludwig Institute), MDX-103, MDX-447/H-477 (Medarex Inc. of Annandale, N.J., USA and Merck KgaA), and the compounds ZD-1834, ZD-1838 and ZD-1839 (AstraZeneca), PKI-166 (Novartis), PKI-166/CGP-75166 (Novartis), PTK 787 (Novartis), AEE788 (Novartis), CP 701 (Cephalon), leflunomide (Pharmacia/Sugen), CI-1033/PD-169414/PD- 183805/Canertinib (Pfizer), CP-358774 (Pfizer), PD-168393, PD-158780, PD-160678 (Parke-Davis), CL-387,785 ((N-[4-[(3-bromophenyl)amino]-6-quinazolinyl]-2-butynamide; C. M. Discafani, et al.; Biochem. Pharmacol. 57:917 (1999)), BBR-1611 (Boehringer Mannheim GmbH/Roche), Naamidine A (Bristol Myers Squibb), RC-3940-II (Pharmacia), BIBX-1382 (Boehringer Ingelheim), OLX-103 (Merck & Co. of Whitehouse Station, N.J., USA), VRCTC-310 (Ventech Research), EGF fusion toxin (Seragen Inc. of Hopkinton, Mass.), DAB-389 (Seragen/Lilgand), ZM-252808 (Imperical Cancer Research Fund), RG-50864 (INSERM), LFM-A12 (Parker Hughes Cancer Center), WHI-P97 (Parker Hughes Cancer Center), GW-282974, GW2016 (Glaxo), KT-8391 (Kyowa Hakko) and EGFR Vaccine (York Medical/Centro de Immunologia Molecular (CIM)), EXEL 7647/EXEL 0999, XL647 (Exelixis), AG1478 (4-(3-Chloroanillino)-6,7-dimethoxyquinazoline), AG879 (3,5-Di-t-butyl-4-hydroxy-benzylidene)thiocyanoacetamide), ICR15, ICR16, and ICR80 (Int J Cancer. 1998 Jan. 19; 75(2):310-6.), ICR62 (Modjtahedi et al. Br J Cancer 1996; 73:228-35.), CGP 59326A (Novartis), BMS-599626 (Bristol-Myers Squibb)). These and other EGFR-inhibiting agents can be used in the present invention.

In an alternative embodiment, the some inhibitors of ErbB2 also inhibit EGFR and can be useful in the methods of the present invention. ErbB2 inhibitors include CI-1003, CP-724,714, CP-654577 (Pfizer, Inc.), GW-2016, GW-282974, and lapatinib/GW-572016 (Glaxo Wellcome plc), TAK-165 (Takeda), AEE788 (Novartis), EKB-569, HKI-272 and HKI-357 (Wyeth) (Wyeth-Ayerst), EXEL 7647/EXEL 0999 (EXELIXIS) and the monoclonal antibodies Trastuzumab (tradename HERCEPTIN), 2C4 (Genentech), AR-209 (Aronex Pharmaceuticals Inc. of The Woodlands, Tex., USA), pertuzumab (tradename OMNITARG; Genentech), BMS-599626 (Bristol-Myers Squibb) and 2B-1 (Chiron). For example those indicated in U.S. Pat. Nos. 6,867,201, 6,541,481, 6,284,764, 5,587,458 and 5,877,305; WO 98/02434, WO 99/35146, WO 99/35132, WO 98/02437, WO 97/13760, WO 95/19970, which are all hereby incorporated herein in their entireties by reference. The ErbB2 receptor inhibitor compounds and substance described in the aforementioned PCT applications, U.S. patents, and U.S. patent applications, as well as other compounds and substances that inhibit the ErbB2 receptor, can be used with the compound of the present invention in accordance with the present invention.

In an alternative embodiment, the anti-cancer therapy is a therapy that suppresses the activity of the EGF-EGFR pathway, for example but not limited to the administration of an antibody, fragment, variant or derivative thereof that binds EGFR. In another embodiment, compounds useful in the method of the present invention are antibodies which interfere with kinase signaling via EGFR, including monoclonal, chimeric, humanized, midi antibodies, recombinant antibodies and fragments thereof which are characterized by their ability to inhibit the kinase activity of the EGFR and which have low toxicity.

In another embodiment, the anti-cancer therapy includes a chemotherapeutic regimen further comprises radiation therapy. In an alternate embodiment, the therapy comprises administration of an anti-EGFR antibody or biological equivalent thereof.

In some embodiments, the anti cancer treatment comprises the administration of a chemotherapeutic drug selected from the group consisting of fluoropyrimidine (e.g., 5-FU), oxaliplatin, CPT-11, (e.g., irinotecan) a platinum drug or an anti EGFR antibody, such as the cetuximab antibody or a combination of such therapies, alone or in combination with surgical resection of the tumor. In yet a further aspect, the treatment compresses radiation therapy and/or surgical resection of the tumor masses.

The antibodies also are characterized by their ability to specifically bind to an EGFR epitope. The antibodies useful in the present invention can be generated using techniques well known in the art and are well-described in the literature and can be easily performed by one of ordinary skill in the art.

Antibodies can also be used in immunohistochemical assays to detect the presence or expression level of a protein of interest. They are further useful to detect the presence or absence of EGFR in a patient sample. In these and other aspects of this invention, it will be useful to detectably or therapeutically label the antibody. Methods for conjugating antibodies to these agents are known in the art. For the purpose of illustration only, antibodies can be labeled with a detectable moiety such as a radioactive atom, a chromophore, a fluorophore, or the like. With respect to preparations containing antibodies covalently linked to organic molecules, they can be prepared using suitable methods known by persons skilled in the art, such as by reaction with one or more modifying agents. Examples of such include modifying and activating groups.

In alternative embodiments, the subject is administered a treatment or therapeutic compound that functions through the activation of adenosine pathway, and includes compounds already known by persons skilled in the art and compounds that have yet to be developed.

In a further aspect, a method of preventing or reducing the risk of cancer, in particular hepatocellular carcinoma in subjects with liver disease and/or cirrhosis is provided that includes administering to a subject an anti-cancer (e.g. cancer prevention) therapy, where the subject is identified to have susceptibility alleles or any subject with at least a allele of 61A>G in the EGF gene and/or a subject identified to have elevated levels of EGF gene product (e.g elevated EGF mRNA or elevated EGF protein) in a biological sample as compared to a reference biological sample. In some embodiments, the biological sample is blood or liver tissue. In some embodiments, the anti-cancer therapy is administered at a predetermined point or period of intervention. In some embodiments, the anti-cancer therapy is an agent that suppresses or reduces the activity of the EGF-EGFR pathway.

The compounds used in connection with the treatment methods of the present invention are administered and dosed in accordance with good medical practice, taking into account the clinical condition of the individual subject, the site and method of administration, scheduling of administration, patient age, sex, body weight and other factors known to medical practitioners. The pharmaceutically "effective amount" for purposes herein is thus determined by such considerations as are known in the art. The amount must be effective to achieve improvement including, but not limited to, improved survival rate or more rapid recovery, or improvement or elimination of symptoms and other indicators as are selected as appropriate measures by those skilled in the art.

The methods of the present invention are useful for the early detection of individuals susceptible to developing cancer. In some embodiments, the present invention is useful for the identification of subjects with liver disease and/or cirrhosis that have increased risk of developing hepatocellular carcinoma. Thus, treatment can be initiated early, e.g. before or at the beginning of the onset of symptoms, for example before the onset of the cancer and/or hepatocellular cancer. In alternative embodiments, the treatment can be administered to a subject that has, or is at risk of developing cancer, for example hepatocellular cancer (HCC). In alternative embodiments, the treatment can be administered prior to, during, concurrent or post the development of cancer and/or hepatocellular cancer (HCC). The dosage required at these early stages will be lower than those needed at later stages of disease where the symptoms are severe. Such dosages are known to those of skill in the art and can be determined by the physician in response to the particular patient.

In some embodiments, where a subject with liver disease, for example cirrhosis, is identified as having increased risk of having or developing cancer, for example HCC, using the methods of the present invention, a clinician can recommended a treatment regimen to reduce or lower EGF expression levels in the subject. Accordingly, the methods of the present invention provide preventative methods to reduce the risk of subject getting cancer, for example HCC, which the subject as liver disease, for example cirrhosis.

In another embodiment, a subject with liver disease, for example cirrhosis can be monitored for levels of EGF expression or gene product before, during and after such a treatment regimen (ie administration of a preventative therapy to reduce EGF levels), and where a subject is identified to not have lowered EGF gene product levels (and thus still is at risk of developing HCC) after a period of time of being administered such a treatment regimen, then the treatment regimen could be modified, for example the subject could be administered (i) a different protective therapy or drug to reduce EGF levels, (ii) an altered dose or (iii) a combination therapies etc. Alternatively, if the extent to which EGF levels are lowered in some patients with liver disease administered such treatment regimens aimed at lowering EGF levels, and the amount the EGF levels differs between other subjects with liver disease, possibly due to differences in drug dosage, then appropriate drug dosing would benefit from measurement of EGF levels.

Therapeutic compositions comprising one or more anti-cancer agents can be optionally tested for a therapeutically effective amount as defined herein by use in one or more appropriate in vitro and/or in vivo animal models of disease, to confirm efficacy, tissue metabolism, and to estimate dosages, according to methods well known in the art. In particular, dosages of an anti-cancer therapy can be initially determined by activity, stability or other suitable measures of treatment vs. non-treatment (e.g., comparison of treated vs. untreated cells or animal models), in a relevant assay. Formulations are administered at a rate determined by the LD50 of the relevant formulation, and/or observation of any side-effects of the nucleic acids at various concentrations, e.g., as applied to the mass and overall health of the patient. Administration can be accomplished via single or divided doses.

In vitro models can be used to determine the effective doses of the anti-cancer therapies to treat subjects identified as having an increased risk of developing cancer by the methods as disclosed herein. Suitable in vitro models include, but are not limited to, proliferation assays of cultured tumor cells, growth of cultured tumor cells in soft agar (see Freshney, (1987) Culture of Animal Cells: A Manual of Basic Technique, Wily-Liss, New York, N.Y. Ch 18 and Ch 21), tumor systems in nude mice as described in Giovanella et al., J. Natl. Can. Inst., 52: 921-30 (1974), mobility and invasive potential of tumor cells in Boyden Chamber assays as described in Pilkington et al., Anticancer Res., 17: 4107-9 (1997), and angiogenesis assays such as induction of vascularization of the chick chorioallantoic membrane or induction of vascular endothelial cell migration as described in Ribatta et al., Intl. J. Dev. Biol., 40: 1189-97 (1999) and Li et al., Clin. Exp. Metastasis, 17:423-9 (1999), respectively. Suitable tumor cells lines are available, e.g. from American Type Tissue Culture Collection catalogs.

In vivo models can also be used and are the preferred models to determine the effective doses of the anti-cancer therapies to treat subjects identified as having an increased risk of developing cancer by the methods as disclosed herein. Suitable in vivo models include, but are not limited to, mice that carry a mutation in the KRAS oncogene (Lox-Stop-Lox K-Ras$^{G12D}$ mutants, Kras2$^{tm4Tyj}$) available from the National Cancer Institute (NCI) Frederick Mouse Repository. Other mouse models known in the art and that are available include but are not limited to models for gastrointestinal cancer, hematopoietic cancer, lung cancer, mammary gland cancer, nervous system cancer, ovarian cancer, prostate cancer, skin cancer, cervical cancer, oral cancer, and sarcoma cancer (see http://emice.nci.nih.gov/mouse_models/).

In determining the effective amount of the anti-cancer therapy to be administered to a subject identified as having an increased risk of developing cancer by the methods as disclosed herein, the can physician evaluate circulating plasma levels, formulation toxicities, and progression of the disease.

In some embodiments, where the anti-cancer therapy is a nucleic acid, the dose administered to a 70 kilogram patient is typically in the range equivalent to dosages of currently-used therapeutic antisense oligonucleotides such as Vitravene®. (fomivirsen sodium injection) which is approved by the FDA for treatment of cytomegaloviral RNA, adjusted for the altered activity or serum half-life of the relevant composition.

In some embodiments, the more than one cancer therapy can be administered to a subject identified as having an increased risk of developing cancer by the methods as disclosed herein, including any combination of known conventional anti-cancer therapies, including, but not limited to, antibody administration, vaccine administration, administration of cytotoxic agents, natural amino acid polypeptides, nucleic acids, nucleotide analogues, and biologic response modifiers. Two or more combined compounds may be used together or sequentially. For example, the nucleic acids can also be administered in therapeutically effective amounts as a portion of an anti-cancer cocktail. An anti-cancer cocktail is a mixture of the oligonucleotide or modulator with one or more anti-cancer drugs in addition to a pharmaceutically acceptable carrier for delivery. The use of anti-cancer cocktails as a cancer treatment is routine. Anti-cancer drugs that are well known in the art and can be used as a treatment in combination with the nucleic acids described herein include, but are not limited to: Actinomycin D, Aminoglutethimide, Asparaginase, Bleomycin, Busulfan, Carboplatin, Carmustine, Chlorambucil, Cisplatin (cis-DDP), Cyclophosphamide, Cytarabine HCl (Cytosine arabinoside), Dacarbazine, Dactinomycin, Daunorubicin HCl, Doxorubicin HCl, Estramustine phosphate sodium, Etoposide (V16-213), Floxuridine, 5-Fluorouracil (5-Fu), Flutamide, Hydroxyurea (hydroxycarbamide), Ifosfamide, Interferon Alpha-2a, Interferon Alpha-2b, Leuprolide acetate (LHRH-releasing factor analog), Lomustine, Mechlorethamine HCl (nitrogen mustard), Melphalan, Mercaptopurine, Mesna, Methotrexate (MTX), Mitomycin, Mitoxantrone HCl, Octreotide, Plicamycin, Procarbazine HCl, Streptozocin, Tamoxifen citrate, Thioguanine, Thiotepa, Vinblastine sulfate, Vincristine sulfate, Amsacrine, Azacitidine, Hexamethylmelamine, Interleukin-2, Mitoguazone, Pentostatin, Semustine, Teniposide, and Vindesine sulfate.

Inflammatory Diseases to be Treated

Subjects amenable to being screened for the presence of mutations and/or polymorphisms in the EGF gene, and/or levels of the EGF protein or mRNA are subjects with an inflammatory disease or disorder. As disclosed herein, an inflammatory disorder or disease can be a liver disease.

Without being bound to theory, subjects can be identified with liver disease by a number of clinical manifestations of the disease. Examples of characteristic manifestations of liver disease include jaundice (a yellowish discoloration of the skin and whites of the eyes), cholestasis (reduction or stoppage of bile flow), liver enlargement, portal hypertension (abnormally high blood pressure in the veins that bring blood from the intestine to the liver), ascites (accumulation of fluid in the abdominal cavity), hepatic encephalopathy (deterioration of brain function due to buildup of toxic substances normally removed by the brain), and liver failure.

One of ordinary skill in the art can identify a subject with liver disease, and some of the symptoms of liver disease are subtle, and include, for example, symptoms of fatigue, a feeling of unwellness, loss of appetite, and mild weight loss. However, these symptoms are also typical of many other diseases. Thus, liver disease can easily be overlooked, particularly in its early stages.

Examples of liver diseases include, but are not limited to, cirrhosis, bilirubin metabolism, jaundice, syndromes of Gilbert's, Crigler-Najjar, Dubin-Johnson and Rotor; intrahepatic cholestasis, hepatomegaly, portal hypertension, ascites, Budd-Chiari syndrome, portal-systemic encephalopathy, fatty liver, steatosis, Reye's syndrome, liver diseases due to alcohol, alcoholic hepatitis or cirrhosis, fibrosis and cirrhosis, fibrosis and cirrhosis of the liver due to inborn errors of metabolism of exogenous substances, storage diseases, syndromes of Gaucher's, Zellewger's, Wilson's disease, acute or chronic hepatitis, chronic active hepatitis, viral hepatitis and its variants, inflammatory conditions of the liver due to viruses, bacteria, fungi, protozoa, helminthes, drug-induced disorders of the liver, chronic liver diseases like primary sclerosing cholangitis, alpha$_1$-antitrypsin-deficiency, primary biliary cirrhosis, postoperative liver disorders like intrahepatic cholestasis, hepatic granulomas, vascular liver disorders associated with systematic disease etc.

Some clinical symptoms of liver disease include, for example; Jaundice, a yellowish discoloration of the skin and whites of the eyes; Hepatomegaly (liver enlargement); ascites (fluid in the abdominal cavity); hepatic encephalopathy (confusion caused by deterioration of brain function due to buildup of toxic substances in the blood); gastrointestinal bleeding (bleeding from large, tortuous veins (varices) in the esophagus and stomach); portal hypertension (abnormally high blood pressure in the veins that bring blood from the intestine to the liver (branches of the portal vein); skin symptoms such as spiderlike blood vessels on the face and chest; red palms (bright red complexion); itching; blood abnormalities such as decreased number of red blood cells (anemia)) or decreased number of white blood cells (leukopenia), decreased number of platelets (thrombocytopenia) or a tendency to bleed (coagulopathy); hormonal abnormalities such as high levels of insulin but a poor response to it, leading to high blood sugar level; cessation of menstrual periods and decreased fertility in women; erectile dysfunction and feminization in men; heart and blood vessel abnormalities or an increased heart rate and amount of blood pumped; low blood pressure (hypotension); and other general symptoms such as fatigue, weakness, weight loss, poor appetite, nausea, fever, and abdominal pain.

In some embodiments, subjects amenable to detection of EGF polymorphisms or EGF levels by the methods as disclosed herein are subjects with an inflammatory disease such as liver disease. In some instances, one of ordinary skill in the art can detect a liver disease in a subject, such as for example by use of a liver panel test. A liver panel, also known as liver (hepatic) function tests or LFT, can be used in the methods as disclosed herein to detect, evaluate, and monitor liver disease or damage, and thus select for subjects with an inflammatory disease. A liver panel typically usually consists of seven tests that are run at the same time on a blood sample. These include: Alanine aminotransferase (ALT)—an enzyme mainly found in the liver; the best test for detecting hepatitis; Alkaline phosphatase (ALP)—an enzyme related to the bile ducts; often increased when they are blocked; Aspartate aminotransferase (AST)—an enzyme found in the liver and a few other places, particularly the heart and other muscles in the body; Bilirubin—two different tests of bilirubin often used together (especially if a person has jaundice): total bilirubin measures all the bilirubin in the blood; direct bilirubin measures a form that is conjugated (combined with another compound) in the liver; Albumin—measures the main protein made by the liver and tells whether or not the liver is making an adequate amount of this protein and Total Protein—measures albumin and all other proteins in blood, including antibodies made to help fight off infections. Additional tests that can be used to determine liver function or liver disease also include gamma-glutamyl transferase (GGT), lactic acid dehydrogenase (LDH), and prothrombin time (PT).

A liver panel is typically performed on a subject who has one or more of the following symptoms of a liver disease or disorder. Examples of a symptom of a liver disease or disorder include, for example jaundice, dark urine, or light-colored bowel movements; nausea, vomiting and/or diarrhea; loss of appetite; vomiting of blood; bloody or black bowel movements; swelling or pain in the belly; unusual weight change; or fatigue or loss of stamina. A liver panel can also be performed on a subject who has been or may have been exposed to a hepatitis virus; has a family history of liver disease; has excessive alcohol intake; or is taking a drug that can cause liver damage.

In alternative embodiments, subjects amenable to detection of EGF polymorphisms or EGF levels by the methods as disclosed herein are subjects with early or mild to moderate liver disease which can have few, if any symptoms. In such embodiments, liver disease can be detected through routine blood testing of a group of 14 tests called the Comprehensive Metabolic Panel (CMP). Most of the tests found in the liver panel (all but the direct bilirubin) are included in the CMP. When liver disease is detected with a CMP blood test, the subject can be assessed for EGF mutations and polymorphisms or EGF levels by the methods as disclosed herein.

In alternative embodiments, liver disease in a subject can be determined by a liver biopsy, where the physician examines a small piece of tissue from your liver for signs of damage or disease. A special needle is used to remove the tissue from the liver. The physician decides to do a liver biopsy after tests suggest that the liver does not work properly. For example, a blood test might show that your blood contains higher than normal levels of liver enzymes or too much iron or copper. An x ray could suggest that the liver is swollen. Looking at liver tissue itself is the best way to determine whether the liver is healthy or what is causing it to be damaged. Alternatively, Endoscopic retrograde cholangiopancreatography can enable a physician to diagnose problems in the liver, gallbladder, bile ducts, and pancreas.

In some embodiments, subjects amenable to detection of EGF polymorphisms or EGF levels by the methods as disclosed herein are subjects identified with cirrhosis. Without being bound to theory, in cirrhosis of the liver, scar tissue replaces normal, healthy tissue, blocking the flow of blood through the organ and preventing it from working as it should. Cirrhosis is the twelfth leading cause of death by disease, killing about 26,000 people each year. Many people with cirrhosis have no symptoms in the early stages of the disease. However, as scar tissue replaces healthy cells, liver function starts to fail and a subject with cirrhosis can experience one or more of the following symptoms: exhaustion, fatigue, loss of appetite, nausea, weakness, weight loss, abdominal pain, spider-like blood vessels (spider angiomas) that develop on the skin. Other complications of cirrhosis include loss of liver function which affects the body in many ways. Following are the common problems, or complications, caused by cirrhosis; Edema and ascites (when the liver loses its ability to make the protein albumin, water accumulates in the legs (edema) and abdomen (ascites)); Bruising and bleeding (when the liver slows or stops production of the proteins needed for blood clotting, a person will bruise or bleed easily. The palms of the hands may be reddish and blotchy with palmar erythema); Jaundice (yellowing of the skin and eyes that occurs when the diseased liver does not absorb enough bilirubin), Itching (bile products deposited in the skin may cause intense itching); Gallstones (if cirrhosis prevents bile from reaching the gallbladder, gallstones may develop); Toxins in the blood or brain (a damaged liver cannot remove toxins from the blood, causing them to accumulate in the blood and eventually the brain. There, toxins can dull mental functioning and cause personality changes, coma, and even death. Signs of the buildup of toxins in the brain include neglect of personal appearance, unresponsiveness, forgetfulness, trouble concentrating, or changes in sleep habits); Sensitivity to medication (cirrhosis slows the liver's ability to filter medications from the blood. Because the liver does not remove drugs from the blood at the usual rate, they act longer than expected and build up in the body. This causes a person to be more sensitive to medications and their side effects); portal hypertension (normally, blood from the intestines and spleen is carried to the liver through the portal vein. But cirrhosis slows the normal flow of blood through the portal vein, which increases the pressure inside it. This condition is called portal hypertension); Varices (when blood flow through the portal vein slows, blood from the intestines and spleen backs up into blood vessels in the stomach and esophagus. These blood vessels may become enlarged because they are not meant to carry this much blood. The enlarged blood vessels, called varices, have thin walls and carry high pressure, and thus are more likely to burst. If they do burst, the result is a serious bleeding problem in the upper stomach or esophagus that requires immediate medical attention); Insulin resistance and type 2 diabetes (cirrhosis causes resistance to insulin. This hormone, produced by the pancreas, enables blood glucose to be used as energy by the cells of the body. If you have insulin resistance, your muscle, fat, and liver cells do not use insulin properly. The pancreas tries to keep up with the demand for insulin by producing more. Eventually, the pancreas cannot keep up with the body's need for insulin, and type 2 diabetes develops as excess glucose builds up in the bloodstream) and finally liver cancer including Hepatocellular carcinoma (HCC). Cirrhosis can also cause immune system dysfunction, leading to infection. Fluid in the abdomen (ascites) may become infected with bacteria normally present in the intestines. Cirrhosis can also lead to impotence, kidney dysfunction and failure, and osteoporosis One of ordinary skill in the art can diagnose a subject with cirrhosis on the basis of symptoms, laboratory tests, the medical history, and a physical examination as disclosed herein. For example, during a physical examination, the doctor may notice that the liver feels harder or larger than usual and order blood tests that can show whether liver disease is present.

In some instances, a doctor can diagnose a subject with cirrhosis by looking at the liver, for example to check for signs of disease using a computerized axial tomography (CAT) scan, ultrasound, magnetic resonance imaging (MRI), or a scan of the liver using a radioisotope (a harmless radioactive substance that highlights the liver). Alternatively a doctor might look at the liver using a laparoscope, an instrument that is inserted through the abdomen and relays pictures back to a computer screen. A liver biopsy can confirm the diagnosis of cirrhosis in a subject. For a biopsy, the doctor uses a needle to take a tiny sample of liver tissue, then examines it under the microscope for scarring or other signs of disease.

Risk factors for a subject developing or having cirrhosis include, for example but are not limited to, chronic alcoholism and hepatitis C. Other risk factors for a subject developing or getting cirrhosis include; (i) Alcoholic liver disease; cirrhosis of the liver is synonymous with chronic alcoholism, however, alcoholism is only one of the causes of cirrhosis. Alcoholic cirrhosis usually develops after more than a decade of heavy drinking. The amount of alcohol that can injure the liver varies greatly from person to person. In women, as few as two to three drinks per day have been linked with cirrhosis and in men, as few as three to four drinks per day. Alcohol seems to injure the liver by blocking the normal metabolism of protein, fats, and carbohydrates. (ii) Chronic hepatitis C; The hepatitis C virus ranks with alcohol as a major cause of chronic liver disease and cirrhosis in the United States. Infection with this virus causes inflammation of and low grade damage to the liver that over several decades can lead to cirrhosis. (iii) Chronic hepatitis B and D. The hepatitis B virus is probably the most common cause of cirrhosis worldwide, but it is less common in the United States and the Western world. Hepatitis B, like hepatitis C, causes liver inflammation and injury that over several decades can lead to cirrhosis. Hepatitis D is another virus that infects the liver, but only in people who already have hepatitis B. (iv) Autoimmune hepatitis. This disease appears to be caused by the immune system attacking the liver and causing inflammation, damage, and eventually scarring and cirrhosis. (v) Inherited diseases. Alpha-1 antitrypsin deficiency, hemochromatosis, Wilson disease, galactosemia, and glycogen storage diseases are among the inherited diseases that interfere with the way the liver produces, processes, and stores enzymes, proteins, metals, and other substances the body needs to function properly. (vi) Nonalcoholic steatohepatitis (NASH). In NASH, fat builds up in the liver and eventually causes scar tissue. This type of hepatitis appears to be associated with diabetes, protein malnutrition, obesity, coronary artery disease, and treatment with corticosteroid medications. (v) Blocked bile ducts. When the ducts that carry bile out of the liver are blocked, bile backs up and damages liver tissue. In babies, blocked bile ducts are most commonly caused by biliary atresia, a disease in which the bile ducts are absent or injured. In adults, the most common cause is primary biliary cirrhosis, a disease in which the ducts become inflamed, blocked, and scarred. Secondary biliary cirrhosis can happen after gallbladder surgery if the ducts are inadvertently tied off or injured. (vi) Drugs, toxins, and infections. Severe reactions to prescription drugs, prolonged exposure to environmental toxins, the parasitic infection schistosomiasis, and repeated bouts of heart failure with liver congestion can all lead to cirrhosis.

Accordingly, in some embodiments, subjects amenable to detection of EGF polymorphisms or EGF levels by the methods as disclosed herein are subjects identified with at least one symptom of an inflammatory disease such as liver disease, such as cirrhosis. Alternatively, subjects amenable to detection of EGF polymorphisms or EGF levels by the methods as disclosed herein are subjects that are exposed to the risk factors of an inflammatory disease such as liver disease, such as cirrhosis as disclosed herein.

Kits to Detect EGF Polymorphisms or EGF Levels of the Present Invention

As set forth herein, the present invention provides diagnostic methods for determining the type of allelic variant of a polymorphic region present in the gene of interest or the expression level of a gene of interest. In some embodiments, the methods use probes or primers comprising nucleotide sequences which are complementary to the polymorphic region of the gene of interest. Accordingly, the present invention provides kits for performing these methods.

In an embodiment, the present invention provides a kit for determining whether a subject responds to cancer treatment or alternatively one of various treatment options. The kits contain one of more of the compositions described above and instructions for use. As an example only, the present invention also provides kits for determining response to cancer treatment containing a first and a second oligonucleotide specific for the polymorphic region of the gene. Oligonucleotides "specific for" a genetic locus bind either to the polymorphic region of the locus or bind adjacent to the polymorphic region of the locus. For oligonucleotides that are to be used as primers for amplification, primers are adjacent if they are sufficiently close to be used to produce a polynucleotide comprising the polymorphic region. In one embodiment, oligonucleotides are adjacent if they bind within about 1-2 kb, and preferably less than 1 kb from the polymorphism. Specific oligonucleotides are capable of hybridizing to a sequence, and under suitable conditions will not bind to a sequence differing by a single nucleotide.

The kit can comprise at least one probe or primer which is capable of specifically hybridizing to the polymorphic region of the gene of interest and instructions for use. The kits preferably comprise at least one of the above described nucleic acids. Preferred kits for amplifying at least a portion of the gene of interest comprise two primers, at least one of which is capable of hybridizing to the allelic variant sequence. Such kits are suitable for detection of genotype by, for example, fluorescence detection, by electrochemical detection, or by other detection.

Oligonucleotides, whether used as probes or primers, contained in a kit can be detectably labeled. Labels can be detected either directly, for example for fluorescent labels, or indirectly. Indirect detection can include any detection method known to one of skill in the art, including biotin-avidin interactions, antibody binding and the like. Fluorescently labeled oligonucleotides also can contain a quenching molecule. Oligonucleotides can be bound to a surface. In one embodiment, the preferred surface is silica or glass. In another embodiment, the surface is a metal electrode.

Yet other kits of the present invention comprise at least one reagent necessary to perform the assay. For example, the kit can comprise an enzyme. Alternatively the kit can comprise a buffer or any other necessary reagent.

Conditions for incubating a nucleic acid probe with a test sample depend on the format employed in the assay, the detection methods used, and the type and nature of the nucleic acid probe used in the assay. One skilled in the art will recognize that any one of the commonly available hybridization, amplification or immunological assay formats can readily be adapted to employ the nucleic acid probes for use in the present invention.

The test samples used in the diagnostic kits include cells, protein or membrane extracts of cells, or biological fluids such as sputum, blood, serum, plasma, or urine. The test sample used in the above described method will vary based on the assay format, nature of the detection method and the tissues, cells or extracts used as the sample to be assayed. Methods for preparing protein extracts or membrane extracts of cells are known in the art and can be readily adapted in order to obtain a sample which is compatible with the system utilized.

The kits can include all or some of the positive controls, negative controls, reagents, primers, sequencing markers, probes and antibodies described herein for determining the subject's genotype in the polymorphic region of the EGF gene.

As amenable, these suggested kit components can be packaged in a manner customary for use by those of skill in the art. For example, these suggested kit components can be provided in solution or as a liquid dispersion or the like.

The present invention provides diagnostic and therapeutic kits that include at least one primer for detecting at least one polymorphism in nucleic acids encoding an EGF molecule. In one embodiment, the kit includes a container having an oligonucleotide comprising a region of SEQ ID NOs: 5 and 6 or complement thereof for detecting the level of EGF expression (for example EGF RNA expression). In an alternative embodiment, the kit includes primers for amplifying regions of nucleic acids encoding the EGF molecule where at least one of the polymorphisms is found, such as for example SEQ ID NOs: 3 and 4 which can then be used for RFLP analysis according to the methods disclosed in the Examples. In an alternate embodiment, the kit includes allele-specific oligonucleotides, specific for both mutant and wild-type alleles of at least one polymorphism. For example, in one embodiment, the primers can be an allele specific primers of SEQ ID NO: 9 for an allele-specific primer for the A-allele at position 61 of SEQ ID NO:1, and SEQ ID NO:10 for an allele specific primer for a G-allele at position 61 of SEQ ID NO:1, where each SEQ ID NO: 9 and SEQ ID NO:10 can be used in conjunction with the primer SEQ ID NO:11. The kit can also contain sources of "control" target polynucleotides, as positive and negative controls. Such sources can be in the form of subject nucleic acid samples, cloned target poly-nucleotides, plasmids or bacterial strains carrying positive and negative control DNA. Kits according to the present invention can include one or more containers, as well as additional reagent(s) and/or active and/or inert ingredient(s) for performing any variations on the methods of the invention. Exemplary reagents include, without limitation, one or more primers, one or more terminator nucleotides, such as dideoxynucleotides, that are labeled with a detectable marker. The kits can also include instructions for mixing or combining ingredients or use.

The present invention also provides diagnostic and experimental kits which include monospecific antibodies that enable the detection, purification and/or EGF molecule or fragments thereof in a specific and reproducible manner. In these kits, the antibodies can be provided with means for binding to detectable marker moieties or substrate surfaces. Alternatively, the kits can include the antibodies already bound to marker moieties or substrates. The kits can further include positive and/or negative control reagents as well as other reagents for adapting the use of the antibodies to particular experimental and/or diagnostic techniques as desired. The kits can be prepared for in vivo or in vitro use, and can be particularly adapted for performance of any of the methods of the invention, such as ELISA. For example, kits containing antibody bound to multi-well microtiter plates can be manufactured.

A population group refers to a group of individuals or subjects sharing a common ethno-geographic origin. Reference populations include a group of subjects or individuals who are predicted to be representative of the genetic variation found in the general population. Preferably, the reference population represents the genetic variation in the population at a certainty level of at least 85%, preferably at least 90%, more preferably at least 95% and even more preferably at least 99%. After both the clinical and polymorphism data have been obtained, correlations are created between individual response and the presence of EGF polymorphism; EGF genotype; or EGF haplotype. Correlations can be produced in several ways. In one embodiment, individuals are grouped by their EGF genotype; or EGF haplotype and then the averages and standard deviations of responses exhibited by the member of each group are calculated. These results are then analyzed to determine if any observed variation in clinical response between genotype or haplotype groups is statistically significant. Another method involves categorizing the response (e.g., none, low, medium, high or other such grades) and then assessing whether a particular genotype is more common in one group of responders compared to another. Statistical analysis methods which can be used are described in L. D. Fisher and G. vanBelle, "Biostatistics: A Methodology for the Health Sciences", Wiley-Interscience (New York) 1993.

It is also contemplated that the above methods for identifying associations between a EGF polymorphism; the EGF haplotype, can be performed alone, or in combination with genotype(s) and haplotype(s) for one or more additional genomic regions.

Other objects, features and advantages will become apparent from the following detailed description. It should be understood, however, that the detailed description and specific examples, while indicating specific embodiments of the invention, are given by way of illustration only, since various changes and modifications within the spirit and scope if the present invention will become apparent to those skilled in the art from this detailed description.

The present invention now being generally described, it will be more readily understood by reference to the following examples which are included merely for purposes of illustration of certain aspects and embodiments of the present invention, and are not intended to limit the invention The following examples are provided to illustrate certain embodiments of the invention. They are not intended to limit in any way the remainder of the disclosure.

EXAMPLES

The examples presented herein relate to the identification of variances in the EGF gene. Throughout this application, various publications are referenced. The disclosures of all of the publications and those references cited within those publications in their entireties are hereby incorporated by reference into this application in order to more fully describe the state of the art to which this invention pertains. The following examples are not intended to limit the scope of the claims to the invention, but are rather intended to be exemplary of certain embodiments. Any variations in the exemplified methods which occur to the skilled artisan are intended to fall within the scope of the present invention.

The inventors herein have discovered that in subjects with cirrhosis, the presence of mutations in the 5'UTR of the EGF gene predicts in increased likelihood of developing hepatocellular cancer (HCC). In particular the inventors discovered EGF expression is elevated in 12 human hepatoma cell lines comprising the 61*G allele. Further, the inventors discovered, with use real-time PCR with allele-specific primers and ELISA methods, the stability of the EGF 61*A (61 A-allele) and 61*G (61 G-allele) alleles was different as well as the expression of EGF. Further, by investigating 207 cirrhotic patients of whom 59 had HCC, the inventors discovered an association between the EGF SNP and risk of HCC. Serum and biopsied liver tissue was obtained from a sample of these patients for analysis of EGF levels. The inventors discovered that cirrhotic subjects homozygous (two alleles) for a particular EGF polymorphism, for example the 61A>G polymorphism in the gene encoding EGF identifies subjects that are approximately five times more likely to develop hepatocellular carcinoma.

This information enables the identification of subjects that can benefit form intensive monitoring for cancer diagnosis as well as identification of subjects who would benefit from prophylactic therapies, for example but not limited to chemoprevention and other anti-cancer therapies, for example therapies that function to suppress or reduce the activity of the EGF-EGFR pathway.

Methods

Cell Culture. HCC cell lines SNU-182, SNU-387, SNU-398, SNU-423, SNU-449 and SNU-475 (16) were obtained from American Type Culture Collection (ATCC, Rockville, Md.). SK-Hep, PLC/PRF/5, HepG2 and Hep3B were kindly provided by Barrie Bode (Saint Louis University). HuH-7 was provided by Jake Liang (NIDDK, National Institutes of Health) and Focus was provided by Jack Wands (Brown University). All the cell lines were propagated in DMEM (4.5 mg/ml glucose, 2 mM L-glutamine) with 10% fetal bovine serum (both from MediaTech CellGro, Herndon, Va.), supplemented with 100 units/ml penicillin and 100 mg/ml streptomycin (Invitrogen, Carlsbad, Calif.). Cells were maintained at 37° C. in a humidified incubator with 5% CO2 in air. Primary cultures of human hepatocytes were prepared as previously described (Yoon S S, et al., [published correction appears in Ann Surg. 1998; 228(5): following. Ann Surg. 1998; 228(3):366-374).

Tissue and Clinical Information. Of 7140 patients with blood or tissue stored in the Massachusetts General Hospital Cancer Center Tumor Bank between the years 1999 and 2006, 207 were identified as having cirrhosis and were included in this study. Fifty-nine of these patients had hepatocellular carcinoma and were designated as cases, and the remaining 148 patients served as controls. Clinical information and tissues were obtained under protocols approved by the Dana-Farber Harvard Cancer Center Office for Protection of Human Subjects and the Partners Human Research Committee.

For validation of EGF gene single nucleotide polymorphism genotype results observed in the Massachusetts population, an independent group of 121 French patients with alcoholic cirrhosis seen at Hospital Paul Brousse between the years 1993 and 2006 was genotyped using blood or liver tissue as approved by Hospital Paul Brousse Centre de Resources Biologiques. Forty four of these patients had hepatocellular carcinoma (cases), and the remaining 77 patients served as controls. Neither serum nor tissue was available for analysis from this group. Ethnicity was studied because single-nucleotide polymorphism frequencies are known to differ between ethnic groups. Ethnicity was self-classified by each subject.

DNA Extraction and Genotyping of EGF Gene. DNA was extracted from HCC cell lines ($1 \times 10^6$ cells) and FFPE tissue (three 10 μm FFPE sections per each patient case) using the MasterPure Purification kit (Epicentre, Madison, Wis.) according to the manufacturer's instructions. Lymphocytes were isolated from whole blood using Histopaque1077® (Sigma, St. Louis, Mo.), followed by DNA isolation as described above. The SNP was identified by restriction fragment length polymorphism (RFLP) as described previously (15). Briefly, genomic DNA was subjected to PCR (initial denaturation of 95° C. for 5 min, followed by 35 cycles of 95° C. for 30 s, 51° C. for 30 s, and 72° C. for 1 min with a final extension step of 7 min at 72° C.) to amplify nucleotide positions −78 to +164 of the EGF gene. The following primers were used: forward—TGTCACTAAAGGAAAG-GAGGT (SEQ ID NO: 3) and reverse—TTCACAGAGTT-TAACAGCCC (SEQ ID NO:4). The 25 μl PCR product was digested overnight with 5 units of AluI at 37° C., separated by electrophoresis in a 3% agarose gel and visualized by staining with ethidium bromide. AluI cut the 242 bp PCR product containing the 61*G allele into 15, 34, and 193 bp fragments, while digestion of the 61*A allele produced 15, 34, 91, and 102 bp fragments.

Real-Time PCR. EGF mRNA in HCC cell lines was measured by quantitative reverse transcription-PCR (LightCycler; Roche Diagnostics Corporation, Indianapolis, Ind.). Cells were plated at $1 \times 10^5$ cells/ml in 10 ml media in 10 cm plates and allowed to grow for 48 h to reach log phase growth. Total RNA was extracted from each cell line using TRIzol® (Invitrogen) according to the manufacturer's instructions and subsequently treated with DNase (Promega, Madison, Wis.). 250 ng of total RNA from each sample was used to synthesize cDNA by single strand reverse transcription (SuperScript III® First-Strand Synthesis SuperMix for qRT-PCR; Invitrogen). All of the sample cDNAs were pooled together to create a quantitative standard control. The level of EGF mRNA present is expressed as the ratio of EGF PCR product to beta-2-microglobulin (B2M) PCR product. All reactions were performed in duplicate and experiments were repeated to ensure accuracy. The following primer sequences were used for PCR amplification of cDNA, EGF forward: CTTGT-CATGCTGCTCCTCCT (SEQ ID NO: 5), reverse: GAGGGCATATGAAAGCTTCG (SEQ ID NO: 6) and B2M forward: TTTCATCCATCCGACATTGA (SEQ ID NO: 7), reverse: ATCTTCAAACCTCCATGATG (SEQ ID NO: 8).

For mRNA stability studies, PLC/PRF/5 cells were plated at $1 \times 10^5$ cells/ml in 10 ml media in 10 cm plates. After 48 h, cells were washed once with PBS and fresh media was added containing 5 μg/ml actinomycin D (Sigma). At the indicated times, RNA was isolated and cDNA was synthesized as described above. A quantitative standard control was created from the Time Zero cDNA (control) and the level of EGF mRNA present at each time point is expressed as the percent of control. All of the reactions were performed in duplicate and the experiment was repeated to ensure accuracy. The following allele-specific primers were used: A-allele specific forward primer: EGF 61*A forward: GCCCCAATC-CAAGGGTTGTA (SEQ ID NO: 9); G-allele specific forward primer: EGF 61*G forward: GCCCCAATC-CAAGGGTTGTG (SEQ ID NO: 10); and reverse primer for both alleles: GCCAAGGGAAGCCACAGGAAAG (SEQ ID NO: 11). Similar studies were performed on primary cultures of human hepatocytes established from resected liver specimens from EGF 61A/G (heterozygous) patients. Hepatocyte cultures were established as previously described (Yoon et al., FASEB J. 2000; 14(2):301-311).

EGF and Phospho-EGF Receptor Enzyme-Linked Immunosorbent Assay (ELISA). The phosphorylated EGF receptor was quantified using an enzyme-linked immunosorbent assay (R&D Systems, Minneapolis, Minn.). EGF protein was quantified using an ELISA (PeproTech, Rocky Hill, N.J.) in triplicate and experiments were repeated to ensure accuracy. Cells were plated at $1 \times 10^5$ cells/ml in 10 ml media in 10 cm plates. After 48 h, cells were washed in ice-cold PBS and harvested in 500 ml of RIPA Buffer (Boston BioProducts, Worcester, Mass.) containing protease inhibitors (Sigma). For tissue lysates, 0.01 g of tissue was cut into small pieces, resuspended on ice in 400 ml of RIPA buffer containing protease inhibitors and homogenized with a sonicator. Lysates were incubated on ice for 10 min with occasional vortexing and then centrifuged at 12,000 rpm for 30 min at 4° C. The supernatant was removed and protein concentration was analyzed by the bicinchoninic acid (BCA) method (Pierce Chemical Co., Rockford, Ill.). Each ELISA plate well was incubated overnight with 100 μl capture antibody (1 μg/ml) before blocking with 1% BSA in PBS for 1 h. Cell or tissue lysates (100 mg per well) were incubated for 2 h, followed by addition of 100 μl of detection antibody (0.25 μg/ml) for 2 h before incubation with 100 μl of avidin peroxidase (1:2000) for 30 min. Wells were washed 4× with PBS containing 0.05% Tween-20 between each step. Color development was monitored at 405 nm after the addition of 100 μl of 2,2'-Azino-bis(3-ethylbenzothiazoline-6-sulfonic acid) (ABTS; Sigma) using a spectrophotometric plate reader (Emax; Molecular Devices).

To measure EGF in conditioned media, $1 \times 10^5$ cells in 2 ml media were grown in a 6 cm plate for 24 h. Cells were then washed with PBS and 2 ml of fresh media was added. After 48 h, the media was collected for analysis and the cells were harvested in 0.2% SDS+0.2 N NaOH to determine protein content by BCA. Conditioned media (100 ml per well) was analyzed and results were normalized to the number of cells present as determined by the BCA. For serum analysis, 10 ml of freshly obtained blood (red top tube) was allowed to clot for 30 min at 4° C. before centrifugation at 2,000 rpm for 10 min at 4° C. Serum was isolated and stored at −80° C. prior to use.

Cells and Culture Conditions. The normal human liver epithelial cell line, THLE-5B, was kindly provided by Curtis Harris (NCI, National Institutes of Health, Bethesda, Md.). THLE-5B cells were propagated in DMEM/F-12 (1:1; Invitrogen, Carlsbad, Calif.) with 10% fetal bovine serum (MediaTech CellGro, Herndon, Va.), that was supplemented with 100 units/ml penicillin, 100 mg/ml streptomycin (both from Invitrogen), 10 μg/ml insulin, 10 μg/ml transferrin and 10 ng/ml selenium (ITS; Lonza, Walkersville, Md.). Primary human hepatocytes were isolated as described before and cultured in HMM media (Lonza). Cells were maintained at 37° C. in a humidified incubator with 5% $CO_2$ in air.

Chemicals. Stock solutions of AG1478 (Invitrogen), erlotinib (Tarceva™; Genentech, South San Francisco, Calif.) and gefitinib (Iressa™; AstraZeneca, Wilmington, Del.) were prepared in DMSO and stored at −20° C. EGF (Sigma, St. Louis, Mo.) stock solution was prepared in 10 mM acetic acid and diluted in PBS.

Anchorage-Independent Transformation Assay. Because cells suspended in soft agar cannot be easily recovered, the inventors used the previously described over-agar assay which allows for the analysis of molecular events associated with tumor promoter-induced cell transformation under anchorage-independent conditions. Briefly, $1 \times 10^4$ THLE-5B cells or isolated human hepatocytes were plated onto 0.5% BME agar containing the indicated concentrations of EGF and inhibitors. The plates were cultured for 14 days, after which colonies of transformed cells were counted using a microscope. The results represent one experiment and are presented as the mean±standard deviation of colony counts made by three separate investigators. The experiments were repeated twice to ensure qualitatively similar results.

Cell Growth Assay. Briefly, THLE-5B cells were plated in triplicate at a density of $4\times10^4$ cells/ml in a 24-well plate. After 24 h, cells were washed once with PBS and medium containing inhibitors at the indicated concentrations or vehicle control was added. After 72 h, the effects of each inhibitor on growth of the cells was measured by colorimetric 3-(4,5-dimethylthiazol-2-yl)-2,5-diphenyltetrazolium bromide (MTT; Sigma) assay. The absorbance at 562 nm was measured using a spectrophotometric plate reader (Emax; Molecular Devices) and the experiment was repeated twice to ensure qualitatively similar results for each inhibitor.

Statistical Methods: Comparisons of groups with regard to risk of HCC was made using a Cox regression model; age, sex, ethnicity, etiology of cirrhosis, and severity of cirrhosis were included as covariates in addition to genotype. Comparisons of EGF expression in cell lines and tissue/serum by number of copies of G were made using a regression model; Jonckheere-Terpstra test; pair-wise comparisons were made using exact Wilcoxon-Mann-Whitney test in StatXact (Cytel Inc, Cambridge, Mass.). Comparisons of rates of hepatocellular carcinoma in groups defined by genotype were made using Fisher Exact test.

Example 1

EGF Polymorphisms Demonstrate Increased Stability of mRNA

To analyze potential mechanisms by which the EGF SNP modulates EGF expression, an Restriction fragment length polymorphism (RFLP) strategy was used to genotype 12 human hepatoma cell lines for the presence of the A to G SNP at position 61 of the EGF gene (FIG. 1A). Three of the cell lines proved to be the A/A genotype, seven were G/G, and two were A/G. Because allelic variation in gene expression can result from differences in mRNA stability (17), real-time PCR with allele-specific primers was used to determine the stability of the different alleles after treatment with actinomycin D (5 µg/ml). The PLC/PRF/5 (FIGS. 1B and 5A) and HepG (FIG. 5B) cell-lines were used for this experiment because they are heterozygous at the EGF SNP, which allows for stability of both types of EGF mRNA transcripts to be assessed in an otherwise identical environment.

Figure 1B:
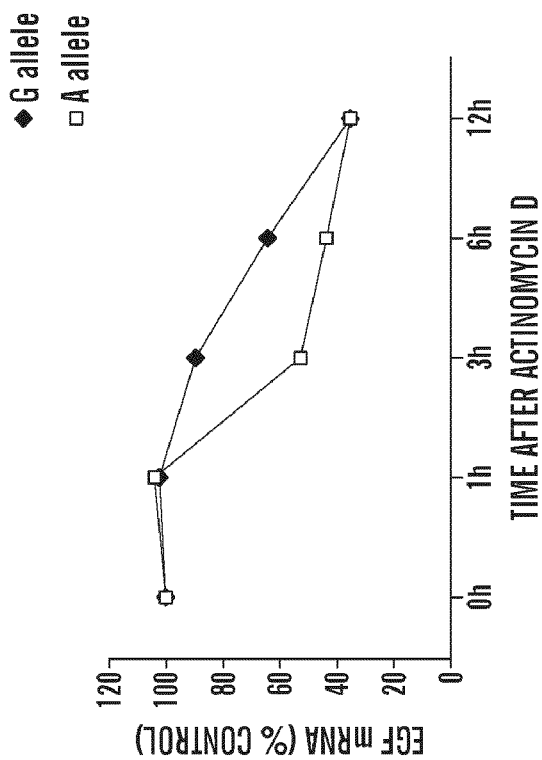
Figure 5B:
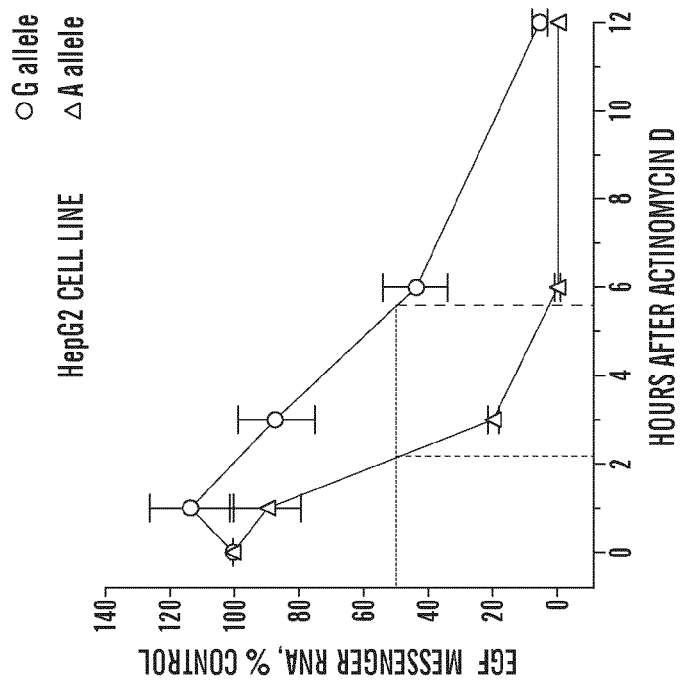
FIG. 5A-5D shows allelic messenger mRNA in EGF gene single-nucleotide polymorphism heterozygous cells after treatment with actinomycin D. Cells were treated with 5 µg of actinomycin D. Allelic messenger mRNA stability was determined by real-time polymerase chain reaction with allele-specific primers.
Figure 5A:
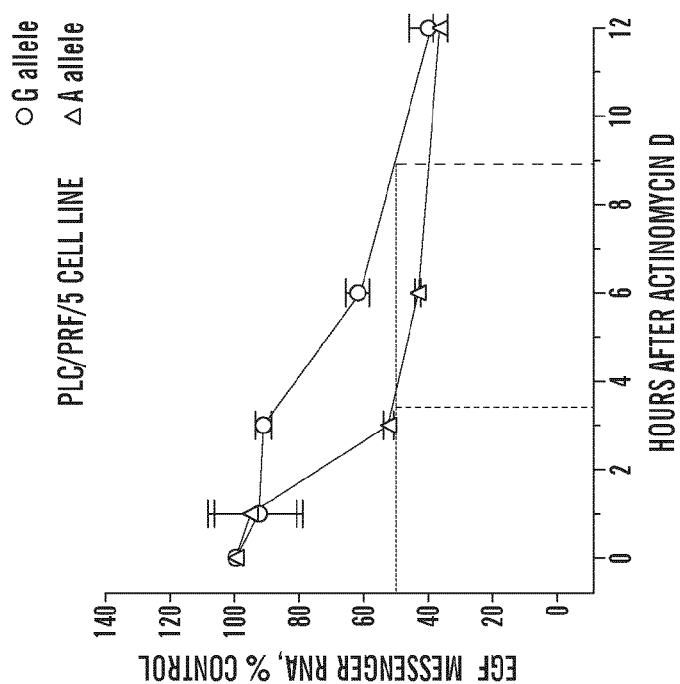
Figure 5C:
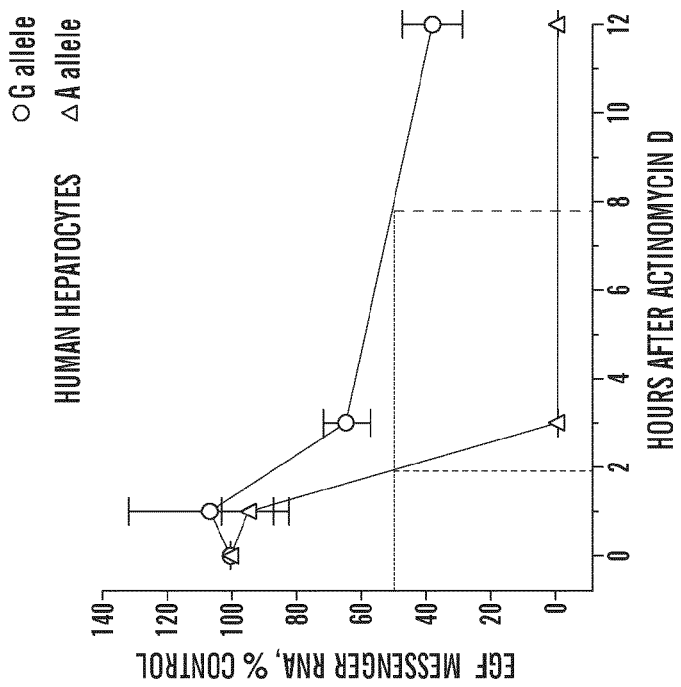
Figure 5D:
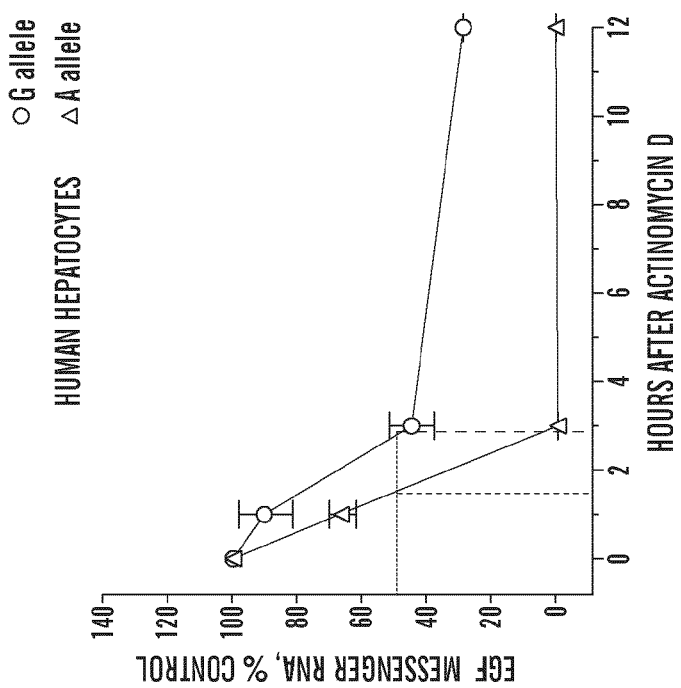

The mRNA half-life for transcripts from the G allele was significantly longer than the half-life of A allele transcripts (9 hrs versus 3 hrs) for both cell lines (FIG. 1B, 5A and FIG. 5B). Greater stability of G allele compared with A allele transcripts was also observed in primary cultures of hepatocytes from patients heterozygous at the EGF gene polymorphism ($P<0.01$; FIGS. 5C and 5D). As summarized in Table 1, in accord with the greater stability of G allele mRNA, EGF mRNA increased with the number of copies of G in the seven human HCC cell lines (p=0.06). Levels of intracellular EGF protein were significantly greater in cell lines with more copies of G in the genotype (p=0.005), and cell lines secreted significantly more EGF into media with the more copies of G in the genotype (p=0.002). The increased EGF secreted by human HCC cell lines of the G/G genotype was associated with EGFR downstream signaling, with greater ratios of phospho-STAT3:total STAT3 in these cell lines compared to A/A cell lines (data not shown).

TABLE 1

Median EGF expression levels from hepatoma cell lines

| | | | | P value* | | |
|---|---|---|---|---|---|---|
| | A/A | A/G | G/G | A/G vs. A/A | G/G vs. A/A | **Over all |
| RNA, median (range), EGF:beta$_2$-microglobulin ratio | 0.22 (0.03-0.24) | 0.52 (0.45-0.58) | 0.91 (0.43-3.46) | 0.14 | 0.02 | 0.06 |
| Protein, median (range), pg/ml | 58 (45-70) | 61 (55-66) | 112 (63-141) | >.099 | 0.03 | 0.005 |
| Media, median (range), pg EGF/mg protein/48 hrs | 9 (0-10) | 14 (12-14) | 21 (11-28) | 0.14 | 0.02 | 0.002 |

*Wilcoxon-Mann-Whitney test,
**Regression analysis of effect of number of copies of G on measure of EGF expression level Example 2

EGF Polymorphisms in Cirrhotic Patients with Hepatocellular Carcinoma

Because EGF over-expression in the liver leads to development of HCC in mouse models (13, 14), the inventors determined whether the EGF SNP genotype correlates with risk for HCC in all patients identified as having cirrhosis in the Massachusetts General Hospital Cancer Center Tumor bank.

The EGF SNP allelic distribution was examined in 207 patients with cirrhosis, and of these 207 patients, 59 also had hepatocellular carcinoma (Table 2). Clinically relevant factors of age, severity of cirrhosis, etiology of cirrhosis, sex, and ethnicity were evaluated. (Duration of cirrhosis cannot be determined with accuracy.) Sex and ethnic distribution were similar in A/A, A/G, and G/G patients, with minor exception of Asians having slightly more G copies than Caucasians. The median age and etiology of cirrhosis was also similar amongst the three groups. The duration of cirrhosis could not be assessed; however, the median age of patients at time of biospecimen collection was similar amongst the three genotypes. The severity of cirrhosis as assessed by laboratory values used in the Child classification—total bilirubin, albumin, prothrombin time—were similar among the groups with the exception of slightly lower albumin levels in G/G patients relative to A/A patients. Total bilirubin, albumin, and protime values were similar amongst the groups with the singular exception of slightly lower albumin levels in G/G patients relative to A/A patients.

Patients with an A/G or G/G genotype had a 2.4-fold or 4.0-fold, respectively, relative risk of developing HCC compared to A/A patients (Table 3). The number of copies of G was significantly associated with hepatocellular carcinoma (P=0.001), further confirming this result. Logistic regression analysis demonstrates that number of copies of G was significantly associated with hepatocellular carcinoma, after adjusting for age, sex, race, etiology, and severity of cirrhosis (G/G plus A/G patients vs. A/A patients hazard ratio, 3.49; 95% confidence interval [CI], 1.29-9.44; P=0.01).

Figure 2:
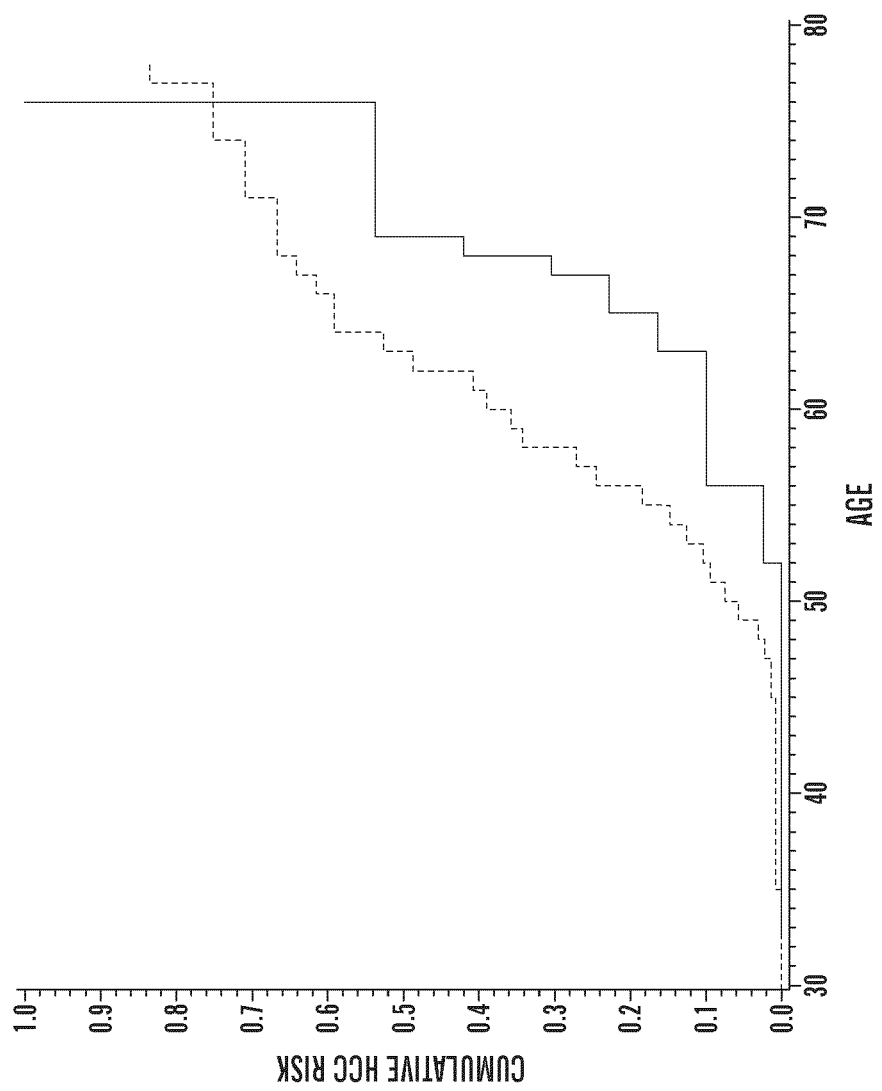
FIG. 2 shows Kaplan-Meier curves comparing age at HCC diagnosis by genotype. A/A patients (solid line) are compared to patients with 1 or 2 copies of G (dashed line) (log rank p=0.0085).

The risk of HCC was significantly higher in patients with the G/G genotype than in patients with the A/A genotype (hazard ratio from Cox model 2.48, p=0.01). Moreover, the age at which patients with one or two G alleles developed HCC was younger than A/A patients (p=0.0085; FIG. 2). Two studies have examined EGF SNP allelic distribution in normal populations from the United States. The inventors compared the genotype distribution in our patients against that of healthy control populations reported in these studies (i.e. patients without cirrhosis). When compared to these healthy controls, the relative risk of HCC in individuals with the G/G genotype is greater than 7-fold compared to A/A patients (Table 4). The inventors have discovered an absence of difference in EGF SNP allele distribution between healthy controls and cirrhotic patients, indicating that the G/G genotype is associated with a risk of developing HCC in patients with cirrhosis, rather than a risk of developing cirrhosis.

TABLE 2

General Characteristics of Massachusetts study group.

|  | A/A (n = 60) | A/G (n = 92) | G/G (n = 55) | P value |
|---|---|---|---|---|
| Age, mean, y | 56 | 54 | 55 | 0.38 |
| Men, No (%) | 44 (73) | 67 (73) | 43 (78) | 0.72 |
| Race or Ethnicity, No. (%) | | | | |
| White | 56 (93) | 78 (85) | 42 (76) | |
| Black | 2 (3) | 5 (5) | 4 (7) | 0.62 |
| Hispanic | 2 (3) | 5 (5) | 3 (5) | 0.84 |
| Asian | 0 (0) | 2 (2) | 5 (9) | 0.01* |
| Other | 0 (0) | 2 (2) | 1 (1) | 0.62 |
| Cirrhosis etiology, No. (%) | | | | |
| HCV | 23 (38) | 40 (44) | 22 (40) | 0.22 |
| HBV | 0 (0) | 2 (2) | 5 (9) | |
| Alcohol | 10 (17) | 11 (12) | 4 (7) | |
| Multiple | 9 (15) | 16 (17) | 10 (18) | |
| Other | 18 (30) | 23 (25) | 14 (26) | |
| Laboratory values, mean (SD) | | | | |
| Albumin, g/dL | 3.4 (0.7) | 3.3 (0.8) | 3.1 (0.7) | 0.01** |
| Total bilirubin, mg/dL | 4.9 (10.5) | 5.2 (8.7) | 4.2 (6.2) | .075 |
| Prothrombin time, s | 15.4 (2.9) | 15.6 (3.6) | 15.5 (2.6) | 0.75 |
| Platelets, 1000/μl | 109.2 (77.8) | 92.9 (49.9) | 116.9 (87.6_ | 0.10 |

(*compared to while individuals,
**G/G versus A/A).
SI conversion factor; To convert biliruben from mg/dL to μmol/L, multiply by 17.104. Abbreviations: HBV, hepatitis B virus; HCV, hepatitis C virus.

TABLE 3

Comparison of EGF genotypes and allelic frequencies in patients with cirrhosis versus patients with HCC and cirrhosis.

|  | Cirrhosis n = 148 (%) | Cirrhosis + HCC n = 59 (%) | Odds Ratio (95% confidence interval) | p value |
|---|---|---|---|---|
| A/A | 51 (34) | 9 (15) | 1.0 [Reference] | — |
| A/G | 65 (44) | 27 (46) | 2.4 (0.1-5.4) | p = 0.05 |
| G/G | 33 (22) | 23 (39) | 4.0 (1.6-9.6) | p = 0.002 |
| A | 167 (56) | 45 (38) | 1.0 [Reference] | — |
| G | 129 (44) | 73 (62) | 2.1 (1.4-3.3) | p = 0.001 |

Abbreviations: HCC = hepatocellular carcinoma.

TABLE 4

Comparison of EGF genotypes and allelic frequencies between normal controls reported in published literature and patients with cirrhosis and HCC in the Examples.

|  | Bhowmick et al (Ref 22) N = 76 (%) | Cirrhosis + HCC n = 59 (%) | Odds Ratio (95% confidence interval) | p value |
|---|---|---|---|---|
| A/A | 27 (36) | 9 (15) | 1.0 | — |
| A/G | 37 (48) | 27 (46) | 2.2 (0.9-5.4) | 0.13 |
| G/G | 12 (16) | 23 (39) | 5.8 (2.1-16.1) | 0.001 |
| A | 91 (60) | 45 (38) | 1.0 | |
| G | 61 (40) | 73 (62) | 2.4 (1.5-4.0) | 0.001 |

|  | Amend et al (Ref 23) n = 232 (%) | Cirrhosis + HCC n = 59 (%) | Odds Ratio (95% confidence interval) | p value |
|---|---|---|---|---|
| A/A | 84 (36) | 9 (15) | 1.0 | — |
| A/G | 118 (51) | 27 (46) | 2.1 (1.0-4.8) | 0.07 |
| G/G | 30 (13) | 23 (39) | 7.2 (3.0-17.2) | 0.001 |

TABLE 4-continued

Comparison of EGF genotypes and allelic frequencies between normal controls reported in published literature and patients with cirrhosis and HCC in the Examples.

| | | | | |
|---|---|---|---|---|
| A | 286 (62) | 45 (38) | 1.0 | |
| G | 178 (38) | 73 (62) | 2.6 (1.7-4.0) | <0.001 |

Example 3

EGF levels and phospo EGF levels were measured in liver tissue specimens from twelve randomly selected patients of each genotype with cirrhosis (36 patients in total). EGF levels were significantly higher in G/G patients as compared to A/A patients (p=0.004) (Table 5). Consistent with the finding that elevated EGF levels was the discovery that the highest levels of phosphorylated EGF receptor in livers from G/G patients as compared to A/A patients (P=0.04). Serum was also isolated from twelve patients of each genotype with cirrhosis for measurement of EGF levels.

TABLE 5

Median EGF protein expression level by genotype from Liver Tissue and Serum, and phosphor-EGF receptor in Liver Tissue.

| | Median Expression level by genotype, Median (Range) | | | *p value A/G vs. A/A | *p value G/G vs. A/A | **overall p value |
|---|---|---|---|---|---|---|
| | A/A | A/G | G/G | | | |
| Tissue, pg/ml | 59 (37-88) | 96 (94-108) | 140 (82-181) | 0.002 | 0.004 | <0.001 |
| Serum, pg/ml | 778 (433-1011) | 1117 (470-1756) | 1378 (663-4233) | 0.02 | 0.0003 | 0.001 |
| Phospho-EGF-receptor, pg/ml | 109 (70-138) | 118 (75-205) | 147 (85-418) | 0.29 | 0.04 | 0.02 |

*Wilcoxan Mann-Whitney test,
**Jonckheere-Terpestra non-parametric test.

The inventors then measured EGF in serum rather than in plasma because the major source of EGF in the blood is platelets (Oka et al., J Clin Invest. 1983; 72(1):249-259). Consistent with the results from liver biopsy tissue, the level of EGF in the serum from G/G patients was significantly higher than in A/A patients (p=0.0003). Epidermal growth factor levels were not merely a result of greater cholestasis; neither serum (p=0.47) nor liver (p=0.62) EGF levels correlated with bilirubin.

Example 4

The inventors confirmed the relationship between EGF SNP genotype and risk for HCC in a separate cohort of cirrhotic patients. Investigators at Hôpital Paul Brousse have published studies of the risk of HCC in alcoholic cirrhotic patients based on polymorphisms of the methylenetetrahydrofolate reductase gene (20). For purposes of an EGF SNP validation study, the inventors used a French study cohort in which alcohol consumption was the only known etiology of cirrhosis; all patients tested negative for hepatitis A, B, and C.

The EGF SNP allelic distribution was examined in this cohort of 121 Caucasian patients with cirrhosis, of whom 44 had HCC arising in their cirrhotic livers. The duration of cirrhosis could not be assessed; however, the median age of patients was similar among the three genotypes (Table 6). Child class was similar in A/A, A/G, and G/G patients (Table 6). Total bilirubin, albumin, and prothrombin-time values were similar among the groups, with the exception of a trend towards lower platelet counts in G/G patients relative to A/A patients.

Patients with a G/G genotype were demonstrated to have a 2.9-fold increased risk of developing HCC as compared to A/A patients (Table 7). Logistic regression analysis demonstrated that number of copies of G was significantly associated with hepatocellular carcinoma after adjusting for age, sex, and Child class (G/G patients vs. A/G plus A/A patients hazard ratio, 4.87; 95% CI, 1.26-18.77; P=0.021)

In concert, these results demonstrate that EGF SNP genotype is associated with an increased risk for the development of HCC in patients with liver cirrhosis by modulation of EGF levels. The association between G/G genotype and increased EGF levels is present in both cirrhosis and hepatocellular carcinoma, and measurement of serum EGF levels can serve as a novel marker for risk of HCC development in patients with cirrhosis.

TABLE 6

General characteristics of French study group.

| | A/A (n = 40) | A/G (n = 54) | G/G (n = 27) | P value |
|---|---|---|---|---|
| Age, mean, y | 53 | 54 | 53 | 0.79 |
| Men, No (%) | 36 (90) | 45 (83) | 20 (74) | 0.22 |
| White, No (%) | 40 (100) | 54 (100) | 27 (100) | |
| Cirrhosis due to alcohol, No. (%) | 40 (100) | 54 (100) | 27 (100) | |
| Child Class, No (%) | | | | |
| A | 9 (23) | 5 (9) | 5 (19) | 0.08 |
| B | 9 (23) | 27 (50) | 10 (37) | |
| C | 22 (55) | 22 (41) | 12 (44) | |
| Laboratory values, mean (SD) | | | | |
| Albumin, g/L | 33 (10) | 31 (7) | 31 (6) | 0.26 |
| Total bilirubin, μmol/L | 3.1 (4.2) | 2.6 (2.0) | 6.0 (4.0) | 0.28 |
| Prothrombin time, % | 54 (16) | 58 (19) | 54 (20) | 0.38 |
| Platelets, 1000/μl | 154 (101) | 135 (64) | 106 (62) | 0.08 |

SI conversion factor: To convert bilirubin from mg/dL, multiply by 17.104

TABLE 7

Comparison of EGF genotype and Allelic frequencies in French study group patients with cirrhosis versus patients with HCC and cirrhosis.

|  | Cirrhosis n = 77 (%) | Cirrhosis + HCC n = 44 (%) | Odds Ratio (95% confidence interval) | p value |
|---|---|---|---|---|
| A/A | 28 (36) | 12 (27) | 1 [Reference] |  |
| A/G | 37 (48) | 17 (39) | 1.1 (0.4-2.6) | >0.99 |
| G/G | 12 (16) | 15 (34) | 2.9 (1.1-8.1) | 0.045 |
| A | 93 (60) | 41 (47) | 1 [Reference] |  |
| G | 61 (40) | 47 (53) | 1.7 (1.0-3.0) | <0.044 |

Example 5

Figure 6A:
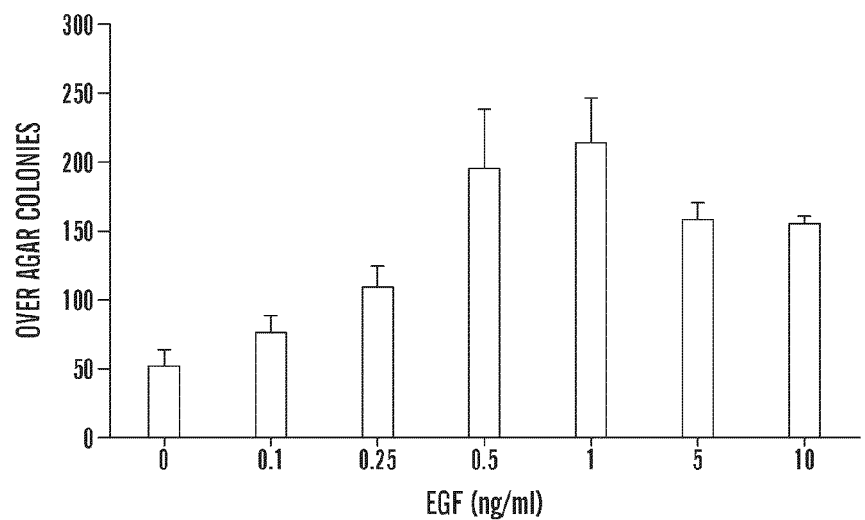
FIGS. 6A-6B shows EGF induces anchorage-independent growth of primary human hepatocytes and THLE-5B cells in a dose-dependent fashion.
Figure 6B:
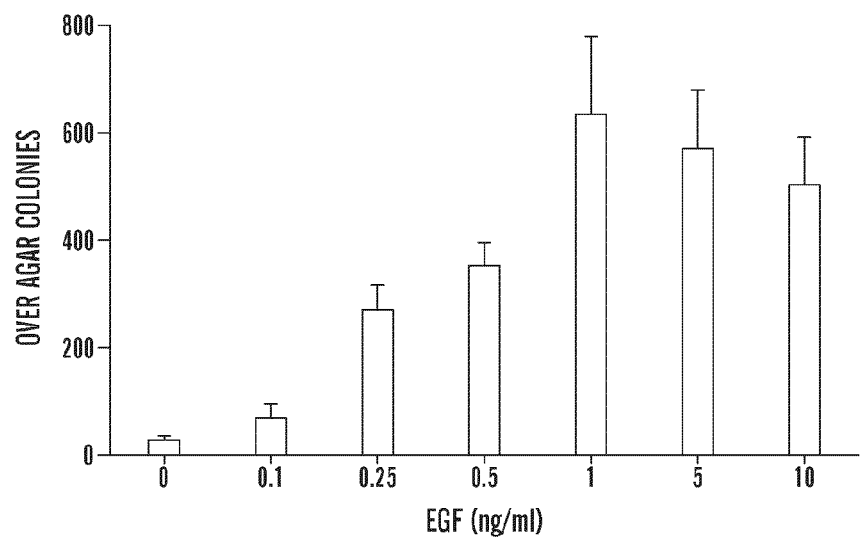

The inventors further demonstrated, using an over agar assay as described in the methods section, that primary human hepatocytes and a human liver cell line were transformed with increased levels of EGF protein. As demonstrated in FIGS. 6A and 6B, increased levels of EGF protein (ng/ml) induced anchorage independent growth in primary human hepatocytes (FIG. 6A) and a normal human liver cell epithelial cell line THLE-5B (FIG. 6B).

Figure 7B:
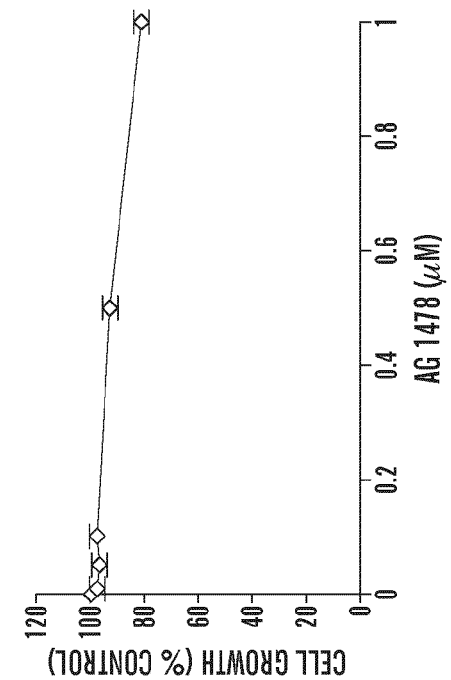
FIGS. 7A-7F shows EGF-induced anchorage-independent transformation is inhibited by three different EGFR inhibitors.
Figure 7A:
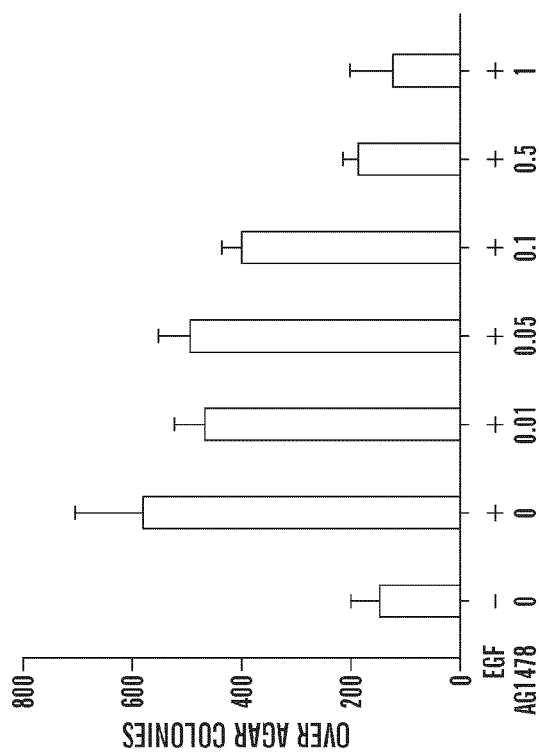
Figure 7D:
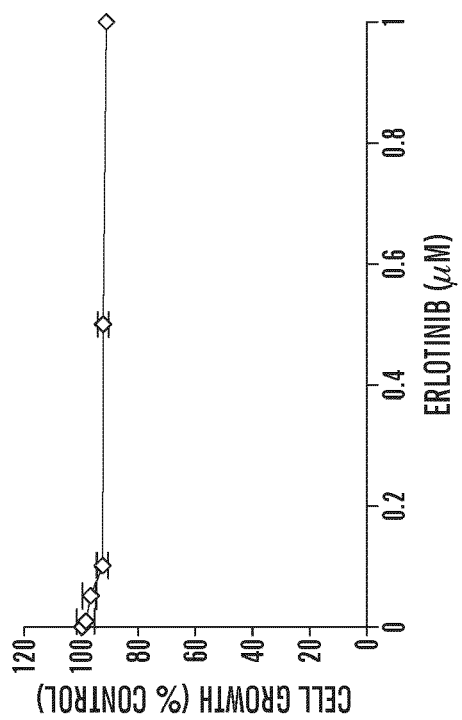
Figure 7C:
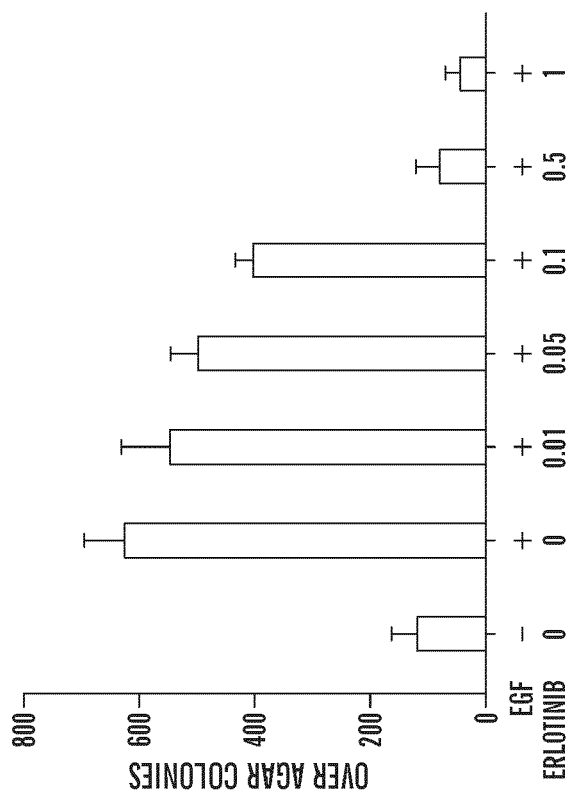
Figure 7F:
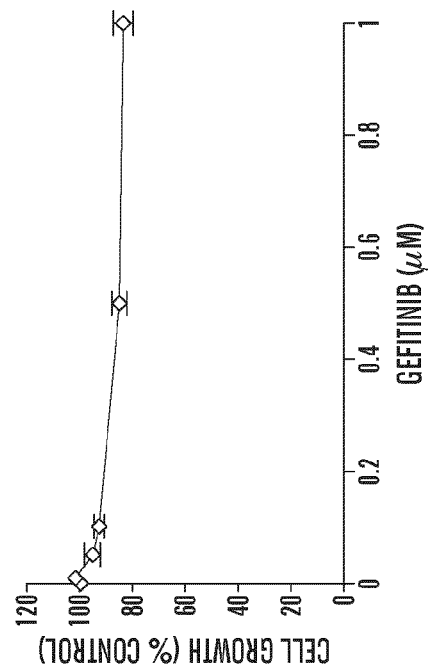
Figure 7E:
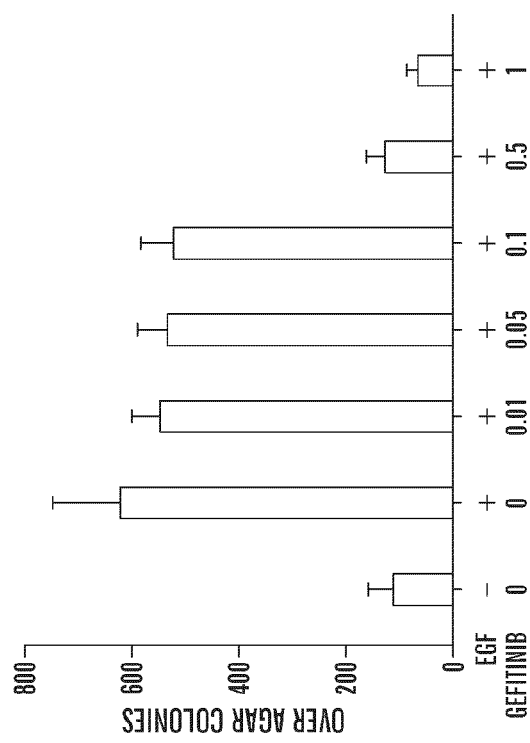

The inventors further demonstrated, using the anchorage independent transformation assay, that in the presence of 10 ng/ml EGF protein, increasing concentrations of EGF inhibitors AG1478, Erlotinib and Gefitnib (from 0.01 µM to 1.0 µM) prevents EGF mediated anchorage-independent transformation of THLE-5B cells (see FIGS. 7A, 7C and 7E) at concentrations of the these EGF inhibitors which are not cytotoxic to the THLE-5B cells (as shown by the MTT assays in FIGS. 7B, 7D and 7F, respectively). Moreover, the concentrations of the EGF inhibitors AG1478, Erlotinib and Gefitnib which were demonstrated to be effective in preventing EGF mediated anchorage-independent transformation of THLE-5B cells are similar to the plasma concentrations of such inhibitors seen in clinical trials with erlotinib and gefitinib. As such, the inventors demonstrate that inhibition of EGF signaling is a useful and an effective strategy to prevent human hepatocyte transformation and can be used to prevent the development of HCC in human subjects that have been identified to have increased risk of developing HCC by the methods as disclosed herein.

Much effort has been directed towards understanding the role of the EGF receptors and its signaling pathways in transformation (18), tumor progression (19), and drug response (20). The data shown in the Examples herein provide evidence of the importance of EGF in hepatocellular transformation in humans and highlights the important role of EGF on the initiation of a primary tumor during the responses of the liver to chronic injury. Using 2 independent studies; 55 subjects with the G/G SNP in the Massachusetts cohort, of which 23 (4%) developed HCC, and an independent cohort of cirrhotic patients, the inventors have discovered the importance of EGF in hepatocellular transformation in humans, and the association between EGF SNP and HCC. The inventors have discovered that EGF SNP analysis and serum EGF measurements serve as novel makers for risk of HCC in patients with cirrhosis. EGF upregulation is a characteristic of cirrhotic liver disease and human hepatocytes transformation is enhanced by EGF. Differences in stability of mRNA transcribed from the 2 alleles are important because they lead to increased EGF mRNA expression in G/G cell lines. These mRNA stability experiments are of significance because of the observation that serum and liver EGF levels are greater in G/G vs. A/A patients. The lack of an association between this EGF gene polymorphism and plasma EGF levels has been reported in a group of patients without cirrhosis (Berrahmoune et al., J Invest Dermatol. 2007; 127(4):969-970). However, the major source of EGF in blood is platelets (Oka et al., J Clin Invest. 1983; 72(1):249-259) and therefore the inventors performed EGF measurements in serum and in liver tissue, which are presumed to be most relevant to hepatocyte transformation in cirrhosis.

The inventors have discovered the importance of examination of other potential influences that modify EGF levels (e.g. age, ethnicity, diet, medications) can also modulate the risk for HCC. Of note, the two cohorts involved in these examples differ primarily in the etiology of cirrhosis—predominantly HCV in the Massachusetts cohort, and solely alcohol in the French cohort. And although the association between EGF SNP and risk for HCC in cirrhotic patients is stronger in the Massachusetts study cohort than in the French cohort, the prognostic value of the EGF SNP was confirmed in both cohorts. Furthermore, in the examples herein, there is little equivocating between the present and absence of HCC in these well-studies populations, in which explanted livers were carefully evaluated for the presence of HCC.

The Examples also highlight the use of chemoprevention strategies that target the EGF-EGFR pathway as promising novel approach for subjects and/or patients with cirrhosis who are at risk for HCC. For example, Schiffer et al. demonstrated in a rat model in which DEN induces cirrhosis within 12 weeks and subsequent HCC at 18 weeks that concurrent treatment with the selective EGFR tyrosine kinase inhibitor gefitinib during weeks 12-18 significantly reduced the formation of HCC nodules (21). The inventors have discovered a screening strategy for patients with different cirrhotic conditions, as well as a method to tailor screening strategies of different cirrhotic populations based on the risk of HCC, based on the identification of other modulators of EGF levels and therefore the development of chemopreventative strategies.

Recognizing the extremely high frequency of polymorphic changes in the human genome, Rosenthal and Schwartz (Rosenthal et al. N Engl J Med. 1998; 338(2):122) propose several criteria to establish medically useful links between polymorphisms and disease. First, it is essential to show that the change in the gene causes a relevant alteration in the function or level of the gene product. The inventors have demonstrated herein that modulation of EGF levels by the EGF gene polymorphism; moreover, the inventors have discovered and demonstrated a mechanism by which EGF levels are modulated.

Second, the number of cases associating an allele with a particular phenotype must be large enough to be convincing. As disclosed herein in the Examples, the present study involves 55 individuals with the G/G single nucleotide polymorphism in the Massachusetts study group, of which 23 (42%) had hepatocellular carcinoma. Using an independent group of cirrhotic patients, the inventors have validated the association between EGF gene single nucleotide polymorphism and hepatocellular carcinoma.

Third, the beneficial and harmful phenotypes being studied must have clear-cut clinical differences. As demonstrated herein, there is little equivocating between the presence and absence of hepatocellular carcinoma in these well studied populations, in which explanted livers were carefully evaluated for the presence of hepatocellular carcinoma.

Fourth, the plausibility of the hypothesis must be convincing. Studies demonstrating enhanced in vitro transformation in the presence of EGF, combined with animal models in which liver-directed EGF overexpression causes hepatocellular carcinoma provide extremely strong support for the linkage between EGF gene polymorphism and hepatocellular carcinoma. (Tonjes et al. Oncogene. 1995; 10(4):765-768; Borlak et al., Oncogene. 2005; 24(11):1809-1819.)

In addition, it has been proposed that the correlation between a particular single-nucleotide polymorphism and a disease should have practical value. As disclosed herein, the inventors have demonstrated a significant and immediate practical value in their relevance to tailoring of screening strategies for different cirrhotic populations based on their likelihood of developing hepatocellular carcinoma, identification of other modulators of EGF levels, and development of chemoprevention strategies that target EGF or EGF receptor. Thus, a compound or agent that effectively and safely lowers EGF levels in a subject would function to decrease the risk for hepatocellular carcinoma in the subject, and would be highly useful for chemoprevention, which would be a great benefit as a cost effective preventative strategy as compared with strategies aimed at early detection and treatment of hepatocellular carcinoma.

Schiffer et al (Schiffer et al., Hepatology. 2005; 41(2):307-314) demonstrated in a rat model in which diethylnitrosamine induces cirrhosis within 12 weeks and subsequent hepatocellular carcinoma at 18 weeks that concurrent treatment with the selective EGF receptor tyrosine kinase inhibitor gefitinib during weeks 12 through 18 significantly reduced the formation of hepatocellular carcinoma nodules. When combined with these preclinical study results, our findings in humans provide rationale for examination of EGF-EGF receptor pathway as a novel target for chemoprevention in humans.

The inventors herein have discovered that EGF expression in hepatocarcinogenesis in cirrhotic patients provide striking evidence for the clinical relevance and therapeutic rationale for examination of EGF-EGFR pathway as a novel target for chemoprevention of HCC in subjects with cirrhosis. Unlike the situation related to the previously published report linking EGF SNP and melanoma (15), the presence of cirrhosis is an important risk factor for developing HCC. Accordingly, the inventors have discovered a specific criteria to prevent HCC in a subject at risk of developing HCC; where only the presence of cirrhosis (regardless of etiology) and either EGF SNP 61A>G allele and/or elevated EGF protein and/or elevated EGF mRNA, would one consider a chemopreventive strategy. In some instances, such a chemoprotective strategy can be with agents, such as those that block the EGF-EGFR pathway, for example, but not limited to gefitinib.

The inventors are the first to discover a relationship between EGF SNP genotype in patients with cirrhosis and their risk of HCC and provide evidence of the importance of EGF in hepatocellular transformation in humans. Unlike the situation related to the previously published report linking the EGF gene single-nucleotide polymorphism and melanoma, (Shahbazi et al., Lancet. 2002; 359(9304):397-401) the inventors have discovered that the presence of cirrhosis appears to be an important prerequisite to developing HCC in subjects with a EGF 61*G allele. Thus, one could consider a chemoprevention strategy using agents that block the EGF-EGF receptor pathway in a defined population with cirrhosis with a EGF 61*G allele.

REFERENCES

Throughout this disclosure, various publications, patents and published patent specifications are referenced by an identifying citation. The disclosures of these publications, patents and published patent specifications are hereby incorporated by reference into the present disclosure to more fully describe the state of the art to which this invention pertains. The references cited herein and throughout the application are incorporated herein by reference.

1. Thomas M B, Zhu A X. Hepatocellular carcinoma: the need for progress. J Clin Oncol 2005; 23:2892-9.
2. Parkin D M, Bray F, Ferlay J, Pisani P. Global cancer statistics, 2002. CA Cancer J Clin 2005; 55:74-108.
3. Llovet J M, Burroughs A, Bruix J. Hepatocellular carcinoma. Lancet 2003; 362:1907-17.
4. Cohen S. Isolation of a mouse submaxillary gland protein accelerating incisor eruption and eyelid opening in the new-born animal. J Biol Chem 1962; 237: 1555-62.
5. Carpenter G, Cohen S. Epidermal growth factor. Annu Rev Biochem 1979; 48:193-216.
6. Fisher D A, Lakshmanan J. Metabolism and effects of epidermal growth factor and related growth factors in mammals. Endocr Rev 1990; 11:418-42.
7. Blanc P, Etienne H, Daujat M, Fabre I, Zindy F, Domergue J, Astre C, Saint Aubert B, Michel H, Maurel P. Mitotic responsiveness of cultured adult human hepatocytes to epidermal growth factor, transforming growth factor alpha, and human serum. Gastroenterology 1992; 102:1340-50.
8. Hoffmann B, Piasecki A, Paul D. Proliferation of fetal rat hepatocytes in response to growth factors and hormones in primary culture. J Cell Physiol 1989; 139:654-62.
9. Mullhaupt B, Feren A, Fodor E, Jones A. Liver expression of epidermal growth factor RNA. Rapid increases in immediate-early phase of liver regeneration. J Biol Chem 1994; 269: 19667-70.
10. Stoscheck C M, King L E, Jr. Role of epidermal growth factor in carcinogenesis. Cancer Res, 1986; 46: 1030-7.
11. Singletary S E, Baker F L, Spitzer G, Tucker S L, Tomasovic B, Brock W A, Ajani J A, Kelly A M. Biological effect of epidermal growth factor on the in vitro growth of human tumors. Cancer Res 1987; 47:403-6.
12. Stern D F, Hare D L, Cecchini M A, Weinberg R A. Construction of a novel oncogene based on synthetic sequences encoding epidermal growth factor. Science 1987; 235:321-4.
13. Tonjes R R, Lohler J, O'Sullivan J F, Kay G F, Schmidt G H, Dalemans W, Pavirani A, Paul D. Autocrine mitogen IgEGF cooperates with c-myc or with the Hcs locus during hepatocarcinogenesis in transgenic mice. Oncogene 1995; 10:765-8.
14. Borlak J, Meier T, Halter R, Spanel R, Spanel-Borowski K. Epidermal growth factor-induced hepatocellular carcinoma: gene expression profiles in precursor lesions, early stage and solitary tumours. Oncogene 2005; 24:1809-19.
15. Shahbazi M, Pravica V, Nasreen N, Fakhoury H, Fryer A A, Strange R C, Hutchinson P E, Osborne J E, Lear J T, Smith A G, Hutchinson I V. Association between functional polymorphism in EGF gene and malignant melanoma. Lancet 2002; 359:397-401.
16. Park J G, Lee J H, Kang M S, Park K J, Jeon Y M, Lee H J, Kwon H S, Park H S, Yeo K S, Lee K U, et al. Characterization of cell lines established from human hepatocellular carcinoma. Int J Cancer 1995; 62:276-82.
17. Ding C, Maier E, Roscher A A, Braun A, Cantor C R. Simultaneous quantitative and allele-specific expression analysis with real competitive PCR. BMC Genet 2004; 5:8.
18. Greulich H, Chen T H, Feng W, Janne P A, Alvarez J V, Zappaterra M, Bulmer S E, Frank D A, Hahn W C, Sellers W R, Meyerson M. Oncogenic transformation by inhibitor-sensitive and -resistant EGFR mutants. PLoS Med 2005; 2:e313.

19. Sainsbury J R, Famdon J R, Sherbet G V, Harris A L. Epidermal-growth-factor receptors and estrogen receptors in human breast cancer. Lancet 1985; 1:364-366.
20. Lynch T J, Bell D W, Sordella R, Gurubhagavatula 5, Okimoto R A, Brannigan B W, Harris P L, Haserlat S M, Supko J G, Haluska F G, Louis D N, Christiani D C, Settleman J, Haber D A. Activating mutations in the epidermal growth factor receptor underlying responsiveness of non-small-cell lung cancer to gefitinib. N. Engl. J. Med. 2004; 350:2129-2139.
21. Schiffer E, Housset C, Cacheux W, Wendum D, Desbois-Mouthon C, Rey C, Clergue F, Poupon R, Barbu V, Rosmorduc O. Gefitinib, an EGFR inhibitor, prevents hepatocellular carcinoma development in the rat liver with cirrhosis. Hepatology 2005; 41:307-14.
22. Bhowmick D A, Zhuang Z, Wait S D, Weil R J. A functional polymorphism in the EGF gene is found with increased frequency in glioblastoma multiform patients and is associated with more aggressive disease. Cancer Res 2004; 64: 1220-3.
23. Amend K L, Elder J T, Tomsho L P, Boimer J D, Johnson T M, Schwartz J, Berwick M, Gruber S B. EGF gene polymorphism and the risk of incident primary melanoma. Cancer Res 2004; 64:2668-72.
24. Marti et al. Biological Effects of EGF, with Emphasis on the GI Tract and Liver: An Update. Hepatology 1989.
25. Le Gall et al. Regulated Cell Surface Pro-EGF Ectodomain Shedding is a Zinc Metalloprotease-dependent Process. JBC 2003.
26. Sahin et al. Distinct roles for ADAM10 and ADAM17 in ectodomain shedding of six EGFR ligands. J. Cell Biol. 2004.
27. Lakshmanan et al. Epidermal growth factor prohormone is secreted in human urine. Am. J. Physiol. 1992.
28. Pesonen et al. Size Heterogeneity of EGF in Human Body Fluids. Life Sciences 1987.
29. Lev Ran et al. Human serum and plasma have different sources of epidermal growth factor. Am. J. Physiol. 1990.

We claim:

1. A method of identifying a human subject with liver fibrosis or cirrhosis as having an increased likelihood of developing a liver cancer, the method comprising detecting a guanine (G) nucleotide at position 61 of the 5'untranslated (5'UTR) region of the human EGF gene in a biological sample obtained from a human subject having liver fibrosis or cirrhosis, and identifying the human subject with liver fibrosis or cirrhosis as having an increased likelihood of developing liver cancer based on the presence of the guanine (G) nucleotide at position 61 of the 5' untranslated (UTR) region of the human EGF gene.

2. The method of claim 1, wherein the liver cancer is hepatocellular carcinoma (HCC).

3. The method of claim 1, wherein the liver fibrosis or cirrhosis is selected from a group consisting of: liver diseases due to alcohol, alcoholic hepatitis or cirrhosis, fibrosis and cirrhosis of the liver due to inborn errors of metabolism of exogenous substances, drug-induced disorders of the liver, and primary biliary cirrhosis.

4. The method of claim 1, wherein the biological sample is selected from a group consisting of blood, serum, plasma, urine, stool, spinal fluid, pleural fluid, sputum, nipple aspirates, lymph fluid, the external secretions of the skin, respiratory, intestinal, and genitourinary tracts, bile, tears, sweat, saliva, milk, cells, tumors, organs, and samples of in vitro cell culture constituent.

* * * * *

SEQUENCE LISTING

<160> NUMBER OF SEQ ID NOS: 11

<210> SEQ ID NO 1
<211> LENGTH: 4877
<212> TYPE: DNA
<213> ORGANISM: Homo sapiens

<400> SEQUENCE: 1

```
actgttggga gaggaatcgt atctccatat ttcttctttc agccccaatc caagggttgt      60
agctggaact ttccatcagt tcttcctttc tttttcctct ctaagccttt gccttgctct     120
gtcacagtga agtcagccag agcagggctg ttaaactctg tgaaatttgt cataagggtg     180
tcaggtattt cttactggct tccaaagaaa catagataaa gaaatctttc ctgtggcttc     240
ccttggcagg ctgcattcag aaggtctctc agttgaagaa agagcttgga ggacaacagc     300
acaacaggag agtaaaagat gccccagggc tgaggcctcc gctcaggcag ccgcatctgg     360
ggtcaatcat actccaccttg cccgggccat gctccagcaa aatcaagctg tttttctttg     420
aaagttcaaa ctcatcaaga ttatgctgct cactcttatc attctgttgc cagtagtttc     480
aaaatttagt tttgttagtc tctcagcacc gcagcactgg agctgtcctg aaggtactct     540
cgcaggaaat gggaattcta cttgtgtggg tcctgcaccc ttcttaattt tctcccatgg     600
aaatagtatc tttaggattg acacagaagg aaccaattat gagcaattgg tggtggatgc     660
tggtgtctca gtgatcatgg attttcatta taatgagaaa agaatctatt gggtggattt     720
agaaagacaa cttttgcaaa gagttttttct gaatgggtca aggcaagaga gagtatgtaa     780
tatagagaaa aatgtttctg gaatggcaat aaattggata aatgaagaag ttatttggtc     840
aaatcaacag gaaggaatca ttacagtaac agatatgaaa ggaaataatt cccacattct     900
tttaagtgct ttaaaatatc ctgcaaatgt agcagttgat ccagtagaaa ggtttatatt     960
ttggtcttca gaggtggctg gaagcctttta tagagcagat ctcgatggtg tgggagtgaa    1020
ggctctgttg gagacatcag agaaaataac agctgtgtca ttggatgtgc ttgataagcg    1080
gctgttttgg attcagtaca acagagaagg aagcaattct cttatttgct cctgtgatta    1140
tgatggaggt tctgtccaca ttagtaaaca tccaacacag cataattttgt ttgcaatgtc    1200 ccttttggt gaccgtatct tctattcaac atggaaaatg aagacaattt ggatagccaa    1260
caaacacact ggaaaggaca tggttagaat taacctccat tcatcatttg taccacttgg    1320
```

```
tgaactgaaa gtagtgcatc cacttgcaca acccaaggca gaagatgaca cttgggagcc   1380
tgagcagaaa cttttgcaaat tgaggaaagg aaactgcagc agcactgtgt gtgggcaaga   1440
cctccagtca cacttgtgca tgtgtgcaga gggatacgcc ctaagtcgag accggaagta   1500
ctgtgaagat gttaatgaat gtgcttttg gaatcatggc tgtactcttg ggtgtaaaaa    1560 caccctgga tcctattact gcacgtgccc tgtaggattt gttctgcttc ctgatgggaa    1620
acgatgtcat caacttgttt cctgtccacg caatgtgtct gaatgcagcc atgactgtgt   1680
tctgacatca gaaggtccct tatgtttctg tcctgaaggc tcagtgcttg agagagatgg   1740
gaaaacatgt agcggttgtt cctcacccga taatggtgga tgtagccagc tctgcgttcc   1800
tcttagccca gtatcctggg aatgtgattg cttccctggg tatgacctac aactggatga   1860
aaaaagctgt gcagcttcag gaccacaacc atttttgctg tttgccaatt ctcaagatat   1920
tcgacacatg cattttgatg aacagacta tggaactctg ctcagccagc agatgggaat    1980
ggtttatgcc ctagatcatg accctgtgga aaataagata tactttgccc atacagccct   2040
gaagtggata gagagagcta atatggatgg ttcccagcga gaaaggctta ttgaggaagg   2100
agtagatgtg ccagaaggtc ttgctgtgga ctggattggc cgtagattct attggacaga   2160
cagagggaaa tctctgattg aaggagtga tttaaatggg aaacgttcca aaataatcac    2220
taaggagaac atctctcaac cacgaggaat tgctgttcat ccaatggcca agagattatt   2280
ctggactgat acaggattaa tccacgaat tgaaagttct tccctccaag gccttggccg    2340
tctggttata gccagctctg atctaatctg gcccagtgga ataacgattg acttcttaac   2400
tgacaagttg tactggtgcg atgccaagca gtctgtgatt gaaatggcca atctggatgg   2460
ttcaaaacgc cgaagactta cccagaatga tgtaggtcac ccatttgctg tagcagtgtt   2520
tgaggattat gtgtggttct cagattgggc tatgccatca gtaataagag taaacaagag   2580
gactggcaaa gatagagtac gtctccaagg cagcatgctg aagccctcat cactggttgt   2640
ggttcatcca ttggcaaaac caggagcaga tccctgctta tatcaaaacg gaggctgtga   2700
acatatttgc aaaagaggc ttggaactgc ttggtgttcg tgtcgtgaag gttttatgaa    2760
agcctcagat gggaaaacgt gtctggctct ggatggtcat cagctgttgg caggtggtga   2820
agttgatcta aagaaccaag taacaccatt ggacatcttg tccaagacta gagtgtcaga   2880
agataacatt acagaatctc aacacatgct agtggctgaa atcatggtgt cagatcaaga   2940
tgactgtgct cctgtgggat gcagcatgta tgctcggtgt atttcagagg gagaggatgc   3000
cacatgtcag tgtttgaaag gatttgctgg ggatggaaaa ctatgttctg atatagatga   3060
atgtgagatg ggtgtcccag tgtgcccccc tgcctcctcc aagtgcatca acaccgaagg   3120
tggttatgtc tgccggtgct cagaaggcta ccaaggagat gggattcact gtcttgatat   3180
tgatgagtgc caactggggg tgcacagctg tggagagaat gccagctgca caaatacaga   3240
gggaggctat acctgcatgt gtgctggacg cctgtctgaa ccaggactga tttgccctga   3300
ctctactcca ccccctcacc tcagggaaga tgaccaccac tattccgtaa gaaatagtga   3360
ctctgaatgt cccctgtccc acgatgggta ctgcctccat gatggtgtgt gcatgtatat   3420
tgaagcattg acaagtatg catgcaactg tgttgttggc tacatcgggg agcgatgtca    3480
gtaccgagac ctgaagtggt gggaactgcg ccacgctggc cacgggcagc agcagaaggt   3540
catcgtggtg gctgtctgcg tggtggtgct tgtcatgctg ctcctcctga gcctgtgggg   3600
ggcccactac tacaggactc agaagctgct atcgaaaaac ccaaagaatc cttatgagga   3660
gtcgagcaga gatgtgagga gtcgcaggcc tgctgacact gaggatggga tgtcctcttg   3720
```

```
cccctcaacct tggtttgtgg ttataaaaga acaccaagac ctcaagaatg ggggtcaacc    3780
agtggctggt gaggatggcc aggcagcaga tgggtcaatg caaccaactt catggaggca    3840
ggagccccag ttatgtggaa tgggcacaga gcaaggctgc tggattccag tatccagtga    3900
taagggctcc tgtccccagg taatggagcg aagctttcat atgccctcct atgggacaca    3960 gaccccttgaa gggggtgtcg agaagcccca ttctctccta tcagctaacc cattatggca    4020
acaaagggcc ctggacccac cacaccaaat ggagctgact cagtgaaaac tggaattaaa    4080
aggaaagtca agaagaatga actatgtcga tgcacagtat ctttctcttc aaaagtagag    4140
caaaactata ggttttggtt ccacaatctc tacgactaat cacctactca atgcctggag    4200
acagatacgt agttgtgctt ttgtttgctc ttttaagcag tctcactgca gtcttatttc    4260
caagtaagag tactgggaga atcactaggt aacttattag aaacccaaat tgggacaaca    4320
gtgctttgta aattgtgttg tcttcagcag tcaatacaaa tagattttg ttttgttgt    4380 tcctgcagcc ccagaagaaa ttaggggtta aagcagacag tcacactggt ttggtcagtt    4440
acaaagtaat ttctttgatc tggacagaac atttatatca gtttcatgaa atgattggaa    4500
tattacaata ccgttaagat acagtgtagg catttaactc ctcattggcg tggtccatgc    4560
tgatgatttt gccaaaatga gttgtgatga atcaatgaaa aatgtaattt agaaactgat    4620
ttcttcagaa ttagatggcc ttattttta aaatatttga atgaaaacat tttatttta    4680 aaatattaca caggaggcct tcggagtttc ttagtcatta ctgtcctttt ccctacaga    4740 atttccctc ttggtgtgat tgcacagaat ttgtatgtat tttcagttac aagattgtaa    4800
gtaaattgcc tgatttgttt tcattataga caacgatgaa tttcttctaa ttatttaaat    4860
aaaatcacca aaaacat                                                   4877

<210> SEQ ID NO 2
<211> LENGTH: 1207
<212> TYPE: PRT
<213> ORGANISM: Homo sapiens

<400> SEQUENCE: 2

Met Leu Leu Thr Leu Ile Ile Leu Leu Pro Val Val Ser Lys Phe Ser
1               5                   10                  15

Phe Val Ser Leu Ser Ala Pro Gln His Trp Ser Cys Pro Glu Gly Thr
            20                  25                  30

Leu Ala Gly Asn Gly Asn Ser Thr Cys Val Gly Pro Ala Pro Phe Leu
        35                  40                  45

Ile Phe Ser His Gly Asn Ser Ile Phe Arg Ile Asp Thr Glu Gly Thr
    50                  55                  60

Asn Tyr Glu Gln Leu Val Val Asp Ala Gly Val Ser Val Ile Met Asp
65                  70                  75                  80

Phe His Tyr Asn Glu Lys Arg Ile Tyr Trp Val Asp Leu Glu Arg Gln
                85                  90                  95

Leu Leu Gln Arg Val Phe Leu Asn Gly Ser Arg Gln Glu Arg Val Cys
            100                 105                 110

Asn Ile Glu Lys Asn Val Ser Gly Met Ala Ile Asn Trp Ile Asn Glu
        115                 120                 125

Glu Val Ile Trp Ser Asn Gln Gln Glu Gly Ile Ile Thr Val Thr Asp
    130                 135                 140

Met Lys Gly Asn Asn Ser His Ile Leu Leu Ser Ala Leu Lys Tyr Pro
145                 150                 155                 160

Ala Asn Val Ala Val Asp Pro Val Glu Arg Phe Ile Phe Trp Ser Ser
```

```
                      165                 170                 175
            Glu Val Ala Gly Ser Leu Tyr Arg Ala Asp Leu Asp Gly Val Gly Val
                        180                 185                 190
            Lys Ala Leu Leu Glu Thr Ser Glu Lys Ile Thr Ala Val Ser Leu Asp
                        195                 200                 205
            Val Leu Asp Lys Arg Leu Phe Trp Ile Gln Tyr Asn Arg Glu Gly Ser
                        210                 215                 220
            Asn Ser Leu Ile Cys Ser Cys Asp Tyr Asp Gly Gly Ser Val His Ile
            225                 230                 235                 240
            Ser Lys His Pro Thr Gln His Asn Leu Phe Ala Met Ser Leu Phe Gly
                            245                 250                 255
            Asp Arg Ile Phe Tyr Ser Thr Trp Lys Met Lys Thr Ile Trp Ile Ala
                        260                 265                 270
            Asn Lys His Thr Gly Lys Asp Met Val Arg Ile Asn Leu His Ser Ser
                        275                 280                 285
            Phe Val Pro Leu Gly Glu Leu Lys Val Val His Pro Leu Ala Gln Pro
                        290                 295                 300
            Lys Ala Glu Asp Asp Thr Trp Glu Pro Glu Gln Lys Leu Cys Lys Leu
            305                 310                 315                 320
            Arg Lys Gly Asn Cys Ser Ser Thr Val Cys Gly Gln Asp Leu Gln Ser
                            325                 330                 335
            His Leu Cys Met Cys Ala Glu Gly Tyr Ala Leu Ser Arg Asp Arg Lys
                        340                 345                 350
            Tyr Cys Glu Asp Val Asn Glu Cys Ala Phe Trp Asn His Gly Cys Thr
                        355                 360                 365
            Leu Gly Cys Lys Asn Thr Pro Gly Ser Tyr Tyr Cys Thr Cys Pro Val
                        370                 375                 380
            Gly Phe Val Leu Leu Pro Asp Gly Lys Arg Cys His Gln Leu Val Ser
            385                 390                 395                 400
            Cys Pro Arg Asn Val Ser Glu Cys Ser His Asp Cys Val Leu Thr Ser
                            405                 410                 415
            Glu Gly Pro Leu Cys Phe Cys Pro Glu Gly Ser Val Leu Glu Arg Asp
                        420                 425                 430
            Gly Lys Thr Cys Ser Gly Cys Ser Ser Pro Asp Asn Gly Gly Cys Ser
                        435                 440                 445
            Gln Leu Cys Val Pro Leu Ser Pro Val Ser Trp Glu Cys Asp Cys Phe
                        450                 455                 460
            Pro Gly Tyr Asp Leu Gln Leu Asp Glu Lys Ser Cys Ala Ala Ser Gly
            465                 470                 475                 480
            Pro Gln Pro Phe Leu Leu Phe Ala Asn Ser Gln Asp Ile Arg His Met
                            485                 490                 495
            His Phe Asp Gly Thr Asp Tyr Gly Thr Leu Leu Ser Gln Gln Met Gly
                        500                 505                 510
            Met Val Tyr Ala Leu Asp His Asp Pro Val Glu Asn Lys Ile Tyr Phe
                        515                 520                 525
            Ala His Thr Ala Leu Lys Trp Ile Glu Arg Ala Asn Met Asp Gly Ser
                        530                 535                 540
            Gln Arg Glu Arg Leu Ile Glu Glu Gly Val Asp Val Pro Glu Gly Leu
            545                 550                 555                 560
            Ala Val Asp Trp Ile Gly Arg Arg Phe Tyr Trp Thr Asp Arg Gly Lys
                            565                 570                 575
            Ser Leu Ile Gly Arg Ser Asp Leu Asn Gly Lys Arg Ser Lys Ile Ile
                        580                 585                 590
```

-continued

```
Thr Lys Glu Asn Ile Ser Gln Pro Arg Gly Ile Ala Val His Pro Met
        595                 600                 605

Ala Lys Arg Leu Phe Trp Thr Asp Thr Gly Ile Asn Pro Arg Ile Glu
610                 615                 620

Ser Ser Ser Leu Gln Gly Leu Gly Arg Leu Val Ile Ala Ser Ser Asp
625                 630                 635                 640

Leu Ile Trp Pro Ser Gly Ile Thr Ile Asp Phe Leu Thr Asp Lys Leu
                645                 650                 655

Tyr Trp Cys Asp Ala Lys Gln Ser Val Ile Glu Met Ala Asn Leu Asp
                    660                 665                 670

Gly Ser Lys Arg Arg Leu Thr Gln Asn Asp Val Gly His Pro Phe
                675                 680                 685

Ala Val Ala Val Phe Glu Asp Tyr Val Trp Phe Ser Asp Trp Ala Met
690                 695                 700

Pro Ser Val Ile Arg Val Asn Lys Arg Thr Gly Lys Asp Arg Val Arg
705                 710                 715                 720

Leu Gln Gly Ser Met Leu Lys Pro Ser Ser Leu Val Val His Pro
                    725                 730                 735

Leu Ala Lys Pro Gly Ala Asp Pro Cys Leu Tyr Gln Asn Gly Gly Cys
                740                 745                 750

Glu His Ile Cys Lys Lys Arg Leu Gly Thr Ala Trp Cys Ser Cys Arg
        755                 760                 765

Glu Gly Phe Met Lys Ala Ser Asp Gly Lys Thr Cys Leu Ala Leu Asp
770                 775                 780

Gly His Gln Leu Leu Ala Gly Gly Glu Val Asp Leu Lys Asn Gln Val
785                 790                 795                 800

Thr Pro Leu Asp Ile Leu Ser Lys Thr Arg Val Ser Glu Asp Asn Ile
                    805                 810                 815

Thr Glu Ser Gln His Met Leu Val Ala Glu Ile Met Val Ser Asp Gln
                820                 825                 830

Asp Asp Cys Ala Pro Val Gly Cys Ser Met Tyr Ala Arg Cys Ile Ser
                835                 840                 845

Glu Gly Glu Asp Ala Thr Cys Gln Cys Leu Lys Gly Phe Ala Gly Asp
        850                 855                 860

Gly Lys Leu Cys Ser Asp Ile Asp Glu Cys Glu Met Gly Val Pro Val
865                 870                 875                 880

Cys Pro Pro Ala Ser Ser Lys Cys Ile Asn Thr Glu Gly Gly Tyr Val
                    885                 890                 895

Cys Arg Cys Ser Glu Gly Tyr Gln Gly Asp Gly Ile His Cys Leu Asp
                900                 905                 910

Ile Asp Glu Cys Gln Leu Gly Val His Ser Cys Gly Glu Asn Ala Ser
                915                 920                 925

Cys Thr Asn Thr Glu Gly Gly Tyr Thr Cys Met Cys Ala Gly Arg Leu
        930                 935                 940

Ser Glu Pro Gly Leu Ile Cys Pro Asp Ser Thr Pro Pro His Leu
945                 950                 955                 960

Arg Glu Asp Asp His His Tyr Ser Val Arg Asn Ser Ser Glu Cys
                    965                 970                 975

Pro Leu Ser His Asp Gly Tyr Cys Leu His Asp Gly Val Cys Met Tyr
                980                 985                 990

Ile Glu Ala Leu Asp Lys Tyr Ala Cys Asn Cys Val Val Gly Tyr Ile
                995                 1000                 1005

Gly Glu Arg Cys Gln Tyr Arg Asp Leu Lys Trp Trp Glu Leu Arg His
        1010                 1015                 1020
```

```
Ala Gly His Gly Gln Gln Gln Lys Val Ile Val Val Ala Val Cys Val
1025                1030                1035                1040

Val Val Leu Val Met Leu Leu Leu Ser Leu Trp Gly Ala His Tyr
            1045                1050                1055

Tyr Arg Thr Gln Lys Leu Leu Ser Lys Asn Pro Lys Asn Pro Tyr Glu
        1060                1065                1070

Glu Ser Ser Arg Asp Val Arg Ser Arg Pro Ala Asp Thr Glu Asp
    1075                1080                1085

Gly Met Ser Ser Cys Pro Gln Pro Trp Phe Val Val Ile Lys Glu His
    1090                1095                1100

Gln Asp Leu Lys Asn Gly Gly Gln Pro Val Ala Gly Glu Asp Gly Gln
1105                1110                1115                1120

Ala Ala Asp Gly Ser Met Gln Pro Thr Ser Trp Arg Gln Glu Pro Gln
            1125                1130                1135

Leu Cys Gly Met Gly Thr Glu Gln Gly Cys Trp Ile Pro Val Ser Ser
            1140                1145                1150

Asp Lys Gly Ser Cys Pro Gln Val Met Glu Arg Ser Phe His Met Pro
        1155                1160                1165

Ser Tyr Gly Thr Gln Thr Leu Glu Gly Gly Val Glu Lys Pro His Ser
    1170                1175                1180

Leu Leu Ser Ala Asn Pro Leu Trp Gln Gln Arg Ala Leu Asp Pro Pro
1185                1190                1195                1200

His Gln Met Glu Leu Thr Gln
            1205

<210> SEQ ID NO 3
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 3
tgtcactaaa ggaaaggagg t                                              21

<210> SEQ ID NO 4
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 4
ttcacagagt ttaacagccc                                                20

<210> SEQ ID NO 5
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 5
cttgtcatgc tgctcctcct                                                20

<210> SEQ ID NO 6
<211> LENGTH: 20
<212> TYPE: DNA
```

```
<213> ORGANISM: Artificial Sequence
<220> FEATURE:
<223> OTHER INFORMATION: Description of Artificial Sequence: Synthetic
      primer

<400> SEQUENCE: 6
gagggcatat gaaagcttcg                                               20

<210> SEQ ID NO 7
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 7
tttcatccat ccgacattga                                               20

<210> SEQ ID NO 8
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 8
atcttcaaac ctccatgatg                                               20

<210> SEQ ID NO 9
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 9
gccccaatcc aagggttgta                                               20

<210> SEQ ID NO 10
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 10
gccccaatcc aagggttgtg                                               20

<210> SEQ ID NO 11
<211> LENGTH: 22
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 11
gccaagggaa gccacaggaa ag                                            22
```